(12) United States Patent
Chapple et al.

(10) Patent No.: US 7,071,376 B2
(45) Date of Patent: Jul. 4, 2006

(54) GENES ENCODING P-COUMARATE 3-HYDROXYLASE (C3H) AND METHODS OF USE

(75) Inventors: Clinton C. S. Chapple, West Lafayette, IN (US); Rochus Franke, Kaiserslautern (DE); Max O. Ruegger, Indianapolis, IN (US)

(73) Assignee: Purdue Research Foundation, West Lafayette, IN (US)

( * ) Notice: Subject to any disclaimer, the term of this patent is extended or adjusted under 35 U.S.C. 154(b) by 294 days.

(21) Appl. No.: 09/931,267

(22) Filed: Aug. 16, 2001

(65) Prior Publication Data
US 2002/0062496 A1 May 23, 2002

Related U.S. Application Data

(60) Provisional application No. 60/225,554, filed on Aug. 16, 2000.

(51) Int. Cl.
*C12N 15/29* (2006.01)
*C12N 15/55* (2006.01)
*C12N 15/82* (2006.01)
*A01H 5/00* (2006.01)

(52) U.S. Cl. .................... 800/286; 800/278; 800/285; 800/298

(58) Field of Classification Search ................ 800/278, 800/285, 286, 290, 298; 536/23.1, 23.2, 23.6
See application file for complete search history.

(56) References Cited

U.S. PATENT DOCUMENTS 5,850,020 A * 12/1998 Bloksberg et al. .......... 800/278
5,981,837 A    11/1999 Chapple
6,066,780 A     5/2000 Boudet et al.
6,252,135 B1    6/2001 Chiang et al.

FOREIGN PATENT DOCUMENTS

WO     WO 99/31243    *  6/1999

OTHER PUBLICATIONS

Hu et al., Nature Biotechnology, 1999, 17:808–812.*
Franke R. et al., Plant Journal 2002, vol. 30, No. 1; pp. 33–45.*
Siminszky B. et al. PNAS, Feb. 1999, vol. 96, pp. 1750–1755.*
Ruegger, M., et al., "Regulation of Ferulate–5–Hydroxylase Expression in *Arabidopsis* in the Context of Sinapate Ester Biosynthesis," Plant Physiology, Jan., 1999, 119:101–110.
Schoch, G., et al., "CYP98A3 from *Arabidopsis thaliana* is a 3'–hydroxylase of phenolic esters, a missing link in the phenylpropanoid pathway," J. Biol. Chem., Sep. 28, 2001, 276(39):36566–74 (manuscript attached, total of 39 pages).

* cited by examiner

*Primary Examiner*—Phuong T. Bui
*Assistant Examiner*—Russell Kallis
(74) *Attorney, Agent, or Firm*—Jondle & Associates P.C.

(57) ABSTRACT

The present invention is directed to a method for altering secondary metabolism in plants, specifically phenylpropanoid metabolism. The present invention is further directed to a mutant p-coumarate 3-hydroxylase gene, referred to herein as the ref8 gene, its protein product which can be used to prepare gene constructs and transgenic plants. The gene constructs and transgenic plants are further aspects of the present invention.

3 Claims, 13 Drawing Sheets

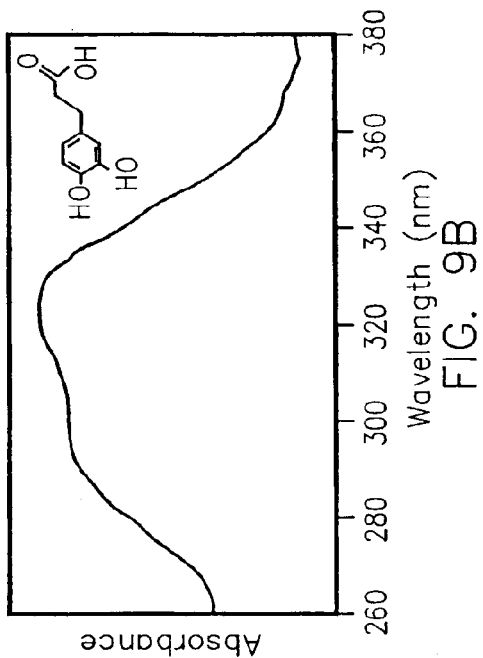
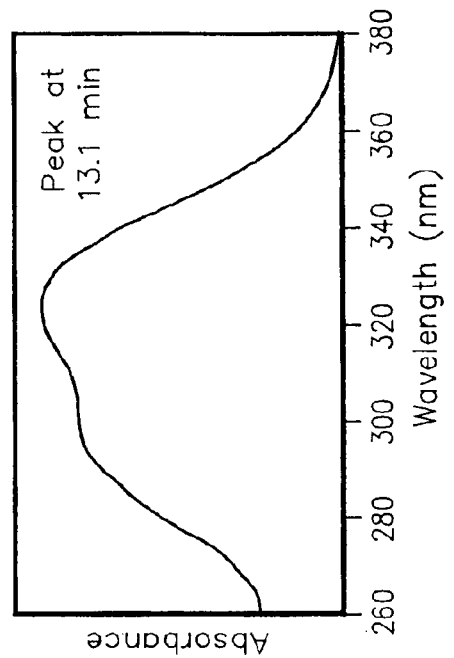
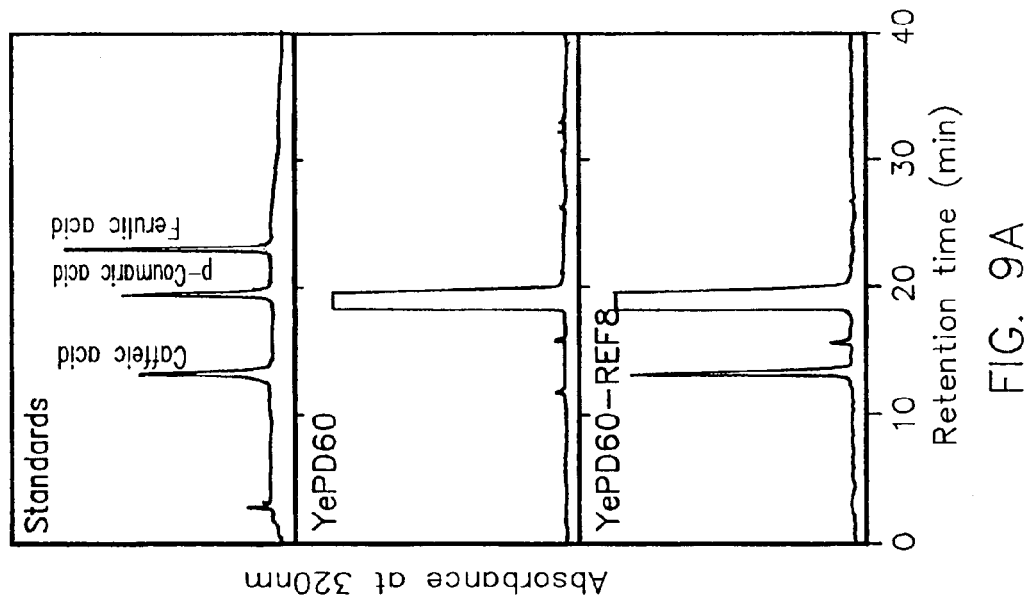

SEQUENCE LISTING

<160> NUMBER OF SEQ ID NOS: 7

<210> SEQ ID NO 1
<211> LENGTH: 1527
<212> TYPE: DNA
<213> ORGANISM: Arabidopsis thaliana

<400> SEQUENCE: 1

```
atgtcgtggt ttctaatagc ggtggcgaca atcgccgccg tcgtatccta caagctaatc    60
```

-continued

| | |
|---|---|
| caacggctaa gatacaagtt cccaccaggc ccaagcccca agccgatcgt cggtaacctc | 120 |
| tacgacataa aaccggtccg gttcagatgt tactacgagt gggctcaatc ttatggacca | 180 |
| atcatatcgg tctggatcgg ttcaattcta aacgtggtcg tatctagcgc cgagctagca | 240 |
| aaagaagttc tgaaagaaca cgaccagaaa ctcgccgacc ggcaccggaa cagatcgacg | 300 |
| gaagcattta gccgcaacgg tcaggatctt atatgggccg attatgggcc tcattacgtg | 360 |
| aaggtgagaa aagtttgcac gcttgagctc ttcacaccga aacgactcga gtctctcaga | 420 |
| cctatccgtg aagatgaagt caccgccatg gttgaatccg tcttcagaga ctgtaacctt | 480 |
| cctgaaaaca gagcaaaagg tttacaactg aggaagtact taggagcggt tgcgttcaac | 540 |
| aacataacgc ggctagcctt tgggaagcgt tttatgaacg ctgaaggtgt tgtggacgag | 600 |
| caagggcttg agttcaaggc catagtatcc aacggtctga agctaggtgc ttcactgtca | 660 |
| atagctgaac acatcccgtg gctcaggtgg atgtttccgg ctgatgagaa ggcgtttgct | 720 |
| gagcacgggg ctcgtcgtga ccgcctcact cgagctatca tggaggagca tactttggcc | 780 |
| cgtcaaaagt ctagtggagc gaaacagcat ttcgttgatg cgttgctaac gttgaaggat | 840 |
| cagtatgatc ttagtgagga tactatcatt ggtcttctat gggatatgat cacggcaggg | 900 |
| atggacacga cagcgataac agcggaatgg gcgatggcgg aaatgatcaa gaatccaaga | 960 |
| gtgcaacaaa aagtgcaaga agagttcgac agagtggttg gacttgaccg gatcttaacc | 1020 |
| gaggcagatt tctcccgctt accttacttg caatgcgtgg tgaaagagtc attcaggctg | 1080 |
| catcctccaa cgcctctaat gctacctcac cgaagcaacg cagatgtcaa gatcggaggc | 1140 |
| tatgatattc ccaaaggatc aaacgttcat gtgaatgtgt gggctgtggc tagagacccg | 1200 |
| gctgtatgga aaaatccatt tgagtttaga ccagagagat tcttggaaga agatgttgac | 1260 |
| atgaagggtc atgattttag gctgcttccg tttggagctg aagacgggt ttgtcccggt | 1320 |
| gcacaacttg gtatcaattt ggtaacttcg atgatgagtc atttgcttca ccattttgtt | 1380 |
| tggacacctc ctcaagggac taaaccggag gagattgaca tgtctgaaaa ccctggactc | 1440 |
| gttacttaca tgcgtacccc tgtgcaagcg gttgcaacgc ctcggttgcc ttcggatctg | 1500 |
| tacaaacgcg tgccttacga tatgtaa | 1527 |

<210> SEQ ID NO 2
<211> LENGTH: 1527
<212> TYPE: DNA
<213> ORGANISM: Arabidopsis thaliana

<400> SEQUENCE: 2

| | |
|---|---|
| atgtcgtggt ttctaatagc ggtggcgaca atcgccgccg tcgtatccta caagctaatc | 60 |
| caacggctaa gatacaagtt cccaccaggc ccaagcccca agccgatcgt cggtaacctc | 120 |
| tacgacataa aaccggtccg gttcagatgt tactacgagt gggctcaatc ttatggacca | 180 |
| atcatatcgg tctggatcgg ttcaattcta aacgtggtcg tatctagcgc cgagctagca | 240 |
| aaagaagttc tgaaagaaca cgaccagaaa ctcgccgacc ggcaccggaa cagatcgacg | 300 |
| gaagcattta gccgcaacgg tcaggatctt atatgggccg attatgggcc tcattacgtg | 360 |
| aaggtgagaa aagtttgcac gcttgagctc ttcacaccga aacgactcga gtctctcaga | 420 |
| cctatccgtg aagatgaagt caccgccatg gttgaatccg tcttcagaga ctgtaacctt | 480 |
| cctgaaaaca gagcaaaagg tttacaactg aggaagtact taggagcggt tgcgttcaac | 540 |
| aacataacgc ggctagcctt tgggaagcgt tttatgaacg ctgaaggtgt tgtggacgag | 600 |

```
caagggcttg agttcaaggc catagtatcc aacggtctga agctaggtgc ttcactgtca        660
atagctgaac acatcccgtg gctcaggtgg atgtttccgg ctgatgagaa ggcgtttgct        720
gagcacgggg ctcgtcgtga ccgcctcact cgagctatca tggaggagca tactttggcc        780
cgtcaaaagt ctagtggagc gaaacagcat tcgttgatg cgttgctaac gttgaaggat         840
cagtatgatc ttagtgagga tactatcatt ggtcttctat gggatatgat cacggcaggg        900
atggacacga cagcgataac agcggaatgg gcgatggcgg aaatgatcaa gaatccaaga        960
gtgcaacaaa aagtgcaaga agagttcgac agagtggttg gacttgaccg gatcttaacc       1020
gaggcagatt tctcccgctt accttacttg caatgcgtgg tgaaagagtc attcaggctg       1080
catcctccaa cgcctctaat gctacctcac cgaagcaacg cagatgtcaa gatcggaggc       1140
tatgatattc ccaaaggatc aaacgttcat gtgaatgtgt gggctgtggc tagagacccg       1200
gctgtatgga aaaatccatt tgagtttaga ccagagagat tcttggaaga agatgttgac       1260
atgaagggtc atgattttag gctgcttccg tttggagctg gaagacgggt ttgtcccggt       1320
gcacaacttg atatcaattt ggtaacttcg atgatgagtc atttgcttca ccattttgtt       1380
tggacacctc ctcaagggac taaaccggag gagattgaca tgtctgaaaa ccctggactc       1440
gttacttaca tgcgtacccc tgtgcaagcg gttgcaacgc ctcggttgcc ttcggatctg       1500
tacaaacgcg tgccttacga tatgtaa                                            1527

<210> SEQ ID NO 3
<211> LENGTH: 1549
<212> TYPE: DNA
<213> ORGANISM: Arabidopsis thaliana

<400> SEQUENCE: 3
gcaaggatcc atgtcgtggt ttctaatagc ggtggcgaca atcgccgccg tcgtatccta         60
caagctaatc caacggctaa gatacaagtt cccaccaggc ccaagcccca agccgatcgt        120 cggtaaccte tacgacataa aaccggtccg gttcagatgt tactacgagt gggctcaatc        180
ttatggacca atcatatcgg tctggatcgg ttcaattcta aacgtggtcg tatctagcgc        240
cgagctagca aaagaagttc tgaaagaaca cgaccagaaa ctcgccgacc ggcaccggaa        300
cagatcgacg gaagcattta gccgcaacgg tcaggatctt atatgggccg attatgggcc        360
tcattacgtg aaggtgagaa aagtttgcac gcttgagctc ttcacaccga aacgactcga        420
gtctctcaga cctatccgtg aagatgaagt caccgccatg gttgaatccg tcttcagaga        480
ctgtaacctt cctgaaaaca gagcaaaagg tttacaactg aggaagtact taggagcggt        540
tgcgttcaac aacataacgc ggctagcctt tgggaagcgt tttatgaacg ctgaaggtgt        600
tgtggacgag caagggcttg agttcaaggc catagtatcc aacggtctga agctaggtgc        660
ttcactgtca atagctgaac acatcccgtg gctcaggtgg atgtttccgg ctgatgagaa        720
ggcgtttgct gagcacgggg ctcgtcgtga ccgcctcact cgagctatca tggaggagca        780
tactttggcc cgtcaaaagt ctagtggagc gaaacagcat tcgttgatg cgttgctaac         840 gttgaaggat cagtatgatc ttagtgagga tactatcatt ggtcttctat gggatatgat        900
cacggcaggg atggacacga cagcgataac agcggaatgg gcgatggcgg aaatgatcaa        960
gaatccaaga gtgcaacaaa aagtgcaaga agagttcgac agagtggttg gacttgaccg       1020
gatcttaacc gaggcagatt tctcccgctt accttacttg caatgcgtgg tgaaagagtc       1080
attcaggctg catcctccaa cgcctctaat gctacctcac cgaagcaacg cagatgtcaa       1140
gatcggaggc tatgatattc ccaaaggatc aaacgttcat gtgaatgtgt gggctgtggc       1200
```

```
tagagacccg gctgtatgga aaaatccatt tgagtttaga ccagagagat tcttggaaga    1260
agatgttgac atgaagggtc atgattttag gctgcttccg tttggagctg aagacgggt     1320 ttgtcccggt gcacaacttg gtatcaattt ggtaacttcg atgatgagtc atttgcttca    1380 ccatttttgtt tggacacctc ctcaagggac taaaccggag gagattgaca tgtctgaaaa   1440
ccctggactc gttacttaca tgcgtacccc tgtgcaagcg gttgcaacgc ctcggttgcc    1500
ttcggatctg tacaaacgcg tgccttacga tatgtaaatg aattcctga               1549
```

<210> SEQ ID NO 4
<211> LENGTH: 508
<212> TYPE: PRT
<213> ORGANISM: Arabidopsis thaliana

<400> SEQUENCE: 4

```
Met Ser Trp Phe Leu Ile Ala Val Ala Thr Ile Ala Ala Val Val Ser
1               5                   10                  15

Tyr Lys Leu Ile Gln Arg Leu Arg Tyr Lys Phe Pro Pro Gly Pro Ser
            20                  25                  30

Pro Lys Pro Ile Val Gly Asn Leu Tyr Asp Ile Lys Pro Val Arg Phe
        35                  40                  45

Arg Cys Tyr Tyr Glu Trp Ala Gln Ser Tyr Gly Pro Ile Ile Ser Val
    50                  55                  60

Trp Ile Gly Ser Ile Leu Asn Val Val Ser Ser Ala Glu Leu Ala
65                  70                  75                  80

Lys Glu Val Leu Lys Glu His Asp Gln Lys Leu Ala Asp Arg His Arg
                85                  90                  95

Asn Arg Ser Thr Glu Ala Phe Ser Arg Asn Gly Gln Asp Leu Ile Trp
            100                 105                 110

Ala Asp Tyr Gly Pro His Tyr Val Lys Val Arg Lys Val Cys Thr Leu
        115                 120                 125

Glu Leu Phe Thr Pro Lys Arg Leu Glu Ser Leu Arg Pro Ile Arg Glu
    130                 135                 140

Asp Glu Val Thr Ala Met Val Glu Ser Val Phe Arg Asp Cys Asn Leu
145                 150                 155                 160

Pro Glu Asn Arg Ala Lys Gly Leu Gln Leu Arg Lys Tyr Leu Gly Ala
                165                 170                 175

Val Ala Phe Asn Asn Ile Thr Arg Leu Ala Phe Gly Lys Arg Phe Met
            180                 185                 190

Asn Ala Glu Gly Val Val Asp Glu Gln Gly Leu Glu Phe Lys Ala Ile
        195                 200                 205

Val Ser Asn Gly Leu Lys Leu Gly Ala Ser Leu Ser Ile Ala Glu His
    210                 215                 220

Ile Pro Trp Leu Arg Trp Met Phe Pro Ala Asp Glu Lys Ala Phe Ala
225                 230                 235                 240

Glu His Gly Ala Arg Arg Asp Arg Leu Thr Arg Ala Ile Met Glu Glu
                245                 250                 255

His Thr Leu Ala Arg Gln Lys Ser Ser Gly Ala Lys Gln His Phe Val
            260                 265                 270

Asp Ala Leu Leu Thr Leu Lys Asp Gln Tyr Asp Leu Ser Glu Asp Thr
        275                 280                 285

Ile Ile Gly Leu Leu Trp Asp Met Ile Thr Ala Gly Met Asp Thr Thr
    290                 295                 300

Ala Ile Thr Ala Glu Trp Ala Met Ala Glu Met Ile Lys Asn Pro Arg
```

```
            305                 310                 315                 320
Val Gln Gln Lys Val Gln Glu Glu Phe Asp Arg Val Val Gly Leu Asp
                325                 330                 335

Arg Ile Leu Thr Glu Ala Asp Phe Ser Arg Leu Pro Tyr Leu Gln Cys
            340                 345                 350

Val Val Lys Glu Ser Phe Arg Leu His Pro Pro Thr Pro Leu Met Leu
            355                 360                 365

Pro His Arg Ser Asn Ala Asp Val Lys Ile Gly Gly Tyr Asp Ile Pro
        370                 375                 380

Lys Gly Ser Asn Val His Val Asn Val Trp Ala Val Ala Arg Asp Pro
385                 390                 395                 400

Ala Val Trp Lys Asn Pro Phe Glu Phe Arg Pro Glu Arg Phe Leu Glu
                405                 410                 415

Glu Asp Val Asp Met Lys Gly His Asp Phe Arg Leu Leu Pro Phe Gly
            420                 425                 430

Ala Gly Arg Arg Val Cys Pro Gly Ala Gln Leu Gly Ile Asn Leu Val
        435                 440                 445

Thr Ser Met Met Ser His Leu Leu His His Phe Val Trp Thr Pro Pro
450                 455                 460

Gln Gly Thr Lys Pro Glu Ile Asp Met Ser Glu Asn Pro Gly Leu
465                 470                 475                 480

Val Thr Tyr Met Arg Thr Pro Val Gln Ala Val Ala Thr Pro Arg Leu
                485                 490                 495

Pro Ser Asp Leu Tyr Lys Arg Val Pro Tyr Asp Met
            500                 505

<210> SEQ ID NO 5
<211> LENGTH: 508
<212> TYPE: PRT
<213> ORGANISM: Arabidopsis thaliana

<400> SEQUENCE: 5

Met Ser Trp Phe Leu Ile Ala Val Ala Thr Ile Ala Ala Val Val Ser
1               5                   10                  15

Tyr Lys Leu Ile Gln Arg Leu Arg Tyr Lys Phe Pro Pro Gly Pro Ser
            20                  25                  30

Pro Lys Pro Ile Val Gly Asn Leu Tyr Asp Ile Lys Pro Val Arg Phe
        35                  40                  45

Arg Cys Tyr Tyr Glu Trp Ala Gln Ser Tyr Gly Pro Ile Ile Ser Val
    50                  55                  60

Trp Ile Gly Ser Ile Leu Asn Val Val Ser Ser Ala Glu Leu Ala
65                  70                  75                  80

Lys Glu Val Leu Lys Glu His Asp Gln Lys Leu Ala Asp Arg His Arg
                85                  90                  95

Asn Arg Ser Thr Glu Ala Phe Ser Arg Asn Gly Gln Asp Leu Ile Trp
            100                 105                 110

Ala Asp Tyr Gly Pro His Tyr Val Lys Val Arg Lys Val Cys Thr Leu
        115                 120                 125

Glu Leu Phe Thr Pro Lys Arg Leu Glu Ser Leu Arg Pro Ile Arg Glu
    130                 135                 140

Asp Glu Val Thr Ala Met Val Glu Ser Val Phe Arg Asp Cys Asn Leu
145                 150                 155                 160

Pro Glu Asn Arg Ala Lys Gly Leu Gln Leu Arg Lys Tyr Leu Gly Ala
                165                 170                 175
```

-continued

```
Val Ala Phe Asn Asn Ile Thr Arg Leu Ala Phe Gly Lys Arg Phe Met
                180                 185                 190

Asn Ala Glu Gly Val Val Asp Glu Gln Gly Leu Glu Phe Lys Ala Ile
            195                 200                 205

Val Ser Asn Gly Leu Lys Leu Gly Ala Ser Leu Ser Ile Ala Glu His
210                 215                 220

Ile Pro Trp Leu Arg Trp Met Phe Pro Ala Asp Glu Lys Ala Phe Ala
225                 230                 235                 240

Glu His Gly Ala Arg Arg Asp Arg Leu Thr Arg Ala Ile Met Glu Glu
                245                 250                 255

His Thr Leu Ala Arg Gln Lys Ser Ser Gly Ala Lys Gln His Phe Val
            260                 265                 270

Asp Ala Leu Leu Thr Leu Lys Asp Gln Tyr Asp Leu Ser Glu Asp Thr
        275                 280                 285

Ile Ile Gly Leu Leu Trp Asp Met Ile Thr Ala Gly Met Asp Thr Thr
    290                 295                 300

Ala Ile Thr Ala Glu Trp Ala Met Ala Glu Met Ile Lys Asn Pro Arg
305                 310                 315                 320

Val Gln Gln Lys Val Gln Glu Glu Phe Asp Arg Val Val Gly Leu Asp
                325                 330                 335

Arg Ile Leu Thr Glu Ala Asp Phe Ser Arg Leu Pro Tyr Leu Gln Cys
            340                 345                 350

Val Val Lys Glu Ser Phe Arg Leu His Pro Pro Thr Pro Leu Met Leu
        355                 360                 365

Pro His Arg Ser Asn Ala Asp Val Lys Ile Gly Gly Tyr Asp Ile Pro
    370                 375                 380

Lys Gly Ser Asn Val His Val Asn Val Trp Ala Val Ala Arg Asp Pro
385                 390                 395                 400

Ala Val Trp Lys Asn Pro Phe Glu Phe Arg Pro Glu Arg Phe Leu Glu
                405                 410                 415

Glu Asp Val Asp Met Lys Gly His Asp Phe Arg Leu Leu Pro Phe Gly
            420                 425                 430

Ala Gly Arg Arg Val Cys Pro Gly Ala Gln Leu Asp Ile Asn Leu Val
        435                 440                 445

Thr Ser Met Met Ser His Leu Leu His His Phe Val Trp Thr Pro Pro
    450                 455                 460

Gln Gly Thr Lys Pro Glu Glu Ile Asp Met Ser Glu Asn Pro Gly Leu
465                 470                 475                 480

Val Thr Tyr Met Arg Thr Pro Val Gln Ala Val Ala Thr Pro Arg Leu
                485                 490                 495

Pro Ser Asp Leu Tyr Lys Arg Val Pro Tyr Asp Met
            500                 505

<210> SEQ ID NO 6
<211> LENGTH: 477
<212> TYPE: PRT
<213> ORGANISM: Arabidopsis thaliana

<400> SEQUENCE: 6

Ser Pro Lys Pro Ile Val Gly Asn Leu Tyr Asp Ile Lys Pro Val Arg
1               5                   10                  15

Phe Arg Cys Tyr Tyr Glu Trp Ala Gln Ser Tyr Gly Pro Ile Ile Ser
                20                  25                  30

Val Trp Ile Gly Ser Ile Leu Asn Val Val Ser Ser Ala Glu Leu
            35                  40                  45
```

-continued

```
Ala Lys Glu Val Leu Lys Glu His Asp Gln Lys Leu Ala Asp Arg His
         50                  55                  60
Arg Asn Arg Ser Thr Glu Ala Phe Ser Arg Asn Gly Gln Asp Leu Ile
 65                  70                  75                  80
Trp Ala Asp Tyr Gly Pro His Tyr Val Lys Val Arg Lys Val Cys Thr
                     85                  90                  95
Leu Glu Leu Phe Thr Pro Lys Arg Leu Glu Ser Leu Arg Pro Ile Arg
                100                 105                 110
Glu Asp Glu Val Thr Ala Met Val Glu Ser Val Phe Arg Asp Cys Asn
            115                 120                 125
Leu Pro Glu Asn Arg Ala Lys Gly Leu Gln Leu Arg Lys Tyr Leu Gly
        130                 135                 140
Ala Val Ala Phe Asn Asn Ile Thr Arg Leu Ala Phe Gly Lys Arg Phe
145                 150                 155                 160
Met Asn Ala Glu Gly Val Val Asp Glu Gln Gly Leu Glu Phe Lys Ala
                    165                 170                 175
Ile Val Ser Asn Gly Leu Lys Leu Gly Ala Ser Leu Ser Ile Ala Glu
                180                 185                 190
His Ile Pro Trp Leu Arg Trp Met Phe Pro Ala Asp Glu Lys Ala Phe
            195                 200                 205
Ala Glu His Gly Ala Arg Arg Asp Arg Leu Thr Arg Ala Ile Met Glu
        210                 215                 220
Glu His Thr Leu Ala Arg Gln Lys Ser Ser Gly Ala Lys Gln His Phe
225                 230                 235                 240
Val Asp Ala Leu Leu Thr Leu Lys Asp Gln Tyr Asp Leu Ser Glu Asp
                    245                 250                 255
Thr Ile Ile Gly Leu Leu Trp Asp Met Ile Thr Ala Gly Met Asp Thr
                260                 265                 270
Thr Ala Ile Thr Ala Glu Trp Ala Met Ala Glu Met Ile Lys Asn Pro
            275                 280                 285
Arg Val Gln Gln Lys Val Gln Glu Glu Phe Asp Arg Val Val Gly Leu
        290                 295                 300
Asp Arg Ile Leu Thr Glu Ala Asp Phe Ser Arg Leu Pro Tyr Leu Gln
305                 310                 315                 320
Cys Val Val Lys Glu Ser Phe Arg Leu His Pro Pro Thr Pro Leu Met
                    325                 330                 335
Leu Pro His Arg Ser Asn Ala Asp Val Lys Ile Gly Gly Tyr Asp Ile
                340                 345                 350
Pro Lys Gly Ser Asn Val His Val Asn Val Trp Ala Val Ala Arg Asp
            355                 360                 365
Pro Ala Val Trp Lys Asn Pro Phe Glu Phe Arg Pro Glu Arg Phe Leu
        370                 375                 380
Glu Glu Asp Val Asp Met Lys Gly His Asp Phe Arg Leu Leu Pro Phe
385                 390                 395                 400
Gly Ala Gly Arg Arg Val Cys Pro Gly Ala Gln Leu Gly Ile Asn Leu
                    405                 410                 415
Val Thr Ser Met Met Ser His Leu Leu His His Phe Val Trp Thr Pro
                420                 425                 430
Pro Gln Gly Thr Lys Pro Glu Glu Ile Asp Met Ser Glu Asn Pro Gly
            435                 440                 445
Leu Val Thr Tyr Met Arg Thr Pro Val Gln Ala Val Ala Thr Pro Arg
        450                 455                 460
```

```
Leu Pro Ser Asp Leu Tyr Lys Arg Val Pro Tyr Asp Met
465                 470                 475
```

<210> SEQ ID NO 7
<211> LENGTH: 477
<212> TYPE: PRT
<213> ORGANISM: Arabidopsis thaliana

<400> SEQUENCE: 7

```
Ser Pro Lys Pro Ile Val Gly Asn Leu Tyr Asp Ile Lys Pro Val Arg
1               5                   10                  15

Phe Arg Cys Tyr Tyr Glu Trp Ala Gln Ser Tyr Gly Pro Ile Ile Ser
            20                  25                  30

Val Trp Ile Gly Ser Ile Leu Asn Val Val Ser Ser Ala Glu Leu
        35                  40                  45

Ala Lys Glu Val Leu Lys Glu His Asp Gln Lys Leu Ala Asp Arg His
50                  55                  60

Arg Asn Arg Ser Thr Glu Ala Phe Ser Arg Asn Gly Gln Asp Leu Ile
65                  70                  75                  80

Trp Ala Asp Tyr Gly Pro His Tyr Val Lys Val Arg Lys Val Cys Thr
                85                  90                  95

Leu Glu Leu Phe Thr Pro Lys Arg Leu Glu Ser Leu Arg Pro Ile Arg
            100                 105                 110

Glu Asp Glu Val Thr Ala Met Val Glu Ser Val Phe Arg Asp Cys Asn
        115                 120                 125

Leu Pro Glu Asn Arg Ala Lys Gly Leu Gln Leu Arg Lys Tyr Leu Gly
130                 135                 140

Ala Val Ala Phe Asn Asn Ile Thr Arg Leu Ala Phe Gly Lys Arg Phe
145                 150                 155                 160

Met Asn Ala Glu Gly Val Val Asp Glu Gln Gly Leu Glu Phe Lys Ala
                165                 170                 175

Ile Val Ser Asn Gly Leu Lys Leu Gly Ala Ser Leu Ser Ile Ala Glu
            180                 185                 190

His Ile Pro Trp Leu Arg Trp Met Phe Pro Ala Asp Glu Lys Ala Phe
        195                 200                 205

Ala Glu His Gly Ala Arg Arg Asp Arg Leu Thr Arg Ala Ile Met Glu
210                 215                 220

Glu His Thr Leu Ala Arg Gln Lys Ser Ser Gly Ala Lys Gln His Phe
225                 230                 235                 240

Val Asp Ala Leu Leu Thr Leu Lys Asp Gln Tyr Asp Leu Ser Glu Asp
                245                 250                 255

Thr Ile Ile Gly Leu Leu Trp Asp Met Ile Thr Ala Gly Met Asp Thr
            260                 265                 270

Thr Ala Ile Thr Ala Glu Trp Ala Met Ala Glu Met Ile Lys Asn Pro
        275                 280                 285

Arg Val Gln Gln Lys Val Gln Glu Glu Phe Asp Arg Val Val Gly Leu
290                 295                 300

Asp Arg Ile Leu Thr Glu Ala Asp Phe Ser Arg Leu Pro Tyr Leu Gln
305                 310                 315                 320

Cys Val Val Lys Glu Ser Phe Arg Leu His Pro Pro Thr Pro Leu Met
                325                 330                 335

Leu Pro His Arg Ser Asn Ala Asp Val Lys Ile Gly Gly Tyr Asp Ile
            340                 345                 350

Pro Lys Gly Ser Asn Val His Val Asn Val Trp Ala Val Ala Arg Asp
        355                 360                 365
```

-continued

```
Pro Ala Val Trp Lys Asn Pro Phe Glu Phe Arg Pro Glu Arg Phe Leu
    370                 375                 380

Glu Glu Asp Val Asp Met Lys Gly His Asp Phe Arg Leu Leu Pro Phe
385                 390                 395                 400

Gly Ala Gly Arg Arg Val Cys Pro Gly Ala Gln Leu Asp Ile Asn Leu
                405                 410                 415

Val Thr Ser Met Met Ser His Leu Leu His His Phe Val Trp Thr Pro
                420                 425                 430

Pro Gln Gly Thr Lys Pro Glu Glu Ile Asp Met Ser Glu Asn Pro Gly
            435                 440                 445

Leu Val Thr Tyr Met Arg Thr Pro Val Gln Ala Val Ala Thr Pro Arg
    450                 455                 460

Leu Pro Ser Asp Leu Tyr Lys Arg Val Pro Tyr Asp Met
465                 470                 475
```

GENES ENCODING P-COUMARATE 3-HYDROXYLASE (C3H) AND METHODS OF USE

This application claims benefit under 35 U.S.C. § 119(e) of Provisional Patent Application Ser. No. 60/225,554, filed Aug. 16, 2000, incorporated herein by reference.

This invention was made with government support under United States Department of Energy grant number DEFG 0294ER20138 and National Service Foundation grant number 0095075IBN. The U.S. Government has certain rights in this invention.

BACKGROUND

The present invention is directed to methods to alter secondary metabolism of a plant, more specifically phenylpropanoid metabolism. The present invention is also directed to novel mutant polynucleotide molecules, referred to as ref8, that encode an *Arabidopsis* p-coumarate 3-hydroxylase having altered biological activity. The present invention is also directed to uses of the novel nucleotide sequences set forth herein, including their use in vectors and other DNA constructs for transforming plants and microorganisms. The DNA constructs and transgenic plants are further aspects of the present invention.

The publications, patents and other materials used herein to illuminate the background of the invention, and in particular cases, to provide additional details respecting the practice, are incorporated by reference, and for convenience are referenced in the following text by author and date and are listed alphabetically by author in the appended bibliography.

By way of background, C3H is an enzyme of the phenylpropanoid pathway. Phenylpropanoid compounds have a wide array of important functions in plants. They serve in the interaction of plants with their biotic and abiotic environments, mediate certain aspects of plant growth and development, and are important structural components of the plant secondary cell wall. For example, stilbenes and isoflavones are important phytoalexins in plants (Nicholson and Hammerschmidt, 1992). In maize and petunia, flavonoids have been shown to be necessary for pollen viability (Coe et al., 1981; Taylor and Jorgensen, 1992; van der Meer et al., 1992), and have been suggested to be endogenous modulators of auxin transport (Mathesius et al., 1998). Hydroxycinnamic acids lead to the synthesis of UV-sunscreens in plants (Landry et al., 1995), and are also precursors for lignin (Lewis and Yamomoto, 1990). Simpler phenylpropanoid-derived molecules such as acetosyringone act as signaling molecules in the interaction of plants with *Agrobacterium* (Stachel et al., 1985). Lignan glycosides known as dihydrodiconiferyl glycosides (DCGs) have cytokinin-like activity in plants (Binns et al., 1987; Lynn et al., 1987; Teutonico et al., 1991; Orr and Lynn, 1992), and may be responsible for growth abnormalities seen in some transgenic plants in which phenylpropanoid metabolism has been perturbed (Tamagnone et al., 1998). Phenylpropanoids are also increasingly being recognized as having an impact on human health. For example, isoflavones and lignans have beneficial estrogen-like activity in humans which is prompting their use as neutraceuticals (Bingham et al., 1998) and the stilbene resveratrol is thought to provide the health benefits associated with moderate wine consumption (Jang et al., 1997). All of the above examples make a compelling argument for improving our understanding of phenylpropanoid metabolism and its regulation.

Advances in biotechnology have provided the tools with which to manipulate phenylpropanoid metabolism, and a number of cases have illustrated the potential value of this approach. The capacity to synthesize resveratrol has been transferred to tobacco by transformation with a construct encoding stilbene synthase (Hain et al., 1993). Flower pigmentation has been successfully manipulated in petunia by introduction of the maize gene encoding dihydroflavonol reductase (Meyer et al., 1987). Similarly, novel and valuable varieties of cut flowers are being generated by introduction of the gene encoding flavonoid 3',5'-hydroxylase which leads to the accumulation of blue trihydroxy-substituted anthocyanins (Holton et al., 1993). The manipulation of lignin biosynthesis has also been extensively investigated, with results ranging from substantial decreases in total lignin content to dramatic changes in lignin monomer composition (Meyer et al., 1998). As additional targets for the metabolic engineering of phenylpropanoid metabolism are investigated, their manipulations may lead to plants with enhanced nutritional value, crops that synthesize large amounts of secondary metabolites for industrial use, the modification of lignin quality and quantity in plants, and plants with enhanced UV tolerance. For these approaches to be successful, it is essential that we have a thorough knowledge of all of the catalysts involved.

Most of the genes encoding the enzymes of the phenylpropanoid pathway have been cloned over the last ten years by standard biochemical approaches, and since their original isolation, an array of orthologues have been cloned from various species. These include the genes encoding caffeoyl CoA O-methyltransferase (CCoAOMT), cinnamate 4-hydroxylase (C4H), cinnamyl alcohol dehydrogenase (CAD), cinnamoyl CoA reductase (CCR), 4-(hydroxy) cinnamoyl CoA ligase (4CL), phenylalanine ammonia-lyase (PAL), and caffeic acid/5-hydroxyferulic acid O-methyltransferase (COMT). The two cytochrome P450-dependent monooxygenases (P450s) in the pathway, C4H and ferulate 5-hydroxylase (F5H) were more difficult targets because the instability, low abundance, and membrane-bound nature of plant P450s makes conventional purification problematic. Despite these difficulties, the gene encoding C4H was recently identified (Mizutani et al., 1993b; Teutsch et al., 1993) following purification of the enzyme (Gabriac et al., 1991; Mizutani et al., 1993a). Because the activity of F5H had been detected only once in plant extracts (Grand, 1984), and because F5H proved unstable to purification, the detailed characterization of F5H was made possible only through the genetic analysis of the *Arabidopsis* fah1 mutant (Chapple et al., 1992). Using this mutant, the gene encoding F5H was cloned by T-DNA tagging, an approach that circumvented the requirement of protein purification (Meyer et al., 1996).

The biosynthesis of many phenylpropanoids requires two distinct hydroxylation steps. C4H introduces the first hydroxyl group at the 4-position of the aromatic ring of cinnamic acid. C4H activity is readily measured in plants, and was one of the first plant enzymes to be recognized to be a P450. The next hydroxylation occurs at the 3-position of the ring, and is necessary for the synthesis of many important phenylpropanoid compounds. In contrast to C4H, the 3-hydroxylase of the phenylpropanoid pathway has not been fully characterized. The enzyme that catalyzes this reaction is known as p-coumarate 3-hydroxylase (C3H), although this hydroxylation may also be carried out at the CoA thioester level by p-coumaroyl CoA 3-hydroxylase (pCCoA3H). It is not clear which of these two activities is relevant to phenylpropanoid metabolism because the 3-hydroxylase is an enigmatic enzyme. It has eluded attempts over the last thirty years to unambiguously characterize it in detail at the enzymatic level. It was the last gene of the phenylpropanoid pathway to be cloned.

Over the past thirty years, many researchers have attempted to assay, characterize and purify C3H. C3H activity has been detected in extracts of spinach beet, sorghum, oak, mung bean, and potato (Vaughan and Butt, 1969; Vaughan and Butt, 1970; Alibert et al., 1972; Bartlett et al., 1972; Stafford and Dresler, 1972; Halliwell, 1975; Duke and Vaughn, 1982; Bolwell and Butt, 1983; Boniwell and Butt, 1986; Kojima and Takeuchi, 1989). C3H has been characterized as a copper-containing mixed function oxidase (Vaughan and Butt, 1970) that requires an electron donor for activity. In most cases ascorbate has been found to be the optimal donor, although it is often required in very high concentration with $K_m$ values as high as 10 mM (Kojima and Takeuchi, 1989). NADPH and 2-amino-4-hydroxy-6,7-dimethylpteridine also served as a reductant in some cases (Vaughan and Butt, 1970; Stafford and Dresler, 1972), whereas other enzyme preparations showed an absolute requirement for FAD or FMN (Boniwell and Butt, 1986). C3H has been reported to be associated with the chloroplast thylakoid membranes, where it was suggested that plastoquinone or ferredoxin could serve as the electron donor in vivo (Bartlett et al., 1972).

In most experiments, C3H activity was associated with a phenolase activity which oxidizes dihydroxyphenols to their corresponding orthoquinones. In some cases, C3H activity could be purified away from phenolases, but generally the semi-purified C3H preparations retained substantial ability to oxidize dihydroxyphenols (Stafford and Dressler, 1972). Still other experiments were aimed at correlating light- and wound-induced increases in PAL and C4H with induction of putative C3H activities (Bolwell and Butt, 1983). Once high background levels of phenolase were accounted for, some increases in C3H activity could be identified, and although the corresponding protein was partially purified it was not studied further. In experiments using mung bean seedlings treated with the fungal toxin tentoxin, phenolase activity was completely eliminated while the accumulation of caffeic acid in vivo and in vitro remained unaffected. These experiments provided strong evidence that distinguished C3H from phenolase (Duke and Vaughn, 1982).

Other research has suggested that the 3-hydroxylation reaction occurs at the level of p-coumaroyl esters such as p-coumaroyl quinate, p-coumaroyl shikimate, or p-coumaroyl glucose (Heller and Kühnl, 1985; Kühnl et al., 1987; Tanaka and Kojima, 1991). Based upon their association with membranes and classical inhibitor studies, the first two activities were attributed to P450s. The latter enzyme appeared to be closely related to the aforementioned phenolases and its involvement in phenylpropanoid biosynthesis has been viewed skeptically by some authors (Wang et al., 1997).

Finally, another body of work suggests that 3-hydroxylation occurs at the level of the CoA thioester, and that the product of this reaction is used both as a primer for dihydroxylated anthocyanin biosynthesis, and as an acyl-donor. In *Silene dioica*, the P gene controls hydroxylation of the 3' position of the anthocyanin B ring and the substitution pattern of the acyl-moiety esterified to the anthocyanin (Kamsteeg et al., 1980). Wild-type anthocyanins are caffeic acid esters of dihydroxy-substituted cyanidin glucosides, while homozygous p mutants accumulate monohydroxylated pelarogonidin glucosides that are esterified with p-coumaric acid. In this system, the pCCoA3H activity was shown to be an NADPH-dependent monooxygenase, and this activity was shown to be absent in p/p petal extracts (Kamsteeg et al., 1981). The generality of these findings in relation to flavonoid synthesis is in doubt, however, since in other systems flavonoid hydroxylation occurs at the dihydroflavonol level and is catalyzed by specific P450s (Holton et al., 1993; Brugliera et al., 1999). A $Zn^{2+}$— and ascorbate-dependent pCCoA3H has also been assayed in elicitor-induced cultures of parsley cells (Kneusel et al., 1989). The activity of this enzyme was shown to be highly sensitive to pH, and this was suggested to be a mechanism for enzyme activation in response to elicitation. While the nature and identity of pCCoA3H remains questionable, the presence of CCoAOMT in plants (Pakusch et al., 1989; Schmitt et al., 1991; Ye et al., 1994; Ye and Varner, 1995), and the recent demonstration that its activity contributes substantially to lignin biosynthesis (Zhong et al., 1998) suggests that pCCoA3H activity may be relevant to phenylpropanoid metabolism.

The potential success or failure of metabolic engineering efforts hinge upon a thorough understanding of the target pathway. Similarly, the ability to interpret data from experiments that examine plant responses to pathogen or herbivore attack depends upon a comprehensive understanding of the metabolic framework that underlies those responses. One example that is particularly relevant to this proposal can be found in the recent rewriting of the phenylpropanoid pathway that has been the unexpected outcome of experiments aimed at the modification of lignin content and composition.

The longstanding model of phenylpropanoid metabolism has postulated a branched but linear pathway (Higuchi, 1981). According to this model, the phenylpropane skeleton of phenylalanine is converted to hydroxycinnamic acids which serve as precursors for flavonoids, lignin and hydroxycinnamic acid esters. More recently, a different route for the biosynthesis of lignin monomers has received attention (Kneusel et al., 1989; Kühnl et al., 1989; Pakusch et al., 1989; Pakusch et al., 1991; Schmitt et al., 1991; Ye et al., 1994; Ye and Varner, 1995; Zhong et al., 1998). This so-called "alternative pathway" involves the activation of p-coumaric acid to its coenzyme A thioester, followed by hydroxylation and methylation reactions that ultimately generate feruloyl-CoA. Considering that ferulic acid can also be synthesized by the free acid pathway and can be activated to its CoA thioester by 4CL, lignin monomer biosynthesis probably occurs via a cross-linked network of pathways. Indeed, the continued accumulation of guaiacyl lignin in COMT suppressed plants (Atanassova et al., 1995; Van Doorsselaere et al., 1995) indicates that the alternative pathway is a major contributor to lignin biosynthesis in woody plants. This hypothesis has been tested directly by the generation of transgenic tobacco downregulated for caffeoyl-CoA O-methytransferase (CCoAOMT) activity (Zhong et al., 1998). These plants had lower total lignin content, demonstrating that the alternative pathway is a quantitatively important route for monolignol biosynthesis and that COMT activity cannot compensate for a decrease in the expression of CCoAOMT.

In addition to the incorporation of the "alternative pathway", data from the present research and that of others has necessitated a further revision of the lignin biosynthetic pathway (Humphreys, et al., 1999; Osakabe, et al., 1999). In these experiments, F5H expressed in yeast demonstrated Michaelis-Menten kinetics with regard to ferulate hydroxylation with a $K_m$ of 1 mM and a $V_{max}$ of 4 pKat $mg^{-1}$ protein. This $K_m$ was unexpectedly high considering that C4H, a P450 three steps earlier in the pathway, exhibits a 4 μM $K_m$ for its substrate (Urban et al., 1994). This inconsistency led us to test the hypothesis that phenylpropanoid pathway intermediates other than ferulate might be better substrates for F5H. Assays conducted with coniferaldehyde demonstrated that the $K_m$ and $V_{max}$ of F5H for this substrate were 1 μM and 5 pKat mg$^{-1}$ respectively, and the corresponding values for coniferyl alcohol were 3 μM and 6 pKat mg$^{-1}$. These data strongly suggest that coniferaldehyde and coniferyl alcohol are the preferred substrates for F5H, and that F5H probably acts later in the pathway than was previously envisioned. Other experiments have also suggested that COMT is actually a 5-hydroxyconiferyl alcohol/5-hydroxyconiferaldehyde O-methyltransferase that acts immediately downstream of F5H in the lignin biosynthetic pathway (Humphreys et al., 1999; Osakabe et al., 1999; Li et al., 2000).

The experiments described above, among others, have demonstrated that understanding of phenylpropanoid metabolism is still incomplete. Although plant secondary metabolism has been studied for many decades, modern molecular, biochemical, and genetic investigations have led to substantial recent revisions in conventional thinking about how the products of this pathway are synthesized. The most notable remaining gap in knowledge of the phenylpropanoid pathway is C3H.

Certain intermediates of phenylpropanoid pathway are precursors for lignin. In a parallel manner, in the last decade, our understanding of lignin biosynthesis has rapidly progressed. In many cases, the genetic manipulation of genes encoding enzymes of the conventional lignin pathway has generated unexpected results which have led the scientific community to re-evaluate lignin biosynthesis. The analysis of transgenics and mutants have demonstrated that genetically modified lignins may possess significant advantages over and above traditional raw materials currently used in the pulp and paper industry. In order to further "fine-tune" lignin profiles in economically important plant species in a rational manner, new biotechnological strategies must be employed. Thus, it is also desired to identify novel target genes in the biosynthesis of lignin by molecular and genetic approaches.

SUMMARY OF THE INVENTION

The present invention is directed to methods to alter secondary metabolism of a plant, more specifically phenylpropanoid metabolism. The present invention is also directed to novel mutant polynucleotide molecules, referred to as ref8, that encode an *Arabidopsis* p-coumarate 3-hydroxylase having altered biological activity. The present invention is also directed to uses of the novel nucleotide sequences set forth herein, including their use in vectors and other DNA constructs for transforming plants and microorganisms. The DNA constructs and transgenic plants are further aspects of the present invention.

In one aspect of the invention, sense and antisense suppression methods or virus induced gene silencing methods for producing plants having altered phenylpropanoid metabolism are provided. In one embodiment of this aspect, quantitative lignin biosynthesis is altered. In a second embodiment, qualitative lignin biosynthesis is altered. In a third embodiment, flavonoid content is increased. In a fourth embodiment, isoflavonoid content is increased. In a fifth embodiment, anthocyanin content is increased. In a sixth embodiment, cell wall bound conjugates are decreased.

In a second aspect of the invention, constructs comprising at least a portion of REF8 nucleic acid is provided for altering phenylpropanoid metabolism. The constructs generally comprise a heterologous promoter, i.e., one not naturally associated with the wild-type REF8 gene. The REF8 nucleic acid may be in the sense or antisense orientation with respect to the promoter. Vectors containing the construct for use in transforming plants or microorganisms are also provided. Any plant cells can be transformed in accordance with the present invention. Preferred plant cells are plant cells of woody plants. Preferred microorganisms are bacteria and yeast.

In a third aspect of the invention, the DNA and protein sequences are provided for ref8 gene.

In a fourth aspect of the invention, plants having at least one cell transformed with a construct containing REF8 nucleic acid for altering secondary metabolism are provided. Such plants have a phenotype characterized by altered secondary metabolism. Suitable plants may include but are not limited to alfalfa (*Medicago sp.*), rice (*Oryza sp.*), maize (*Zea mays*), oil seed rape (*Brassica sp.*), forage grasses, and also tree crops such as eucalyptus (*Eucalyptus sp.*), pine (*Pinus sp.*), spruce (*Picea sp.*) and poplar (*Populus sp.*), as well as *Arabidopsis sp.* and tobacco (*Nicotiana sp.*).

In a fifth aspect of the invention, methods are provided for the production of mutant c3 h in host cells. Preferred host cells are bacteria and yeast.

SUMMARY OF THE SEQUENCES

Figure 1A:
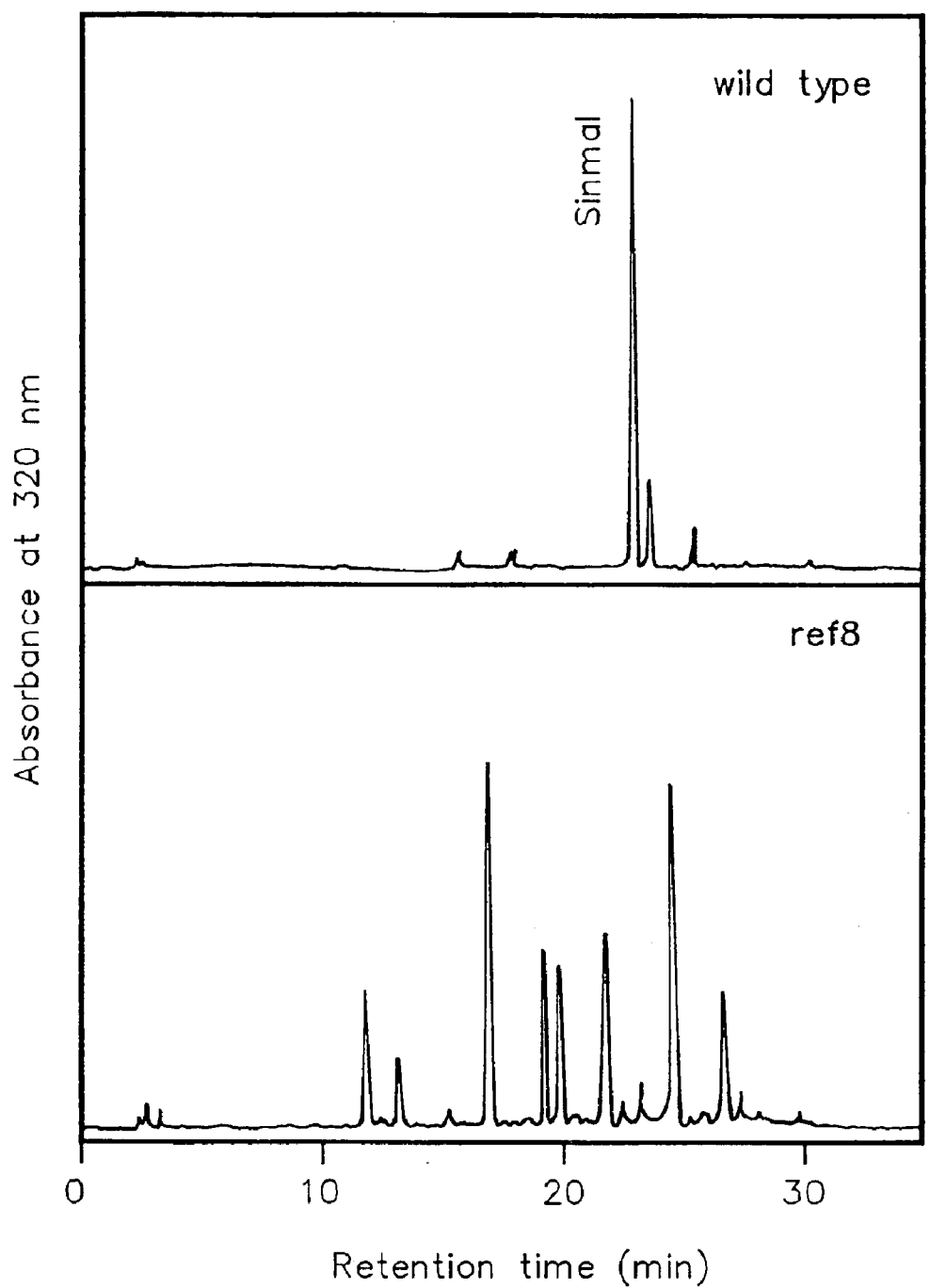
FIGS. 1A–C show HPLC analysis of soluble secondary metabolites produced by wild-type and ref8 plants. (A) Compounds found in wild-type and ref8 leaves were extracted with methanol and analyzed by HPLC. The elution of UV-absorbing compounds was monitored at 320 nm. (B) Hydroxycinnamic acids released from their ester conjugates by saponification (1 M NaOH, 16h, room temperature) of the methanolic extract of (A). pCt, trans-p-coumaric acid; pC$_c$, cis-p-coumaric acid; St, trans-sinapic acid; S$_c$, cis-sinapic acid. (C) The same analyses as (A) performed on wild-type and ref8 seed extracts. Sinmal, sinapoylmalate; Singlc, sinapoylglucose; Sincho, sinapoylcholine.

SEQ ID NO:1 is the nucleotide sequence for the coding region of the wild-type C3H gene from *Arabidopsis*.

SEQ ID NO:2 is the nucleotide sequence of the ref8 gene.

SEQ ID NO:3 is the nucleotide sequence of the gene used for expression in yeast.

SEQ ID NO:4 is the amino acid sequence encoded by SEQ ID NO:1.

SEQ ID NO:5 is the amino acid sequence encoded by SEQ ID NO:2.

SEQ ID NO:6 is the amino acid sequence of the catalytic domain of SEQ ID NO:4.

SEQ ID NO:7 is the amino acid sequence of the catalytic domain of SEQ ID NO:5.

DETAILED DESCRIPTION OF THE INVENTION

The present invention is directed to methods to alter secondary metabolism of a plant, more specifically phenylpropanoid metabolism. The present invention is also directed to novel mutant polynucleotide molecules, referred to as ref8, that encode an *Arabidopsis* p-coumarate 3-hydroxylase having altered biological activity. The present invention is also directed to uses of the novel nucleotide sequences set forth herein, including their use in vectors and other DNA constructs for transforming plants and microorganisms. The DNA constructs and transgenic plants are further aspects of the present invention.

Advances in biotechnology have provided the tools with which to manipulate phenylpropanoid metabolism, and a number of cases have illustrated the potential value of this approach. Most of the genes encoding the enzymes of the phenylpropanoid pathway have been cloned over the last three years and, since their original isolation, an array of orthologues have been cloned from various species. Despite the fact that much is known of all other enzymes in the phenylpropanoid pathway, C3H has not previously been characterized. Knowledge of the activity of C3H disclosed herein enables alteration of the phenylpropanoid pathway. Some uses of the activity of C3H polypeptides are described in more detail below.

Definitions

The present invention employs the following definitions:

"C3H" or "p-coumarate 3-hydroxylase" refers to an enzyme in the phenylpropanoid biosynthetic pathway which complements the ref8 mutant when expressed in *Arabidopsis*.

"c3 h" or "mutant C3H" each refer to the polypeptide encoded by the ref8 gene.

"ref8 gene" refers to the polynucleotide which is complemented by the wild-type C3H when expressed in *Arabidopsis*. The ref8 gene has the nucleotide sequence set forth in SEQ ID NO:2.

"Altered Lignin Content" or "modified lignin content" refers to the modification of total lignin content as measured by the method described herein or other methods known in the art.

"Altered lignin content" or "modified lignin content" refers to modification of the lignin monomer composition compared to the parent plant from which the plant having the modified phenotype is obtained. Alterations correlated with suppression of C3H polypeptide activity may include increases in percent H lignin monomers. Such modified lignin content can be uniform throughout the plant and typically arise when each of the cells within the plant contain cells transformed with a vector comprising at least a portion of the REF8 nucleic acid. Such plants are sometimes referred to as transgenic plants. The phenotype produced in a particular plant is dependent upon the design of the vector used to produce it. Thus, the vector can be designed to transcribe a nucleic acid which encodes at least a portion of the C3H protein. In such cases, the C3H protein so produced is capable of conferring a particular phenotype based on the presence of that protein within the cell. Alternatively, the vector can be constructed such that transcription results in the formation of a transcript which is capable of hybridizing with an RNA transcript of an endogenous C3H homolog gene. This approach employs the well known antisense technology and results in a modulation in the phenotypic effect of the endogenous REF8 genes. Such modulation of the endogenous REF8 gene can also potentially be obtained by using the sense strand of the REF8 gene to cause sense suppression of the endogenous REF8 alleles as well as the REF8 gene introduced in the vector. The production of a plant containing such a phenotype is contemplated based upon the sense suppression observed in Petunia hybrida as set forth in PCT Publication WO 90/12084.

"Encode." A polynucleotide is said to "encode" a polypeptide if, in its native state or when manipulated by methods well known to those skilled in the art, it can be transcribed and/or translated to produce the RNA for and/or the polypeptide or a fragment thereof. The anti-sense strand is the complement of such a nucleic acid and the encoding sequence can be deduced there from.

"Operably linked" refers to a juxtaposition wherein the components so described are in a relationship permitting them to function in their intended manner, i.e., a promoter is operably linked to a coding sequence if the promoter affects its transcription or expression.

As used herein, a "portion" of the REF8 locus or region or allele is defined as having a minimal size of at least about eight nucleotides, or preferably about 15 nucleotides, or more preferably at least about 25 nucleotides, and may have a minimal size of at least about 40 nucleotides. This definition includes all sizes in the range of 8–40 nucleotides as well as greater than 40 nucleotides. Thus, this definition includes nucleic acids of 8, 12, 15, 20, 25, 40, 60, 80, 100, 200, 300, 400, 500 nucleotides, or nucleic acids having any number of nucleotides within these ranges of values (e.g., 9, 10, 11, 16, 23, 30, 38, 50, 72, 121, etc., nucleotides), or nucleic acids having at least 8 nucleotides derived from SEQ ID NO:1 or SEQ ID NO:2, their complement or functionally equivalent nucleic acid sequences.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

"REF8 allele" refers, respectively, to normal alleles of the REF8 locus as well as alleles of REF8 having variations, isolated from plants or produced in accordance with the present invention.

"REF8 locus", REF8 gene", "REF8 nucleic acids" or "REF8 polynucleotide" each refer to polynucleotides, all of which are in the REF8 region, respectively, that are likely to be expressed in normal tissue and involved in phenylpropanoid metabolism. The REF8 locus is intended to include coding sequences, intervening sequences and regulatory elements (e.g., promoters and enhancers) controlling transcription and/or translation. The REF8 locus is intended to include all allelic variations of the DNA sequence.

These terms, when applied to a nucleic acid, refer to a nucleic acid which encodes a C3H polypeptide, fragment, homolog or variant, including, e.g., protein fusions or deletions. The nucleic acids of the present invention will possess a sequence which is either derived from, or substantially similar to, a natural REF8-encoding gene or one having substantial homology with a natural REF8-encoding gene or a portion thereof. The term REF8 nucleic acid is sometimes used to refer to the sense and antisense strands of the REF8 gene collectively.

The REF8 gene or nucleic acid includes normal alleles of the REF8 gene, respectively, including silent alleles having no effect on the amino acid sequence of the C3H polypeptide that do not substantially affect its function. These terms also include alleles having one or more mutations which adversely affect the function of the C3H polypeptide. A mutation may be a change in the REF8 nucleic acid sequence which produces a deleterious change in the amino acid sequence of the C3H polypeptide, resulting in partial or complete loss of C3H protein function, such as ref8, or may be a change in the nucleic acid sequence which results in the loss of effective C3H protein expression or the production of aberrant forms of the C3H polypeptide.

The REF8 nucleic acid may be that shown in SEQ ID NO:1 or SEQ ID NO:2 or it may be an allele as described above or a variant or derivative differing from that shown by a change which is one or more of addition, insertion, deletion and substitution of one or more nucleotides of the sequence shown. Changes to the nucleotide sequence may result in an amino acid change at the protein level, or not, as determined by the genetic code.

Thus, nucleic acid according to the present invention may include a sequence different from the sequence shown in SEQ ID No:1 or SEQ ID NO:2 yet encode a polypeptide with the same amino acid sequence as shown in SEQ ID NO:4 or SEQ ID NO:5. That is, nucleic acids of the present invention include sequences which are degenerate as a result of the genetic code. On the other hand, the encoded polypeptide may comprise an amino acid sequence which differs by one or more amino acid residues from the amino acid sequence shown in SEQ ID NO:4, such as that of SEQ ID NO:5. Nucleic acid encoding a polypeptide which is an amino acid sequence variant, derivative or allele of the amino acid sequence shown in SEQ ID NO:4 or SEQ ID NO:5 is also provided by the present invention.

The REF8 gene, respectively, also refers to (a) any DNA sequence that (i) hybridizes to the complement of the DNA sequences that encode the amino acid sequence set forth in SEQ ID NO:4 or SEQ ID NO:5 under less stringent conditions, such as moderately stringent conditions (Ausubel et al. (1992)) and (ii) encodes a gene product functionally equivalent to REF8. The invention also includes nucleic acid molecules that are the complements of the sequences described herein.

The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute to phosphate linkages in the backbone of the molecule.

The present invention provides recombinant nucleic acids comprising all or part of the REF8 region. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature. Where nucleic acid according to the invention included RNA, reference to the sequence shown should be construed as reference to the RNA equivalent, with U substituted for T.

Therefore, recombinant nucleic acids comprising sequences otherwise not naturally occurring are provided by this invention. Although the wild-type sequence may be employed, it may also be altered, e.g., by deletion, substitution or insertion. cDNA or genomic libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source which is abundant in mRNA for the desired proteins. Phage libraries are normally preferred, but other types of libraries may be used. Clones of a library are spread onto plates, transferred to a substrate for screening, denatured and probed for the presence of desired sequences.

The DNA sequences used in this invention will usually comprise at least about five codons (15 nucleotides), more usually at least about 7–15 codons, and most preferably, at least about 35 codons. One or more introns may also be present. This number of nucleotides is usually about the minimal length required for a successful probe that would hybridize specifically with an REF8 encoding sequence. In this context, oligomers of as low as 8 nucleotides, more generally 8–17 nucleotides, can be used for probes, especially in connection with chip technology.

Techniques for nucleic acid manipulation are described generally, e.g., in Sambrook et al. (1989) or Ausubel et al. (1992). Reagents useful in applying such techniques, such as restriction enzymes and the like, are widely known in the art and commercially available from such vendors as New England BioLabs, Boehringer Mannheim, Amersham, Promega, U. S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic libraries using appropriate probes. See, GenBank, National Institutes of Health.

"C3H protein" and "C3H polypeptide" refers to a protein or polypeptide encoded by the REF8 locus, variants or fragments thereof. The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example unnatural amino acids, etc.), polypeptides with substituted linkages as well as other modifications known in the art, both naturally and non-naturally occurring. Ordinarily, such polypeptides will be at least about 50% homologous to the native REF8 nucleic acid sequence, preferably in excess of about 90%, and more preferably at least about 95% homologous. Also included are proteins encoded by DNA which hybridize under high or low stringency conditions, to REF8-encoding nucleic acids and closely related polypeptides or proteins retrieved by antisera to the C3H protein(s).

The C3H polypeptide may be that shown in SEQ ID NO:4 or SEQ ID NO:5 which may be in isolated and/or purified form, free or substantially free of material with which it is naturally associated. The polypeptide may, if produced by expression in a prokaryotic cell or produced synthetically, lack native post-translational processing, such as glycosylation. Alternatively, the present invention is also directed to polypeptides which are sequence variants, alleles or derivatives of the C3H polypeptide. Such polypeptides may have an amino acid sequence which differs from that set forth in SEQ ID NO:4 or SEQ ID NO:5 by one or more of addition, substitution, deletion or insertion of one or more amino acids. In one embodiment, these variant polypeptides have a function similar to C3H protein. In a second embodiment, these variant peptides do not retain the C3H protein function such that they can be used as a dominant negative.

Substitutional variants typically contain the exchange of one amino acid for another at one or more sites within the protein, and may be designed to modulate one or more properties of the polypeptide, such as stability against proteolytic cleavage, without the loss of other functions or properties. Amino acid substitutions may be made on the basis of similarity in polarity, charge, solubility, hydrophobicity, hydrophilicity, and/or the amphipathic nature of the residues involved. Preferred substitutions are ones which are conservative, that is, one amino acid is replaced with one of similar shape and charge. Conservative substitutions are well known in the art and typically include substitutions within the following groups: glycine, alanine; valine, isoleucine, leucine; aspartic acid, glutamic acid; asparagine, glutamine; serine, threonine; lysine, arginine; and tyrosine, phenylalanine.

Certain amino acids may be substituted for other amino acids in a protein structure without appreciable loss of interactive binding capacity with structures such as, for example, antigen-binding regions of antibodies or binding sites on substrate molecules or binding sites on proteins interacting with the C3H polypeptide. Since it is the interactive capacity and nature of a protein which defines that protein's biological functional activity, certain amino acid substitutions can be made in a protein sequence, and its underlying DNA coding sequence, and nevertheless obtain a protein with like properties. In making such changes, the hydropathic index of amino acids may be considered. The importance of the hydrophobic amino acid index in conferring interactive biological function on a protein is generally understood in the art (U.S. Pat. No. 4,554,101). The use of the hydrophobic index or hydrophilicity in designing polypeptides is further discussed in U.S. Pat. No. 5,691,198.

The length of polypeptide sequences compared for homology will generally be at least about 16 amino acids, usually at least about 20 residues, more usually at least about 24 residues, typically at least about 28 residues, and preferably more than about 35 residues.

"VIGS" or "virus induced gene silencing" refers to suppression of gene expression in plants in a sequence-specific manner by infection with virus vectors carrying fragments of host genes. The mechanism of this gene silencing is based on an RNA-mediated defense against viruses (Baulcombe, 1999). It has also emerged that a related mechanism is involved in the post-transcriptional silencing that accounts for between line variation in transgene expression and co suppression of transgenes and endogenous genes.

"Regulatory sequences" refers to those sequences which affect the expression of the gene (including transcription of the gene, and translation, splicing, stability or the like of the messenger RNA and tissue specificity). These sequences are normally within 100 kb of the coding region of a locus, although they may also be more distant from the coding region, or they may be located within coding regions of the gene.

As used herein, an "isolated nucleic acid molecule" is a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

A nucleic acid or fragment thereof has substantial identity with another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases. A protein or fragment thereof has substantial identity with another if, optimally aligned, there is an amino acid sequence identity of at least about 30% identity with an entire naturally-occurring protein or a portion thereof, usually at least about 70% identity, more usually at least about 80% identity, preferably at least about 90% identity, and more preferably at least about 95% identity.

Identity means the degree of sequence relatedness between two polypeptide or two polynucleotides sequences as determined by the identity of the match between two strings of such sequences, such as the full and complete sequence. Identity can be readily calculated. While there exist a number of methods to measure identity between two polynucleotide or polypeptide sequences, the term "identity" is well known to skilled artisans (Lesk, A. M., ed., 1988; Smith, D. W., ed., 1993; Griffin and Griffin, eds., 1994; von Heinje, 1987; and Gribskov and Devereux, eds., 1991). Methods commonly employed to determine identity between two sequences include, but are not limited to those disclosed in *Guide to Huge Computers*, Martin J. Bishop, ed., Academic Press, San Diego, 1994, and Carillo and Lipman, 1988. Preferred methods to determine identity are designed to give the largest match between the two sequences tested. Such methods are codified in computer programs. Preferred computer program methods to determine identity between two sequences include, but are not limited to, GCG (Genetics Computer Group, Madison Wis.) program package (Devereux, et al., 1984), BLASTP, BLASTN, FASTA (Altschul, et al., 1990; Altschul, et al., 1997). The well-known Smith Waterman algorithm may also be used to determine identity.

As an illustration, by a polynucleotide having a nucleotide sequence having at least, for example, 95% "identity" to a reference nucleotide sequence of is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence.

Alternatively, substantial homology or (similarity) exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30 C., typically in excess of 37 C., and preferably in excess of 45 C. Stringent salt conditions will ordinarily be less than 1000 mM, typically less than 500 mM, and preferably less than 200 mM. However, the combination of parameters is much more important than the measure of any single parameter. The stringency conditions are dependent on the length of the nucleic acid and the base composition of the nucleic acid, and can be determined by techniques well known in the art. See, e.g., Ausubel, 1987; Wetmur and Davidson, 1968.

Thus, as herein used, the term "stringent conditions" means hybridization will occur only if there is at least 95% and preferably at least 97% identity between the sequences. Such hybridization techniques are well known to those of skill in the art. Stringent hybridization conditions are as defined above or, alternatively, conditions under overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 µg/ml denatured, sheared salmon sperm DNA, followed by washing the filters in 0.1×SSC at about 65° C.

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art which are utilized for purification.

Large amounts of the nucleic acids of the present invention may be produced by (a) replication in a suitable host or transgenic animals or (b) chemical synthesis using techniques well known in the art. Constructs prepared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Secretion signals may also be included where appropriate which allow the protein to cross and/or lodge in cell membranes, and thus attain its functional topology, or be secreted from the cell. Such vectors may be prepared by means of standard recombinant techniques well known in the art.

"Codon degeneracy" refers to the nature in the genetic code permitting variation of the nucleotide sequence without effecting the amino acid sequence of an encoded polypeptide. Accordingly, the instant invention relates to any nucleic acid molecule that encodes all or a substantial portion of the amino acid sequence encoding the instant C3H polypeptides as set forth in SEQ ID NOs:2 and 4. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid molecule that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene or gene copy that was not originally found in the host organism, but that is introduced into the host organism by gene transfer. Foreign genes can comprise native genes inserted into a non-native organism, additional copies of a native gene inserted into a native organism or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 9928508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

The term "expression", as used herein, refers to the transcription and stable accumulation of sense (mRNA) or antisense RNA derived from the nucleic acid molecule of the invention. Expression may also refer to translation of mRNA into a polypeptide.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals such as transit peptides.

A "signal peptide" is an amino acid sequence that is translated in conjunction with a protein and directs the protein across cell membranes of the cell in which the protein is made. For example, a signal peptide can be used to direct a mature enzyme into a cell's chloroplast or into a cell's vacuole via endoplasmic reticulum. A signal peptide is also referred to as a signal protein. "Signal sequence" refers to a nucleotide sequence that encodes a signal peptide.

The signal peptide is covalently bound to the "mature enzyme" or "passenger enzyme." The term "precursor protein" identifies a polypeptide having a signal peptide and a passenger peptide covalently attached to each other. Typically, the carboxy terminus of the signal peptide is covalently attached to the amino terminus of the passenger peptide. The passenger peptide and signal peptide can be encoded by the same gene locus, that is, homologous to each other, in that they are encoded in a manner isolated from a single source. Alternatively, the signal peptide and passenger peptide can be heterologous to each other, i.e., the signal peptide and passenger peptide can be from different genes and/or different organisms. The transit peptide may be derived from monocotyledonous or dicotyledonous plants upon choice of the artisan. The term "signal peptide" includes amino acid sequences that are translated in conjunction with a protein and directs the protein to the secretory system (Chrispeels, 1991). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel, 1992).

By "mature peptide" or "passenger peptide" is meant a polypeptide which is found after processing and passing into an organelle and which is functional in the organelle for its intended purpose. Passenger peptides are originally made in a precursor form that includes a signal peptide and the passenger peptide. Upon entry into an organelle, the signal peptide portion is cleaved, thus leaving the "passenger" or "mature" peptide. Passenger peptides are the polypeptides typically obtained upon purification from a homogenate, the sequence of which can be determined as described herein.

"Transformation" refers to the transfer of a nucleic acid molecule into the genome of a host organism, resulting in genetically stable inheritance. Host organisms containing the transformed nucleic acid molecules are referred to as "transgenic" or "recombinant" or "transformed" organisms.

As used herein, "transgenic plant" includes reference to a plant which comprises within its genome a foreign polynucleotide. Generally, the foreign polynucleotide is stably integrated within the genome such that the polynucleotide is passed on to successive generations. The foreign polynucleotide may be integrated into the genome alone or as part of a recombinant expression cassette. "Transgenic" is used herein to include any cell, cell line, callus, tissue, plant part or plant, the genotype of which has been altered by the presence of foreign nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul, et al., 1990), and DNASTAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

In one aspect of the invention, sense and antisense nucleic acid fragments that encode C3H or c3 h, and nucleic acids fragments substantially similar thereto.

It is of course not intended that the present invention be limited to these exemplary nucleotide sequences, but the invention also encompasses nucleic acid fragments substantially similar to those set forth above. In a preferred aspect, the present invention provides nucleic acid fragments that encode polypeptides in accordance with the invention that have at least about 80% identity to the amino acid sequence of SEQ ID NO:4, SEQ ID NO:5, SEQ ID NO:6 or SEQ ID NO:7, more preferably, at least about 90% identity to one these sequences and most preferably at least about 95% identity. Similarly, preferred nucleic acid sequences corresponding to the instant ref8 gene are at least 80% identical to one of the nucleic acid sequences of reported herein. More preferred nucleic acid fragments are at least 90% identical to one of the sequences herein. Most preferred are nucleic acid fragments that are at least 95% identical to one of the nucleic acid fragments reported herein.

In another aspect, the present invention relates to methods and compositions for obtaining transformed cells, said cells expressing c3 h. In this regard, inventive nucleotide sequences can be incorporated into vectors, which in turn can be used to transform cells. Expression of c3 h results in the cell having altered metabolic activity relative to non-transformed cells. Transformants harboring an expressible inventive nucleotide sequence demonstrate increased levels of activity when appropriate substrates are available, and have other desirable features as would occur to a person of ordinary skill in the art. These and other features of the invention are described in further detail below.

Inventive DNA sequences can be incorporated into the genome of a plant or microorganism using conventional recombinant DNA technology, thereby making a transformed plant or microorganism that expresses c3 h. As described above, the term "genome" as used herein is intended to refer to DNA which is present in a plant or microorganism and which is heritable by progeny during propagation thereof. As such, an inventive transformed plant or microorganism may alternatively be produced by producing F1 or higher generation progeny of a directly transformed plant or microorganism, wherein the progeny comprise the foreign nucleotide sequence. Transformed plants or microorganisms and progeny thereof are all contemplated by the invention and are all intended to fall directly within the meaning of the terms "transformed plant" and "transformed microorganism."

In this manner, the present invention contemplates the use of transformed plants that are selfed to produce an inbred plant. The inbred plant produces seed containing the gene of interest. These seeds can be grown to produce plants that express the polypeptide of interest. The inbred lines can also be crossed with other inbred lines to produce hybrids. Parts obtained from the regenerated plant, such as flowers, seeds, leaves, branches, fruit, and the like are covered by the invention provided that said parts contain genes encoding and/or expressing the protein of interest. Progeny and variants, and mutants of the regenerated plants are also included within the scope of the invention.

In diploid plants, typically one parent may be transformed and the other parent is the wild type. After crossing the parents, the first generation hybrids (F1) are selfed to produce second generation hybrids (F2). Those plants exhibiting the highest levels of the expression can then be chosen for further breeding.

Standard recombinant DNA and molecular cloning techniques used in accordance with the present invention are well known in the art. See, e.g., Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); by Silhavy, et al. (1984); and by Ausubel, et al (1992); Sambrook et al. (1989); Glover (1985); Guthrie and Fink (1991); Weissbach and Weissbach (1986); Zaitlin et al. (1985) and Gelvin et al. (1990).

Method of Use: Recombinant Microbial Expression of Mutant ref8

It will be useful to recombinantly express the ref8 gene for the production of mutant C3H with altered biological activity in heterologous host cells, particularly in the cells of microbial hosts, to produce large amounts of the mutant c3 h enzyme.

Preferred heterologous host cells for express of the instant genes and nucleic acid molecules are microbial hosts. Specific suitable hosts include but are not limited *Aspergillus, Trichoderma, Saccharomyces, Pichia, Candida, Hansenula, Salmonella, Bacillus, Acinetobacter, Rhodococcus, Streptomyces, Escherichia*, and *Pseudomonas,* where *E. coli* is most preferred.

Microbial expression systems and expression vectors containing regulatory sequences that direct high level expression of foreign proteins are well known to those skilled in the art. A wide variety of such systems and vectors could be used to construct chimeric genes for production of the gene products of the instant sequences. These chimeric genes could then be introduced into appropriate microorganisms via transformation to provide high level expression of the enzymes.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. Both control regions are preferably derived from genes homologous to the transformed host cell, although it is to be understood that such control regions need not be derived from the genes native to the specific species chosen as a production host.

Initiation control regions or promoters, which are useful to drive expression of the instant genes in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, $lP_L$, $lP_R$, T7, tac, and trc (useful for expression in *Escherichia coli*) as well as the amy, apr, npr promoters and various phage promoters useful for expression in *Bacillus*.

Termination control regions may also be derived from various genes native to the preferred hosts. Optionally, a termination site may be unnecessary, however, it is most preferred if included.

It is readily understood that, in the case of transforming prokaryotes, it is not necessary to include a signal peptide in the coding region of the vector. Rather, an inventive DNA construct for transforming, for example, bacteria, may be made by simply attaching a start codon directly to, and in the proper reading frame with, a nucleic acid fragment encoding a mature peptide. Of course, other elements are preferably present as described herein, such as a promoter upstream of the start codon and a termination sequence downstream of the coding region.

Optionally it may be desired to produce the instant gene product as a secretion product of the transformed host. Secretion of desired proteins into the growth media has the advantages of simplified and less costly purification procedures. It is well known in the art that secretion signal sequences are often useful in facilitating the active transport of expressible proteins across cell membranes. The creation of a transformed host capable of secretion may be accomplished by the incorporation of a DNA sequence that codes for a secretion signal that is functional in the host production host. Methods for choosing appropriate signal sequences are well known in the art (see for example EP 546049; WO 9324631). The secretion signal DNA or facilitator may be located between the expression-controlling DNA and the instant gene or gene fragment, and in the same reading frame with the latter.

Method of Use: Expression of Mutant ref8 in Transgenic Plants

The ref8 gene may be used to create transgenic plants having the ability to express mutant c3 h. Transgenic plants expressing a functioning ref8 gene exhibit modifications in their secondary metabolite profile.

Preferred plant hosts will be any variety that will support a high production level of the mutant c3 h proteins. Suitable green plants include but are not limited to soybean, rapeseed (*Brassica napus, B. campestris*), sunflower (*Helianthus annus*), cotton (*Gossypium hirsutum*), corn, tobacco (*Nicotiana tabacum*), alfalfa (*Medicago sativa*), wheat (*Triticum sp*), barley (*Hordeum vulgare*), oats (*Avena sativa*, L), sorghum (*Sorghum bicolor*), rice (*Oryza sativa*), *Arabidopsis*, cruciferous vegetables (broccoli, cauliflower, cabbage, etc.), melons, carrots, celery, parsley, tomatoes, potatoes, strawberries, peanuts, grapes, grass seed crops, sugar beets, sugar cane, beans, peas, rye, flax, hardwood trees, softwood trees, and forage grasses The present invention further provides recombinant expression cassettes comprising the ref8 coding region. A recombinant expression cassette will typically comprise an ref8 polynucleotide of the present invention operably linked to transcriptional initiation regulatory sequences which will direct the transcription of the gene in the intended host cell, such as tissues of a transformed plant. An expression vector according to the invention may be either naturally or artificially produced from parts derived from heterologous sources, which parts may be naturally occurring or chemically synthesized, and wherein the parts have been joined by ligation or other means known in the art. The introduced coding sequence is preferably under control of a promoter and thus will be generally downstream from the promoter. Stated alternatively, the promoter sequence will be generally upstream (i.e., at the 5' end) of the coding sequence. The phrase "under control of" contemplates the presence of such other elements as may be necessary to achieve transcription of the introduced sequence. As such, in one representative example, enhanced production of mutant C3H polypeptide may be achieved by inserting an inventive nucleotide sequence in a vector downstream from and operably linked to a promoter sequence capable of driving expression in a host cell. Two DNA sequences (such as a promoter region sequence and an C3H-encoding nucleotide sequence) are said to be operably linked if the nature of the linkage between the two DNA sequences does not (1) result in the introduction of a frame-shift mutation, (2) interfere with the ability of the promoter region sequence to direct the transcription of the desired nucleotide sequence, or (3) interfere with the ability of the desired nucleotide sequence to be transcribed by the promoter region sequence.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

A plant promoter fragment can be employed which will direct expression of ref8 in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, and the GRP1-8 promoter.

Alternatively, the plant promoter can direct expression of a polynucleotide of the present invention in a specific tissue or may be otherwise under more precise environmental or developmental control. Such promoters are referred to here as "inducible" promoters. Environmental conditions that may effect transcription by inducible promoters include pathogen attack, anaerobic conditions, or the presence of light. Examples of inducible promoters are the Adh1 promoter, which is inducible by hypoxia or cold stress, the Hsp70 promoter, which is inducible by heat stress, and the PPDK promoter, which is inducible by light.

Examples of promoters under developmental control include promoters that initiate transcription only, or preferentially, in certain tissues, such as leaves, roots, fruit, seeds, or flowers. Exemplary promoters include the anther specific promoter 5126 (U.S. Pat. Nos. 5,689,049 and 5,689,051), glob-1 promoter, and gamma-zein promoter. The operation of a promoter may also vary depending on its location in the genome. Thus, an inducible promoter may become fully or partially constitutive in certain locations.

Both heterologous and non-heterologous (i.e., endogenous) promoters can be employed to direct expression of the ref8 gene. These promoters can also be used, for example, in recombinant expression cassettes to drive expression of antisense nucleic acids to provide, reduce, increase, or alter concentration and/or composition of the C3H protein in a desired tissue. Thus, in some embodiments, the nucleic acid construct will comprise a promoter functional in a plant cell, such as in *Zea mays* or tobacco, operably linked to ref8 gene. Promoters useful in these embodiments include endogenous promoters driving expression of C3H.

Where c3 h polypeptide expression is desired, it is generally desirable to include a polyadenylation region at the 3'-end of a polynucleotide coding region of ref8. The polyadenylation region can be derived from the wild-type gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence or the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg (1988); Callis, et al. (1987). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds. (1994). The vector comprising the REF8 sequence will typically comprise a marker gene which confers a selectable phenotype on plant cells. Typical vectors useful for expression of genes in higher plants are well known in the art and include vectors derived from the tumor-inducing (Ti) plasmid of *Agrobacterium tumefaciens* described by Rogers, et al. (1987).

ref8 can be expressed in either sense or anti-sense orientation as desired. It will be appreciated that control of gene expression in either sense or anti-sense orientation can have a direct impact on the observable plant characteristics. Antisense technology can be conveniently used to inhibit C3H gene expression in plants. To accomplish this, ref8 or a portion of ref8 is cloned and operably linked to a promoter such that the anti-sense strand of RNA will be transcribed. The construct is then transformed into plants and the antisense strand of RNA is produced. In plant cells, it has been shown that antisense RNA inhibits gene expression by preventing the accumulation of mRNA which encodes the enzyme of interest, see, e.g., Sheehy, et al. (1988); and Hiatt et al., U.S. Pat. No. 4,801,340.

Another method of suppression is sense suppression (i.e., co-suppression). Introduction of nucleic acid configured in the sense orientation has been shown to be an effective means by which to block the transcription of target genes. For an example of the use of this method to modulate expression of endogenous genes see, Napoli et al. (1990) and U.S. Pat. No. 5,034,323. Such a method may be applied to the regulation of C3H expression.

Catalytic RNA molecules or ribozymes can also be used to inhibit expression of plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff, et al. (1988).

To introduce ref8 into a plant, generally the gene will first be incorporated into a recombinant expression cassette or vector, by a variety of methods known in the art. See, for example, Weising, et al. (1988). For example, the DNA construct may be introduced directly into the genomic DNA of the plant cell using techniques such as electroporation, polyethylene glycol (PEG), poration, particle bombardment, silicon fiber delivery, or microinjection of plant cell protoplasts or embryogenic callus. See, e.g., Tomes, et al., Direct DNA Transfer into Intact Plant Cells Via Microprojectile Bombardment. pp. 197–213 in Plant Cell, Tissue and Organ Culture, Fundamental Methods. eds. O. L. Gamborg and G. C. Phillips. Springer-Verlag Berlin Heidelberg New York, 1995. The introduction of DNA constructs using PEG precipitation is described in Paszkowski, et al. (1984). Electroporation techniques are described in Fromm, et al. (1985). Ballistic transformation techniques are described in Klein, et al. (1987).

Alternatively, *Agrobacterium tumefaciens*-mediated transformation techniques may be used. See, for example Horsch, et al. (1984); Fraley, et al., (1983); and, *Plant Molecular Biology: A Laboratory Manual*, Chapter 8, Clark, Ed. (1997). The DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616. Although *Agrobacterium* is useful primarily in dicots, certain monocots can be transformed by *Agrobacterium*: For instance, *Agrobacterium* transformation of maize is described in U.S. Pat. No. 5,550,318.

Other methods of transfection or transformation include (1) *Agrobacterium rhizogenes*-mediated transformation (see, e.g., Lichtenstein and Fuller, 1987; and Lichtenstein and Draper, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16 (2) liposome-mediated DNA uptake (see, e.g., Freeman, et al., 1984), (3) the vortexing method (see, e.g., Kindle, 1990).

DNA can also be introduced into plants by direct DNA transfer into pollen as described by Zhou, et al., 1983; Hess, 1987; Luo, et al., 1988). Expression of REF8 can be obtained by injection of the DNA into reproductive organs of a plant as described by Pena, et al. (1987). The gene can also be injected directly into the cells of immature embryos and the rehydration of desiccated embryos as described by Neuhaus, et al. (1987); and Benbrook, et al. (1986). A variety of plant viruses that can be employed as vectors are known in the art and include cauliflower mosaic virus (CaMV), geminivirus, brome mosaic virus, and tobacco mosaic virus.

Plant cells that directly result or are derived from the nucleic acid introduction techniques can be cultured to regenerate a whole plant that possesses the introduced genotype. Such regeneration techniques often rely on manipulation of certain phytohormones in a tissue culture growth medium. Plants cells can be regenerated, e.g., from single cells, callus tissue or leaf discs according to standard plant tissue culture techniques. It is well known in the art that various cells, tissues, and organs from a wide variety of plants can be successfully cultured to regenerate an entire plant. Plant regeneration from cultured protoplasts is described in Evans, et al. (1983); and Binding (1985).

The regeneration of plants from either single plant protoplasts or various explants is well known in the art. See, for example, Weissbach and Weissbach (eds., 1988). This regeneration and growth process includes the steps of selection of transformant cells and shoots, rooting the transformant shoots and growth of the plantlets in soil. For maize cell culture and regeneration see generally, Freeling and Walbot (Eds., 1994); Sprague and Dudley (Eds., 1988). For transformation and regeneration of maize see, Gordon-Kamm, et al. (1990).

The regeneration of plants containing the polynucleotide of the present invention and introduced by *Agrobacterium* from leaf explants can be achieved as described by Horsch, et al. (1985). In this procedure, transformants are grown in the presence of a selection agent and in a medium that induces the regeneration of shoots in the plant species being transformed as described by Fraley, et al. (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile. Additional literature describing plant and/or microorganism transformation includes the following, each of which is incorporated herein by reference in its entirety: Zhijian Li, et al. (1992); Parsons, et al. (1997); Daboussi, et al. (1989); Leung, et al. (1990); Koetter, et al. (1990); Strasser et al., "Cloning of yeast xylose reductase and xylitol dehydrogenase genes and their use," German patent application (1990); Hallborn, et al. (1991); Becker and Guarente (1991); Ammerer (1983); Sarthy, et al. (1987); U.S. Pat. Nos. 4,945,050, 5,141,131, 5,177,010, 5,104,310, 5,149,645, 5,469,976, 5,464,763, 4,940,838, 4,693,976, 5,591,616, 5,231,019, 5,463,174, 4,762,785, 5,004,863, 5,159,135, 5,302,523, 5,464,765, 5,472,869, 5,384,253; European Patent Application Nos. 0131624B1, 120516, 159418B1, 176112, 116718, 290799, 320500, 604662, 627752, 0267159, 0292435; WO 87/06614; WO 92/09696; and WO 93/21335.

Once the recombinant DNA is introduced into the plant tissue, successful transformants can be screened using standard techniques such as the use of marker genes, e.g., genes encoding resistance to antibiotics. Additionally, the level of expression of the foreign DNA may be measured at the transcriptional level, by measuring the amount of protein synthesized or by assaying to determine the level of enzyme function in the plant. One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed. In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self-crossed to produce a homozygous inbred plant. The inbred plant produces seed containing the newly introduced heterologous nucleic acid. These seeds can be grown to produce plants that would produce the selected phenotype. Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these part comprise the introduced nucleic acid sequences.

Transgenic plants expressing a polynucleotide of the present invention can be screened for transmission of the nucleic acid of the present invention by, for example, standard immunoblot and DNA detection techniques. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then be analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are screened for the incorporated nucleic acid to identify and select plants with the most appropriate expression profiles.

Methods of Use: Isolation of Homologs and Orthologs

In another aspect of the invention, the sequence of the REF8 or ref8 genes may be used to isolate orthologous genes encoding homologous proteins from other plants, which genes and the expression products thereof, can be readily tested for functionality in accordance with the present invention by a person of ordinary skill in the art. The DNA identities of full length sequences encoding C3H from *sorghum,* soybean and sweetgum reflect 57 to 73% identity to the coding sequence of CYP98 (Table 1). Those in the art would know to clone an ortholog of the REF8 gene and use the sequence thereof to down regulate the expression of the respective plant's endogenous C3H gene.

PERCENT IDENTITY

|   | 1 | 2 | 3 | 4 |
|---|---|---|---|---|
| 1 |   | 56.9 | 68.8 | 69.6 |
| 2 | 47.8 |   | 59.5 | 58.3 |
| 3 | 34.2 | 43.1 |   | 73.3 |
| 4 | 33.0 | 46.5 | 28.5 |   |
|   | 1 | 2 | 3 | 4 |

TABLE 1

Sequence Pair Distances

A.t_Cyp98CDS.seq(1)
Sorghum_Cyp98A1.seq(2)
Soybean_Cyp98A2.seq(3)
Sweetgum_Cyp98.seq(4)

Clustal method with weighted residue weight table.

It is well known that plants and microorganisms of a wide variety of species commonly express and utilize analogous enzymes and/or polypeptides which have varying degrees of degeneracy, and yet which effectively provide the same or a similar function. For example, an amino acid sequence isolated from one species may differ to a certain degree from the sequence set forth in SEQ ID NO:4, SEQ ID NO:5, SEQ ID NO:6 or SEQ ID NO:7 and yet have similar functionality. Amino acid sequences comprising such variations, and methods for identifying and isolating the same, are included within the scope of the present invention.

Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g. polymerase chain reaction (PCR), Mullis et al., U.S. Pat. 4,683,202; ligase chain reaction (LCR), Tabor, et al. (1985); or strand displacement amplification (SDA), Walker, et al. (1992)).

For example, genes encoding similar proteins or polypeptides to the C3H polypeptide could be isolated directly by using all or a portion of the instant nucleic acid molecules as DNA hybridization probes to screen libraries from any desired bacteria using methodology well known to those skilled in the art. Specific oligonucleotide probes based upon the instant ref8 sequences can be designed and synthesized by methods known in the art (Maniatis). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length DNA fragments under conditions of appropriate stringency.

Generally two short segments of the instant sequences may be used in polymerase chain reaction protocols to amplify longer nucleic acid molecules encoding homologous genes from DNA or RNA. The polymerase chain reaction may also be performed on a library of cloned nucleic acid molecules wherein the sequence of one primer is derived from the instant REF8 nucleic acid molecules, and the sequence of the other primer takes advantage of the presence of the polyadenylic acid tracts to the 3' end of the mRNA precursor encoding the instant genes. Alternatively, the second primer sequence may be based upon sequences derived from the cloning vector. For example, the skilled artisan can follow the RACE protocol (Frohman, et al., 1988) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara, et al., 1989; Loh, et al., 1989). Typically, in PCR-type amplification techniques, the primers have different sequences and are not complementary to each other. Depending on the desired conditions, the sequences of the primers should be designed to provide for both efficient and faithful replication of the target nucleic acid. Methods of PCR primer design are common and well known in the art (Thein and Wallace, 1986; Rychlik, 1993).

Alternatively the instant REF8 and ref8 sequences may be employed as hybridization reagents for the identification of homologs. The basic components of a nucleic acid hybridization test include a probe, a sample suspected of containing the gene or gene fragment of interest, and a specific hybridization method. Probes of the present invention are typically single stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration the shorter the hybridization incubation time needed. Optionally a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, 1991). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1M sodium chloride, about 0.05 to 0.1M buffers, such as sodium citrate, Tris-HCl, PIPES or HEPES (pH range about 6–9), about 0.05 to 0.2% detergent, such as sodium dodecylsulfate, or between 0.5–20 mM EDTA, FICOLL (Pharmacia Inc.) (about 300–500 kilo Daltons), polyvinylpyrrolidone (about 250–500 kdal), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents that include a variety of polar water-soluble or swellable agents, such as polyethylene glycol, anionic polymers such as polyacrylate or polymethylacrylate, and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Availability of the instant nucleotide and deduced amino acid sequences facilitates immunological screening DNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen DNA expression libraries to isolate full-length DNA clones of interest (Lerner, 1984; Maniatis).

It is also contemplated in accordance with the present invention that REF8 can be used to produce gene products having enhanced or altered activity. Various methods are known for mutating a native gene sequence to produce a gene product with altered or enhanced activity including but not limited to error prone PCR (Melnikov, et al., 1999); site directed mutagenesis (Coombs, et al., 1998), and "gene shuffling" (U.S. Pat. Nos. 5,605,793; 5,811,238; 5,830,721; and 5,837,458, incorporated herein by reference).

The method of gene shuffling is particularly attractive due to its facile implementation, and high rate of mutagenesis and ease of screening. The process of gene shuffling involves the restriction endonuclease cleavage of a gene of interest into fragments of specific size in the presence of additional populations of DNA regions of both similarity to and difference from the gene of interest. This pool of fragments will then be denatured and reannealed to create a mutated gene. The mutated gene is then screened for altered activity.

The instant ref8 sequences can be further mutated and screened for altered or enhanced activity by this method. The sequences should be double stranded and can be of various lengths ranging form 50 bp to 10 kb. The sequences can be randomly digested into fragments ranging from about 10 bp to 1000 bp, using restriction endonucleases well known in the art (Maniatis supra). In addition to the instant ref8 sequences, populations of fragments that are hybridizable to all or portions of the ref8 sequence can be added. Similarly, a population of fragments that are not hybridizable to the instant ref8 sequence can also be added. Typically these additional fragment populations are added in about a 10 to 20 fold excess by weight as compared to the total nucleic acid. Generally if this process is followed the number of different specific nucleic acid fragments in the mixture will be about 100 to about 1000. The mixed population of random nucleic acid fragments are denatured to form single-stranded nucleic acid fragments and then reannealed. Only those single-stranded nucleic acid fragments having regions of homology with other single-stranded nucleic acid fragments will reanneal. The random nucleic acid fragments may be denatured by heating. One skilled in the art could determine the conditions necessary to completely denature the double stranded nucleic acid. Preferably the temperature is from 80° C. to 100° C. The nucleic acid fragments may be reannealed by cooling. Preferably the temperature is from 20° C. to 75° C. Renaturation can be accelerated by the addition of polyethylene glycol ("PEG") or salt. A suitable salt concentration may range from 0 mM to 200 mM. The annealed nucleic acid fragments are next incubated in the presence of a nucleic acid polymerase and dNTP's (i.e. dATP, dCTP, dGTP and dTTP). The nucleic acid polymerase may be the Klenow fragment, the Taq polymerase or any other DNA polymerase known in the art. The polymerase may be added to the random nucleic acid fragments prior to annealing, simultaneously with annealing or after annealing. The cycle of denaturation, renaturation and incubation in the presence of polymerase is repeated for a desired number of times. Preferably the cycle is repeated from 2 to 50 times, more preferably the sequence is repeated from 10 to 40 times. The resulting nucleic acid is a larger double-stranded polynucleotide of from about 50 bp to about 100 kb and may be screened for expression and altered activity by standard cloning and expression protocol. (Maniatis supra).

Methods of Use: Altering Phenylpropanoid Metabolism

The vectors used to transform plant cells comprise an REF8 nucleic acid or portion thereof which is capable of hybridizing with the endogenous REF8 gene of *Arabidopsis* or other species. Such nucleic acids include the sense or antisense strands of the ref8 gene or REF8 gene encoding all or part of a protein. In either case, the REF8 nucleic acid or its transcript is capable of hybridizing with an endogenous REF8 gene as defined herein or its transcript. The conditions under which such hybridization occurs include the physiological or equivalent conditions found within plant cells including that found in the nucleus and cytoplasm as well as standard in vitro conditions normally used by the skilled artisan to determine sequence homology as between two nucleic acids. Such in vitro conditions range from moderate (about 5×SSC at 52° C.) to high (about 0.1×SSC at 65° C.) stringency conditions.

The REF8 gene is used to construct sense or antisense vectors for transforming plant cells. The construction of such vectors is facilitated by the use of a binary vector which is capable of manipulation and selection in both a plant and a convenient cloning host such as a prokaryote. Thus, such a binary vector can include a kanamycin or herbicide resistance gene for selection in plant cells and an actinomycin resistance gene for selection in a bacterial host. Such vectors, of course, also contain an origin of replication appropriate for the prokaryotic host used, and preferably at least one unique restriction site or a polylinker containing unique restriction sites to facilitate vector construction.

In one embodiment, a constitutive promoter is used to drive expression of the REF8 nucleic acid within at least a portion of the reproductive tissues in the recipient plant. A particularly preferred promoter is the cauliflower mosaic virus 35S transcript promoter (Guilley et al. (1982), Odell et al. (1985), and Saunders et al. (1987)). However, other constitutive promoters can be used, such as the ∝-1 and β-1 tubulin promoters (Silflow et al. (1987)) and the histone promoters (Chaubet et al. (1987)). Other promoters which can be used to provide tissue and temporal specificity to the expression of the REF8 nucleic acid include xylem-specific promoters.

In a further embodiment of the invention, the vector used to transform the *Arabidopsis* cell to produce an *Arabidopsis* having altered secondary metabolism is constructed to target the insertion of the REF8 nucleic acid into an endogenous promoter within a plant cell. One type of vector which can be used to target the integration of an REF8 nucleic acid to an endogenous promoter comprises a positive-negative selection vector analogous to that set forth by Monsour et al. (1988), which describes the targeting of exogenous DNA to a predetermined endogenous locus in mammalian ES cells. Similar constructs utilizing positive and negative selection markers functional in plant cells can be readily designed based upon the identification of the endogenous plant promoter and the sequence surrounding it (Kempin et al. (1997)). When such an approach is used, it is preferred that a replacement-type vector can be used to minimize the likelihood of reversion to the wild-type phenotype.

The vectors of the invention are designed such that the promoter sequence contained in the vector or the promoter sequence targeted in the plant cell genome are operably linked to the nucleic acid encoding the REF8 gene. When the positive strand of the ref8 gene is used to express all or part of the ref8 protein, the term "operably linked" means that the promoter sequence is positioned relative to the coding sequence of the nucleic acid such that RNA polymerase is capable of initiating transcription of the ref8 nucleic acid from the promoter sequence. In such embodiments it is also preferred to provide appropriate ribosome binding sites, transcription initiation and termination sequences, translation initiation and termination sequences and polyadenylation sequences to produce a functional RNA transcript which can be translated into C3H polypeptide. When an antisense orientation of the REF8 nucleic acid is used, all that is required is that the promoter be operably linked to transcribe the REF8 antisense strand. Thus, in such embodiments, only transcription start and termination sequences are needed to provide an RNA transcript capable of hybridizing with the mRNA or other RNA transcript from the endogenous REF8 gene. In addition to promoters, other expression regulation sequences, such as enhancers, can be added to the vector to facilitate the expression of REF8 nucleic acid in vivo.

Once a vector is constructed, the transformation of plants can be carried out in accordance with the invention by essentially any of the various transformation methods known to those skilled in the art of plant molecular biology. Such methods are generally described in Wu and Grossman (1987). As used herein, the term "transformation" means the alteration of the genotype of a plant cell by the introduction of a nucleic acid sequence. Particular methods for transformation of plant cells include the direct microinjection of the nucleic acid into a plant cell by use of micropipettes. Alternatively, the nucleic acid can be transferred into a plant cell by using polyethylene glycol (Paszkowski et al. (1984)). Other transformation methods include electroporation of protoplasts (Fromm et al. (1985); infection with a plant specific virus, e.g., cauliflower mosaic virus (Hohn et al. (1982)) or use of transformation sequences from plant specific bacteria such as *Agrobacterium tumefaciens*, e.g., a Ti plasmid transmitted to a plant cell upon infection by *Agrobacterium tumefaciens* (Horsch et al. (1984); Fraley et al. (1983)). Alternatively, plant cells can be transformed by introduction of nucleic acid contained within the matrix or on the surface of small beads or particles by way of high velocity ballistic penetration of the plant cell (Klein et al. (1987)). The nucleic acid introduced with ballistics may be a chimeric oligonucleotide designed to target a small number of mutated bases to a selected segment of the endogenous REF8 gene (Beetham et al. (1999)). A small number of mutated bases can also be introduced into a selected segment of the endogenous REF8 gene using homologous recombination (Kempin et al. (1997)).

After the vector is introduced into a plant cell, selection for successful transformation is typically carried out prior to regeneration of a plant. Such selection for transformation is not necessary, but facilitates the selection of regenerated plants having the desired phenotype by reducing wild-type background. Such selection is conveniently based upon the antibiotic resistance and/or herbicide resistance genes which may be incorporated into the transformation vector.

Practically all plants can be regenerated from cultured cells or tissues. As used herein, the term "regeneration" refers to growing a whole plant from a plant cell, a group of plant cells or a plant part. The methods for plant regeneration are well known to those skilled in the art. For example, regeneration from cultured protoplasts is described by Evans et al. (1983); and H. Binding (1985). When transformation is of an organ part, regeneration can be from the plant callus, explants, organs or parts. Such methods for regeneration are also known to those skilled in the art. See, e.g., Wu and Grossman (1987); Weissbach and Weissbach (1986); and Klee et al. (1987).

Once plants have been regenerated, one or more plants are selected based upon a change in phenylpropanoid metabolism. Such selection can be by TLC, HPLC, GC or other means known in the art.

Either antisense or co-suppression mechanisms using REF8 nucleic acids can result in altered phenylpropanoid metabolism in many species. In addition, plants having such altered metabolism can be used as model systems for further study of the phenylpropanoid pathway in plants.

Alternatively, phenylpropanoid metabolism may be deterred by virus induced gene silencing (VIGS) using techniques known in the art (Baulcombe, 1999). Use of VIGS suppresses gene expression in plants in a sequence-specific manner by infection with virus vectors carrying fragments of host REF8 genes. As another alternative, phenylpropanoid metabolism may be modified through the identification of mutans in which the endogenous REF8 gene has been inactivated through processes including but not limited to t-DNA tagged (Winkler, et al., 1998) or transposon mutagenesis (Hanley, et al., 2000; Enoki, et al., 1999) using techniques known in the art. Mutants of this type would be expected to have decreased endogenous C3H polypeptide activity, and desirable characteristics like those described for the ref8 mutant.

General Methods

Standard recombinant DNA and molecular cloning techniques used in the Examples are well known in the art and are described by Maniatis and by Silhavy, et al. (1984) and by Ausubel, et al. (1987).

Materials and methods suitable for the maintenance and growth of bacterial cultures are well known in the art.

Techniques suitable for use in the following examples may be found as set out in *Manual of Methods for General Bacteriology* (Gerhardt, et al., eds., 1994) or by Brock (1989). All reagents, restriction enzymes and materials used for the growth and maintenance of bacterial cells were obtained from Aldrich Chemicals (Milwaukee, Wis., DIFCO Laboratories (Detroit, Mich.), GIBCO/BRL (Gaithersburg, Md.), or Sigma Chemical Company (St. Louis, Mo.) unless otherwise specified.

Manipulations of genetic sequences were accomplished using the suite of programs available from the Genetics Computer Group Inc. (Wisconsin Package Version 9.0, Genetics Computer Group (GCG), Madison, Wis.). Where the GCG program "Pileup" was used the gap creation default value of 12, and the gap extension default value of 4 were used. Where the CGC "Gap" or "Bestfit" programs were used the default gap creation penalty of 50 and the default gap extension penalty of 3 were used. In any case where GCG program parameters were not prompted for, in these or any other GCG program, default values were used.

Plant Material

*Arabidopsis thaliana* L. Heynh. ecotype Columbia were cultivated at a light intensity of 100 mE $m^{-2}sec^{-1}$ at 23° C. under a photoperiod of 16 h light/8 h dark in Redi-Earth potting mix (Scotts-Sierra Horticultural Products; Marysville, Ohio).

Sinapate Ester Analysis

For analysis of sinapate esters, tissue was extracted in 50% methanol containing 1.5% (v/v) acetic acid and analyzed by reverse phase HPLC. Leaf extracts were separated on a Microsorb-MV C18 column (Ranin Instruments, Woburn, Mass.) using a gradient from 1.5% phosphoric acid to 35% acetonitrile in 1.5% phosphoric acid at a flow rate of 1 mL $min^{-1}$. Seed extracts were separated on a Puresil C18 column (Waters, Milford Mass.) using a gradient from 1.5% acetic acid, 0.05% SDS to 30% acetonitrile in 1.5% acetic acid, 0.05% SDS at a flow rate of 1 mL $min^{-1}$. To identify the phenolic component of esters accumulated in leaf and seed extracts, samples were hydrolyzed in 1 M NaOH for 2 hr at room temperature, acidified, and the liberated hydroxycinnamic acids were extracted into ethyl acetate and dried in vacuo. Samples were redissolved in 50% methanol and separated on a Microsorb-MV C18 column using a gradient from 5% acetic acid to 25% acetonitrile in 20% acetic acid at a flow rate of 1 mL $min^{-1}$.

Cell Wall Analysis

Figure 5:
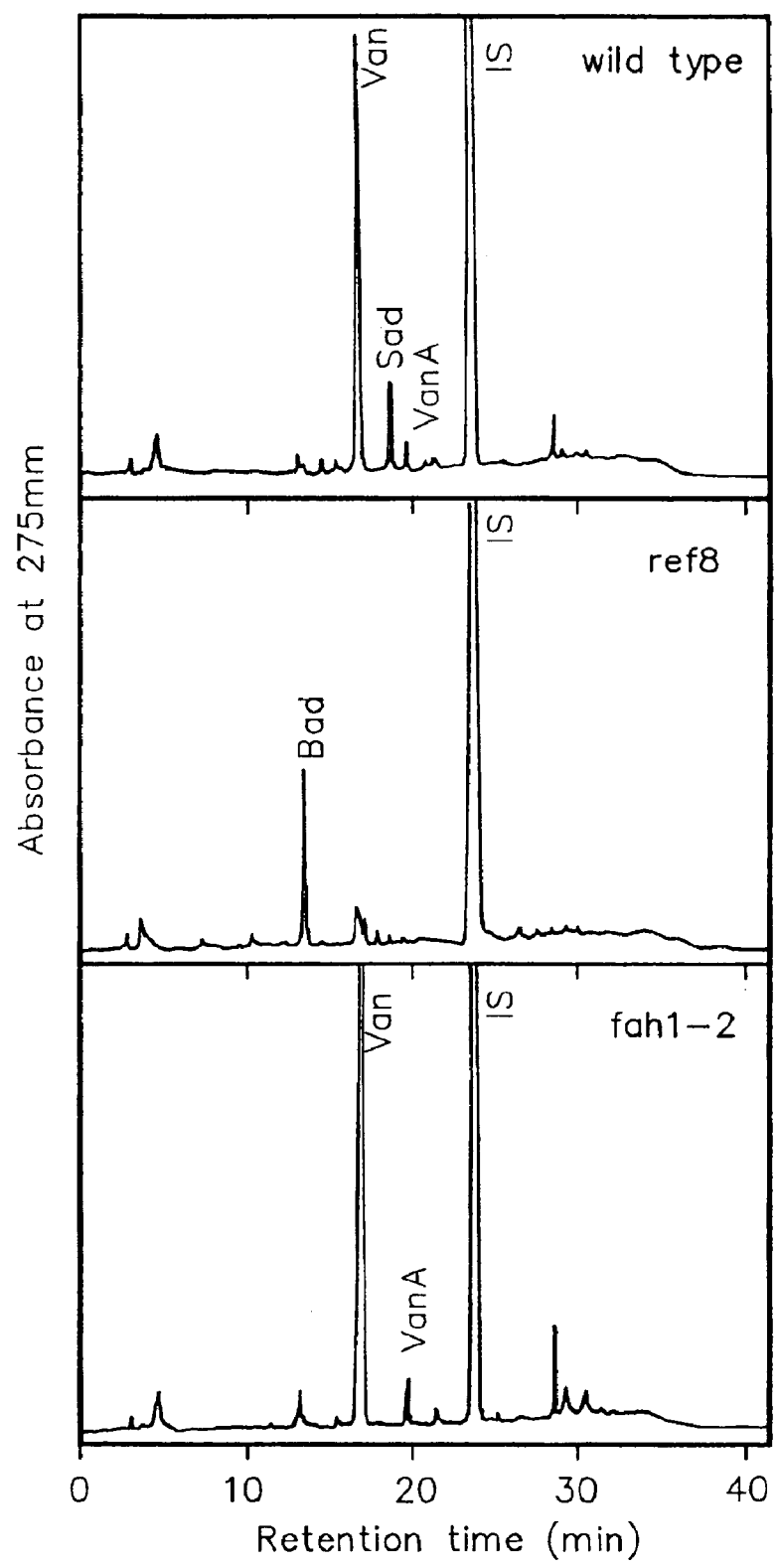
FIG. 5 shows nitrobenzene oxidation products of rachis lignin for wild-type, ref8 and fah-1 as analyzed by HPLC. IS, internal standard (3-ethoxy-4-hydroxybenzaldehyde); Bad, p-hydroxybenzaldehyde; Sad, syringealdehyde; Van, vanillin, VanA, vanillic acid.

For cell wall preparation, *Arabidopsis* rachis (stem) tissue was ground to a fine powder and extracted with neutral phosphate buffer, 80% ethanol and acetone (Meyer et al., 1998). Cell wall esterified phenolics were released by saponification with 1 M NaCH for 16 h at room temperature, and hydrolysis products were extracted in ethyl acetate and separated by reverse phase HPLC using detection at 320 or 275 nm. To measure lignin content, cell wall samples saponified as described above were analyzed using the TGA method (Campbell and Ellis, 1992), or the microscale Klason method (Kaar et al., 1991). Lignin monomer composition of saponified cell walls was determined by nitrobenzene oxidation (Meyer et al., 1998) the DFRC method (Lu and Ralph, 1997) modified as previously described (Franke et al., 2000), and by Py-GC-MS (Bocchini et al., 1997) (FIG. 5). NBO reactions were first extracted with dichloromethane to remove nitrobenzene, after which reaction products were extracted into diethyl ether and analyzed by HPLC. DFRC products were quantified by comparison to authentic standards using GC-MS and selective ion monitoring.

Pyrolysis of the stem tissue was performed using Shimadzu PYR-4A pyrolyzer and analyzed by GC-MS (QP- 5050A, Shimadzu, Columbia, Md, USA). Pyrolysis was performed at 500° C. with the column inlet temperature maintained at 300° C. Chromatographic separation was performed using a 30 m Rtx-5 ms column (0.25 mm i.d.; 0.25 μm film thickness). The column flow was 1 mL min$^{-1}$ with a 1:100 split ratio. The oven temperature program was 40° C. for 10 min, 5° C. min$^{-1}$ ramp to 280° C. and 280° C. for 5 min (total run time of 63 minutes). The GC-MS interface temperature was held at 280° C. the mass spectrometric analysis of the column eluent began at 4.00 minutes and concluded at 50 minutes. All lignin degradation products eluted prior to 45 minutes. The mass analyzer was scanned from 50 to 410 Da at a scan speed of 2000 Da sec$^{-1}$. Approximately 0.8 mg of stem tissue and 1.6 μg of the internal standard, 1,3,5-tri-t-butylbenzene were analyzed.

To determine the digestibility of wild-type and ref8 cell walls, tissue samples were treated with Driselase (Sigma, St. Louis Mo.), a crude mixture of endo- and exo-glucanases. Solvent-extracted cell walls (100 mg) were suspended in 1% Driselase in 50 mM pyridinium acetate buffer, pH 4.7, and incubated for 3 days at 37° C. The undigested cell wall residue was precipitated by centrifugation (1000×g, 5 min) and the supernatant was discarded. The pellet was washed twice with 50 mM pyridinium acetate buffer, pH 4.7 and the Driselase digestion was repeated for an additional 2 days. The undigested residue was collected by centrifugation, washed with 50 mM pyridinium acetate buffer, water, 3% (w/v) SDS in 1% (w/v) ammonium bicarbonate, water, and acetone and was dried overnight at room temperature before weighing.

Histochemistry

Six week old rachis internodes were fixed, dehydrated, and embedded in Spurr's resin. One μm cross sections were stained with Toluidine blue O and observed under bright field microscopy.

O-methyltransferase Enzyme Assays

Protein extracts were prepared and COMT and CCoAOMT activity were measured as described previously (Inoue et al., 1998). Total protein content was measured using the Pierce BCA assay using bovine serum albumin as a standard.

Ethylene Measurements

Rosettes of 4 week old plants were harvested, weighed, and incubated under ambient laboratory lighting in a sealed 5 mL scintillation vial for 90 min. Ethylene content of the gas phase was measured as described previously (Jones and Woodson, 1999).

Radiotracer Feeding Experiments

U-$^{14}$C-L-phenylalanine was administered to individual illuminated leaves of wild-type and mutant plants for 3 h before extraction in methanol at 60° C. in the presence of unlabeled hydroxycinnamic acids, as described previously (Chapple et al., 1992). Extracts were analyzed directly or after saponification for 30 min. in 1 M NaOH followed by acidification and extraction of the radiolabeled products into diethyl ether. Extract components were resolved by a two-dimensional silica gel TLC system that separates all of the natural hydroxycinnamic acids (solvent 1, petroleum ether/ethyl acetate/methanol/acetic acid 10:10:1:0.2; solvent 2, toluene/acetic acid/water 2:1:sat.). Incorporation of label into pathway intermediates was determined using a Packard Instant Imager. To measure the incorporation of label from U-$^{14}$C-L-phenylalanine specifically into caffeic acid, an identical feeding experiment was conducted; however, prior to analysis, the extract was incubated in methanolic HCl (80° C., 1 h) to convert caffeic acid and its ester conjugates to caffeic acid methylester. Methylcaffeate was purified by semi-preparative silica gel TLC using the two solvents described above. Following each round of TLC, the band of methylcaffeate was identified under UV light, scraped from the TLC plate, eluted in methanol, and after the second round of TLC, analyzed by reversed phase HPLC (solvent A, 5% acetic acid in water; solvent B, 20% acetic acid, 25% acetonitrile in water; 5 to 55% B in 20 min, 55 to 100% B in 10 min, 100% B for 5 min; flow rate 1 mL min$^{-1}$) using diode array UV detection. One mL fractions were collected and analyzed for radioactivity by liquid scintillation counting.

Map-based Cloning

The ref8 mutant (Columbia background) was used as the male parent in a cross to the Landsberg erecta ecotype. $F_1$ individuals were allowed to self-pollinate, and $F_2$ plants were screened for the ref8 phenotype. Because ref8 plants are small in stature and are female sterile, seeds from phenotypically wild-type plants (REF8/ref8 and REF8/REF8 individuals) were collected and the $F_3$ progeny were scored for segregation of the ref8 phenotype. DNA was extracted (Doyle and Doyle, 1990) from homozygous wild-type lines for ARMS mapping (Schaffner, 1996) to determine an initial map position for the REF8 gene. Subsequently, DNA was extracted from additional $F_2$ plants and $F_3$ families for use in PCR-based genotyping experiments. Individuals carrying recombinant chromosomes in the region of the REF8 locus were used to determine a mapping interval for the gene, and were analyzed further.

RNA Gel Blot Analysis

For the isolation of RNA, plant tissues were harvested, frozen in liquid nitrogen, and stored at −70 C. until ready for extraction. Total RNA was isolated as previously described (Goldsbrough and Cullis, 1981). Samples were electrophoretically separated, transferred to Hybond N+ membranes (Amersham), hybridized at 65 C. with a DNA probe (DECAprime II system, Ambion) using a CYP98A3 EST ordered from the *Arabidopsis* Biological Resource Center (209A1T7; Genbank accession number N37715), washed, and exposed to film.

Isolation of the Ref8 cDNA

The ref8 cDNA was isolated by reverse transcriptase-PCR from total RNA using the Promega Access RT-PCR system (Madison, Wis.) using primer 1 (5'-gcaaggatccatgtcgtggtttctaatagcg-3') and primer 2 (5'-tcaggaattcatttacatatcgtaaggcacg-3'). These primers correspond to the 5' and 3' ends of the open reading frame and introduce a BamHI site upstream of the start codon and an EcoRI site downstream of the stop codon, respectively for use in subsequent yeast expression studies. Two independent reaction products were subcloned and sequenced to identify the mutation in the ref8 allele.

Heterologous Expression

To generate the pBOV *E. coli* P450 expression plasmid, pCWOri+ was first digested with HindIII and NdeI and purified by gel electrophoresis. The overlapping complementary primers 3 (5'-tatggctctgttattagcagttttata-3'), 4 (5'-caggcctataaaaactgctaataacagagcca-3'), 5 (5'-ggcctgcatgccatcatcatcatcatcattag-3'), and 6 (5'-agctctaatgatgatgatgatgatggcatg-3') were then phosphorylated using polynucleotide kinase and ligated into the pCWOri+ vector backbone. The resulting cloning site in the plasmid contains the first eight codons of the bovine CYP17 gene followed by a StuI site for the blunt-ended cloning of PCR-amplified P450 cDNAs, a downstream SphI site, a sequence coding for a 6×-His tag, and a stop codon.

Using the CYP98A3 EST as a template for PCR, the pBOV-REF8 plasmid was generated by first using primer 7

(5'-gacaatcgccgccgtcgtatcctac-3') and primer 8 (5'-catatcgtaaggcacgcgtttgtac-3') to produce a truncated version of the open reading frame that lacked the first nine codons of the protein's N-terminal signal peptide. This PCR product was subcloned into StuI-digested pBOV, the orientation of the insert was determined using diagnostic restriction digests, and the fidelity of the PCR process was verified by sequencing. To generate the pBOV-ref8 plasmid, the CYP98A3 EST was used in two separate reactions using primer 7 with primer 9 (5'-cggtgcacaacttgatatcaatttgg-3') and primer 6 with primer 10 (5'-ccaaattgatatcaagttgtgcaccg-3') to introduce the ref8 mutation (underlined in primers 9 and 10) into each of two overlapping fragments of the cDNA. The PCR products were purified by agarose gel electrophoresis, combined in a single PCR reaction, and amplified using only primers 7 and 6. The resulting full length product was subcloned into pBS KS-, sequenced, and a StyI/SphI fragment containing the ref8 mutation was used to replace the corresponding portion of pBOV-REF8 to yield pBOV-ref8.

The construction of the *Saccharomyces* cerevisiae strain WAT11, a derivative of the W303-B strain (MAT a; ade2-1; his3-11, -15; leu2-3, -112; ura3-1; can$^R$; cyr$^+$) expressing the ATR1 *Arabidopsis* NADPH-P450 reductase, was previously described (Truan et al., 1993; Pompon et al., 1996). For the construction of the YeDP60-REF8 expression construct, the CYP98A3 EST was used as the template for PCR as described above with primer 1 and primer 2. The resulting 1.5 kb PCR product was subcloned, sequenced, and ligated into BamHI/EcoRI digested pYeDP60 (Urban et al., 1990) to yield the plasmid YeDP60-REF8. To generate the plasmid YeDP60-ref8, PCR using the CYP98A3 EST was conducted in two separate reactions using primer 1 with primer 9 and primer 2 with primer 10 to introduce the ref8 mutation into each of two overlapping fragments of the cDNA. The PCR products were purified by agarose gel electrophoresis, combined in a single PCR reaction, and amplified using only primers 1 and 2. The resulting full length product was subcloned into pBS KS-, sequenced and subcloned into YeDP60 as described above.

Measurement of Enzmatic Activity in Vivo

WAT11 cells were transformed with pYeDP60, pYeDP60-REF8, and pYeDP60-ref8 (Gietz et al., 1992), cultured and then induced with galactose as described previously (Urban et al., 1994). For in vivo measurements of enzyme activity, cells were grown in media supplemented with 5 mM p-coumaric acid. At the end of the incubation period the medium was extracted with ethylacetate, and analyzed by HPLC as described above. SDS-PAGE analysis of heterologously expressed C3H and in vitro C3H assays were performed as described previously for measurement of ferulate 5-hydroxylase activity (Humphreys et al., 1999).

Measurement of Enzmatic Activity in Vitro

For C3H assays, an NADPH regenerating system consisting of 1 mM NADP$^+$, 10 mM glucose-6-phosphate, and 1 unit glucose-6-phosphate dehydrogenase was pre-incubated at 30 C for 5 min to permit the generation of NADPH in the presence of one of the putative C3H substrates in a final volume of 400 μL of assay buffer. Assays were initiated by the addition of 100 μL of microsomes and were allowed to incubate for 60 min at 30C before being terminated by boiling. Assays were clarified by centrifugation for 20 min at 13,000 xg, and were analyzed directly by HPLC on a Microsorb-MV C-18 column (Rainin, Woburn Mass.) using a gradient of solvent A (1.0% acetic acid in water) and solvent B (acetonitrile; 0 to 10% B in 5 min, 10 to 25% B in 25 min; flow rate 1 mL min$^{-1}$). C3H reaction products were quantified using UV detection (caffeic acid, 322 nm; caffeyl aldehyde, 340 nm; caffeic acid methyl ester, 324 nm). Assays conducted using microsomes isolated from yeast transformed with pYeDP60 served as negative controls. The apparent $K_m$ for p-coumarate methyl ester was determined using triplicate assays analyzed by the Eadie-Hofstee method (Cornish-Bowden, 1995).

GC-MS

Analysis of C3H reactions products was performed using a GC-MS system (Shimadzu Corp. Kyoto, Japan) composed of an AOC-20 autosampler, a GC-17A gas chromatograph, and a GCMS-QP5050A mass spectrometer. A standards solution was prepared from methanolic stock solutions of the substrates and products. Aliquots of each stock solution were taken in order to obtain a solution having approximately 1000 pmol L$^{-1}$ of each standard. The standards solution and the assay samples were dried on a RC 10.10 centrifugal evaporator (Jouan, Winchester Va.) resuspended in 100 and 50 L of pyridine, respectively and derivatized using 10 and 5 L N-methyl-N-trimethylsilyltrifluoroacetamide (MSTFA), respectively, at 37 C for 30 minutes. A one microliter aliquot of each sample was injected into the GC-MS with the split ratio set to 1:25. Helium was used as the carrier gas with a flow rate of 1 mL min$^{-1}$. The injector temperature was maintained at 220 C. Gas chromatography was performed using a 30 m DB-5MS column (0.25 mm I.D., 0.25 m film thickness) (J&W Scientific, Folsom Calif.). The column temperature was initially maintained at 125 C for 2 minutes and then ramped at 15 C/min to 250 C and held for 4 minutes. The interface temperature was held at 280 C. After a 4.95 minute solvent cut time, detection was performed using a single quadrupole mass filter set to scan from mass-to-charge 50 to 410 in 0.17 seconds.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Evaluation of Phenylpropanoid Metabolism in ref8 Mutant

To identify mutants defective in sinapoylmalate biosynthesis, approximately 100,000 M$_2$ seedlings (Columbia ecotype) were screened for individuals that exhibited altered cotyledon and/or leaf fluorescence when exposed to UV light. This mutant screen identified representatives of two known mutations that are affected in sinapate ester biosynthesis, fahl and sngl, as well as a number of additional mutant lines that define several other loci. Five of these have been phenotypically characterized (Ruegger and Chapple, in press), whereas the others have not, largely due to issues associated with vigor and fertility of the M$_2$ plants and their progeny. The ref8 mutant was one belonging to this latter group.

When observed under UV light, the ref8 mutant is strongly red fluorescent, consistent with the absence of sinapoylmalate, and the accentuation of chlorophyll fluorescence that accompanies the lack of this UV-absorbing secondary metabolite. Visible phenotypes of the ref8 mutant.

(a) UV phenotype of the ref8 mutant. Rosette leaves of three week old plants were photographed under 365 nm UV light using a yellow barrier filter. The blue-green color of the wild-type rosettes is due to the fluorescence of sinapoyl-malate. The red fluorescence of the ref8 plant is due to chlorophyll fluorescence that is revealed in the absence of sinapate ester fluorescence. (b) The developmental phenotype of the ref8 mutant. Wild-type and ref8 plants were grown for 6 weeks under a 16 h light/8 h dark photoperiod at 22° C. When $F_2$ seedlings from crosses of ref8 mutants to wild type were examined, the mutant phenotype segregated as a recessive, nuclear, single gene mutation (405 REF8/-, 138 ref8/ref8;$^2$=0.04, P>0.7).

The profile of soluble secondary metabolites is altered in the ref8 mutant. The ref8 mutant looks similar to the fah1–2 mutant when observed under UV light, suggesting that the mutation leads to substantial reductions in leaf sinapoyl-malate content. Since not all phenolic compounds are fluorescent, it was not clear by this visual inspection whether ref8 leaves were devoid of phenylpropanoid esters, or whether they only accumulated non-fluorescent pathway products. To distinguish between these two possibilities, we analyzed extracts of three-week-old rosettes by HPLC (FIG. 1a) HPLC analysis of soluble secondary metabolites produced by wild-type and ref8 plants. (FIG. 1a) Compounds found in wild-type and ref8 leaves were extracted with methanol and analyzed by HPLC. The elution of UV-absorbing compounds was monitored at 320 nm. (FIG. 1b) Hydroxycinnamic acids released from their ester conjugates by saponification (1M NaOH, 16 h, room temperature) of the methanolic extract of (a). (FIG. 1c) The same analyses as (a) performed on wild-type and ref8 seed extracts. Sinmal, sinapoylmalate; Singlc, sinapoylglucose; Sincho, sinapoylcholine.

Figure 1B:
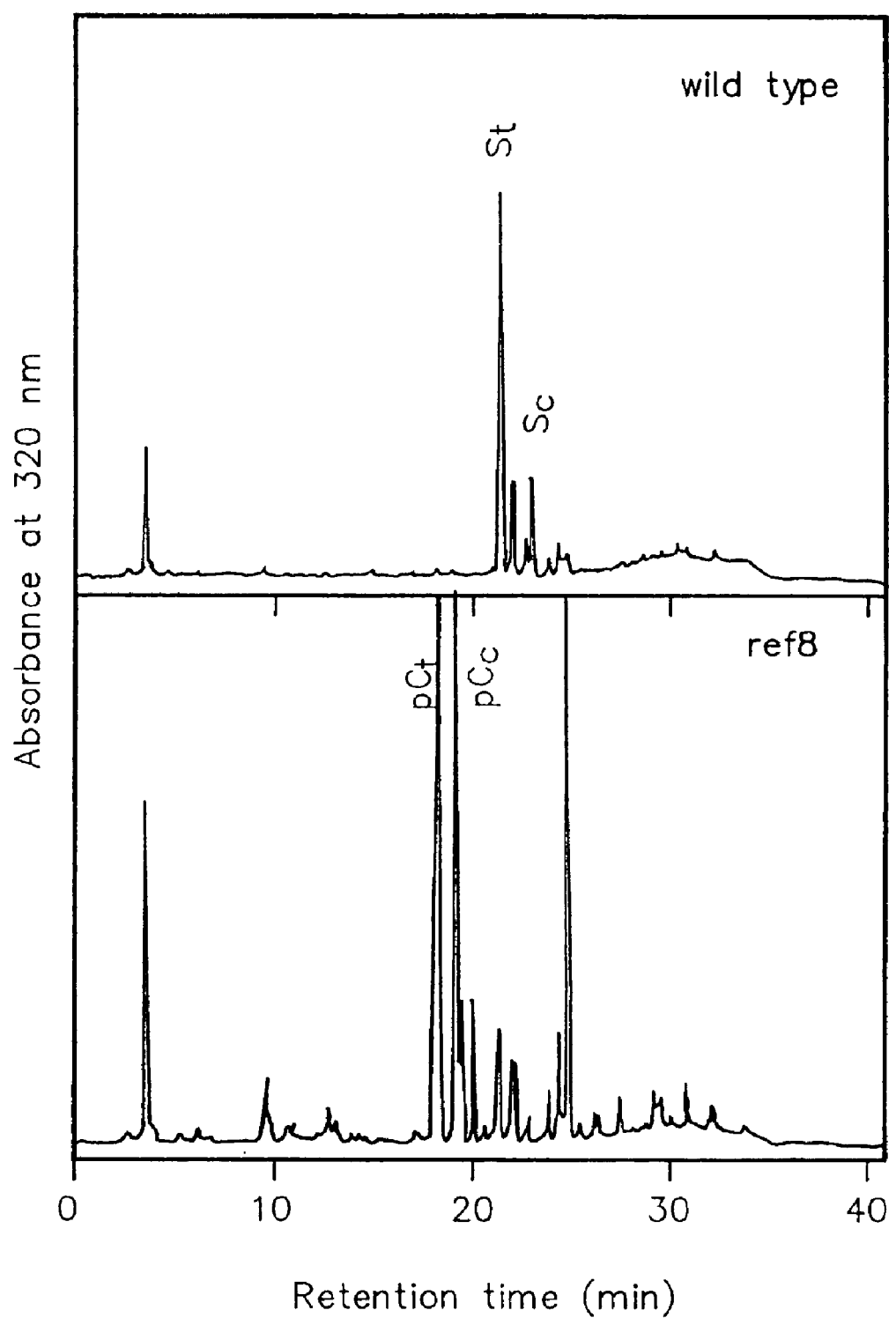

This analysis confirmed that ref8 leaves lack sinapoylmalate, and indicated that ref8 mutants instead accumulate an array of other, apparently non-fluorescent, soluble secondary metabolites that absorb UV light at 320 nm. As a first step toward the identification of these compounds, leaf extracts were saponified and the hydrolysates were then characterized by HPLC. These analyses indicated that whereas the predominant hydroxycinnamic acid in saponified extracts of wild-type plants was sinapic acid, extracts of ref8 contained little sinapic acid and substantial quantities of the cis and trans isomers of p-coumaric acid (FIG. 1b). This finding suggests that the UV-absorbent compounds present in ref8 leaves are likely to include esters of p-coumaric acid.

Figure 1C:
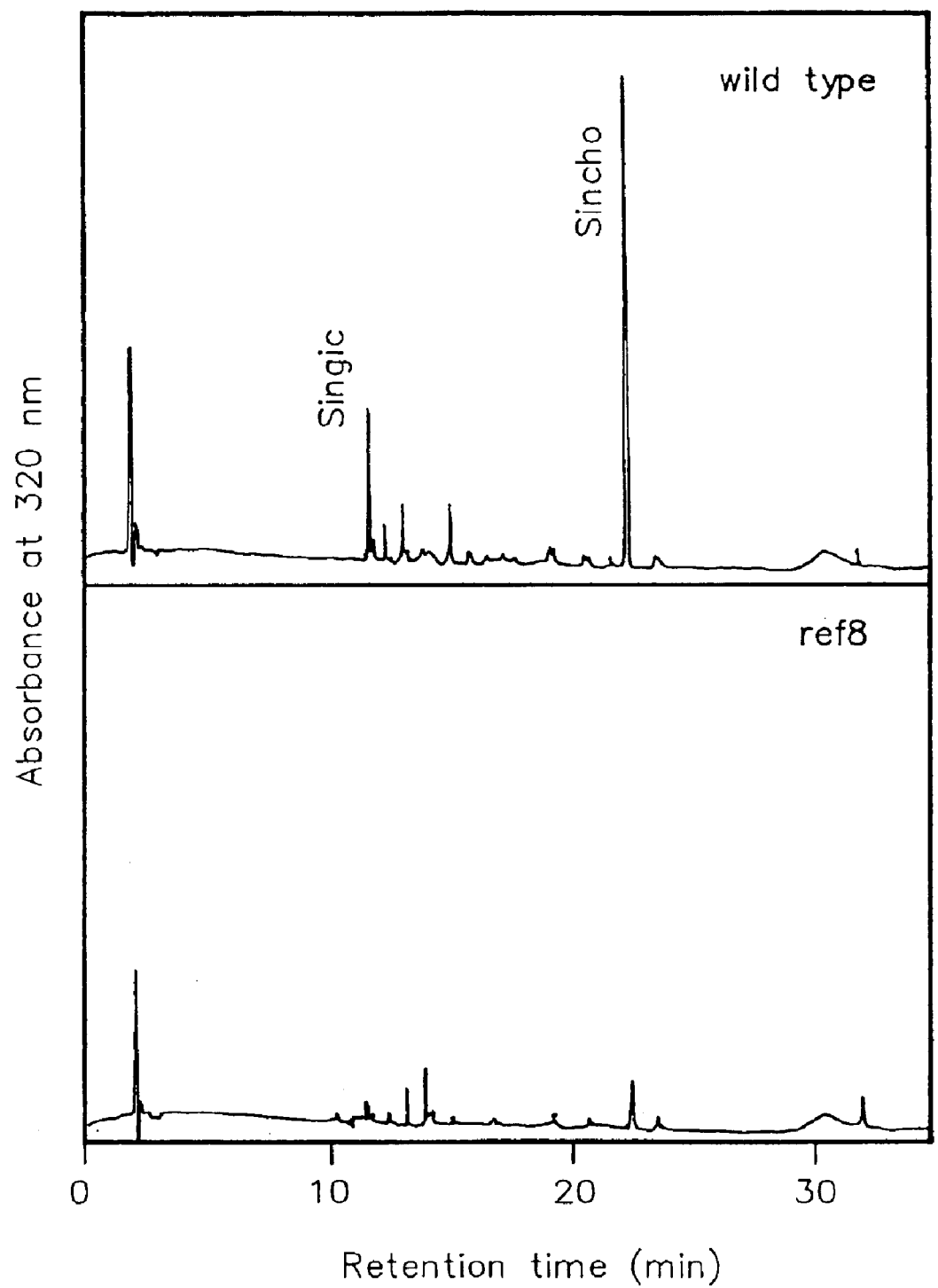
Figure 2A:
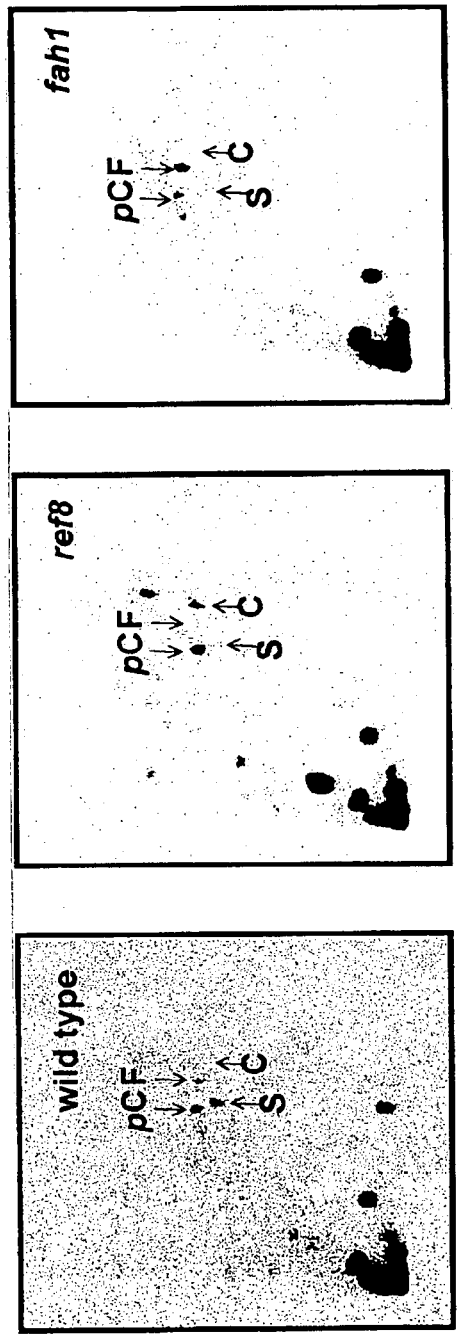
FIGS. 2A–B show analysis of phenylpropanoid synthesis in wild-type and ref8 leaves using radiotracer feeding technology. $^{14}$C-L-Phenylalanine was administered to individual illuminated leaves of wild-type and mutant plants for 3 h before extraction in 60° C. MeOH in the presence of unlabeled hydroxycinnamic acids. A) Two dimensional silica-gel TLC (solvent 1, petroleum ether/ethyl acetate/methanol/acetic acid 10:10:1:0.2; solvent 2, toluene/acetic acid/water 2:1:sat.) of the methanolic extract followed by autoradiography to identify the radiolabeled metabolites synthesized. B) Similar analyses performed after the methanolic extract from the previous experiment was saponified to release ester-bound phenolic acids C, cinnamic acid; pC, p-coumaric acid; F, ferulic acid; S, sinapic acid.
Figure 2B:
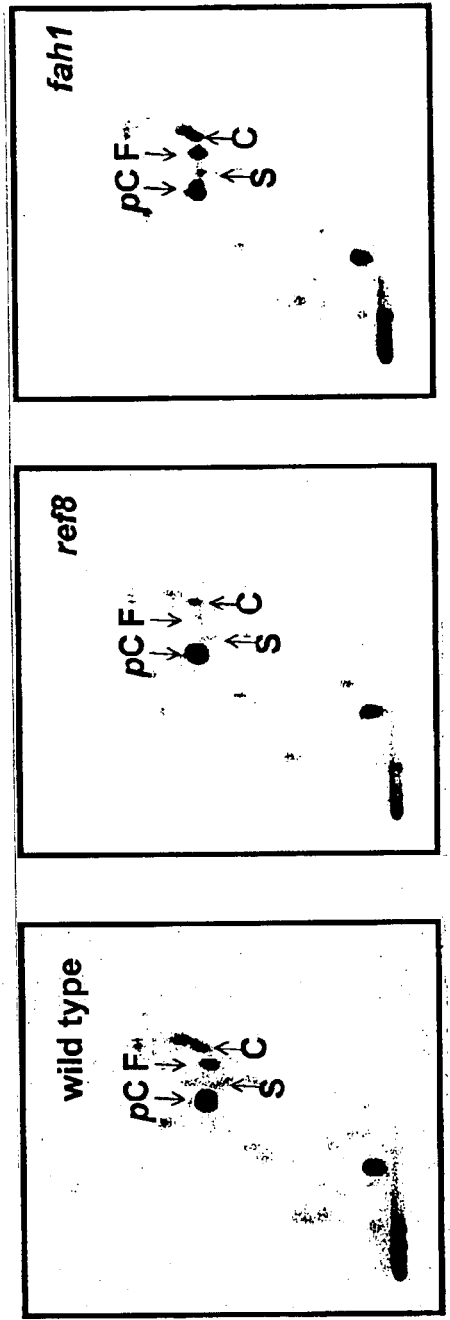

In addition to the sinapoylmalate found in leaf tissue, *Arabidopsis* accumulates sinapoylcholine and to a lesser extent, sinapoylglucose in its seeds. To evaluate the impact of the ref8 mutation on seed secondary metabolism, extracts were prepared from mutant and wild-type seeds and were analyzed by HPLC (FIG. 1c). The most striking difference between the two genotypes was the lower overall content of UV-absorbing metabolites in ref8 samples. Sinapoylglucose and sinapoylcholine were identified in wild-type seed extracts, and although minor peaks co-chromatographing with these compounds were observed in ref8 extracts, a number of other minor novel peaks were also found in the mutant samples (FIG. 1c). When wild-type and ref8 seed extracts were saponified, the major hydroxycinnamic acids recovered in the hydrolysates were identified by HPLC as sinapic and p-coumaric acids, respectively, suggesting that novel p-coumaroyl esters are accumulated in ref8 seeds.

Because flavonoids constitute another important class of phenylpropanoid metabolites, we scored ref8 plants for their ability to accumulate flavonoid derivatives including anthocyanins and seed coat condensed tannins. Anthocyanins can readily be observed as red-colored pigments accumulating in leaf tissue of the mutant, and in the epidermis of the lower portions of the rachis. Similarly, the seeds of the ref8 mutant are brown, indicating that the mutation does not disrupt the flavonoid pathway in the testa. Taken together, these phenotypes indicate that the steps of phenylpropanoid pathway from phenylalanine to p-coumaroyl CoA and flavonoid biosynthesis remain unaffected in the ref8 mutant, and suggest that ref8 plants are defective in one of the steps required for the conversion of p-coumarate to sinapate.

To investigate where phenylpropanoid metabolism is blocked in the ref8 mutant, we evaluated the fate of $^{14}$C-L-phenylalanine administered to wild-type and ref8 leaves via the transpiration stream. These experiments revealed that radiolabeled pools of cinnamic, p-coumaric, ferulic and sinapic acids can be detected in the extracts of wild-type plants. In extracts of the ref8 mutant, radiolabel was detected in cinnamic acid and p-coumaric acid, but not in any subsequent metabolites. In neither wild type nor ref8 was radiolabel found to be associated with caffeic acid or 5-hydroxyferulic acid, possibly indicating that the pools of these intermediates are below the detectable limits of this method. Since hydroxycinnamic acids are often found in esterified forms in plants, and hydroxy-cinnamoyl CoA thioesters are thought to comprise an important group of molecules in plant metabolism, samples of the previous extracts were saponified and again separated by two-dimensional thin layer chromatography (TLC). These analyses provided qualitatively similar data: the ref8 extract hydrolysates contained no radiolabeled ferulic acid, but wild-type levels of labeled p-coumaric acid.

The inability of the ref8 mutant to convert $^{14}$C-phenylalanine into ferulic acid is consistent with the hypothesis that the mutant is blocked in either the hydroxylation of p-coumaric acid, the O-methylation of caffeic acid to ferulic acid, or the analogous reactions occurring at the level of the corresponding CoA thioesters. To distinguish between these possibilities, we compared the levels of caffeic acid/5-hydroxyferulic acid O-methyl transferase (COMT) and caffeoyl CoA O-methyltransferase (CCoAOMT) in wild-type and ref8 stem extracts. These experiments revealed that the two O-methyltransferase activities were present at near wild-type levels in ref8 (Table 2). Although these data suggested that O-methylation of caffeic acid and caffeoyl-CoA are not affected in the ref8 mutant, we wanted to determine whether the supply of the co-substrate of the O-methyltransferase reaction, S-adenosylmethionine (SAM), might be limiting phenylpropanoid metabolism in the ref8 mutant. As an indirect measure of SAM levels, we quantified the production of ethylene in wild-type and ref8 plants (Table 2). These measurements indicated that ref8 rosettes are competent to synthesize ethylene, and that a block in SAM biosynthesis is not likely to be the cause of the perturbation in phenylpropanoid metabolism in the mutant.

To directly evaluate the ability of the mutant to hydroxylate p-coumaric acid and/or p-coumaroyl-CoA we performed a modified version of the previous radiotracer feeding experiments, again administering $^{14}$C-L-phenylalanine to excised wild-type and ref8 leaves. In this experiment, the leaf extracts were treated with methanolic HCl to convert hydroxycinnamic acid esters and thioesters as well as free hydroxycinnamic acids to their corresponding methyl esters, while simultaneously preventing the destruction of alkali-labile dihydroxy-substituted compounds such as caffeic acid. Following two successive rounds of preparative TLC, we analyzed the semi-purified methylcaffeate by HPLC and liquid scintillation counting. Radiotracer feeding experiment designed to measure incorporation of label from $^{14}$C-L-phenylalanine specifically into caffeic acid, analyzed as its methylester. The continuous line represents the UV-absorption of the HPLC column eluate. The histogram represents radioactivity associated with each fraction (Ca, caffeic acid; pC, p-coumaric acid; Me-Ca, methylcaffeic acid; Me-pC, methyl-p-coumaric acid). Using UV detection, we readily identified the methylcaffeate derived from the internal standard of unlabeled caffeic acid that had been added to the wild-type and ref8 samples at the time of extraction. In contrast, whereas radioactivity co-chromatographing with methylcaffeate was readily detected in the fractions collected from the wild-type samples, no radioactivity was detected in these fractions when this procedure was repeated on the ref8 samples. These experiments, as well as the phenotypic characterization of the ref8 mutant (Franke et al., submitted), provided extremely strong evidence that the REF8 gene encodes a protein required for the activity or expression of C3H.

TABLE 2

Ethylene production in wild-type and ref8 Arabidopsis. Rosettes of three-week-old plants were closed in a glass vial and ethylene content in the headspace gas was determined after three hours by gas chromatography. The data represent the means of three independent measurements ± standard deviation.

|  | ethylene production (ppb mg f.w.$^{-1}$ min$^{-1}$ ± std. dev.) |
| --- | --- |
| wild type | 11.3 ± 2.7 |
| ref8 | 6.3 ± 1.3 |

Example 2

Evaluation of Cell-Wall Bound Polysaccharides from ref8 Mutant

Figure 4A:
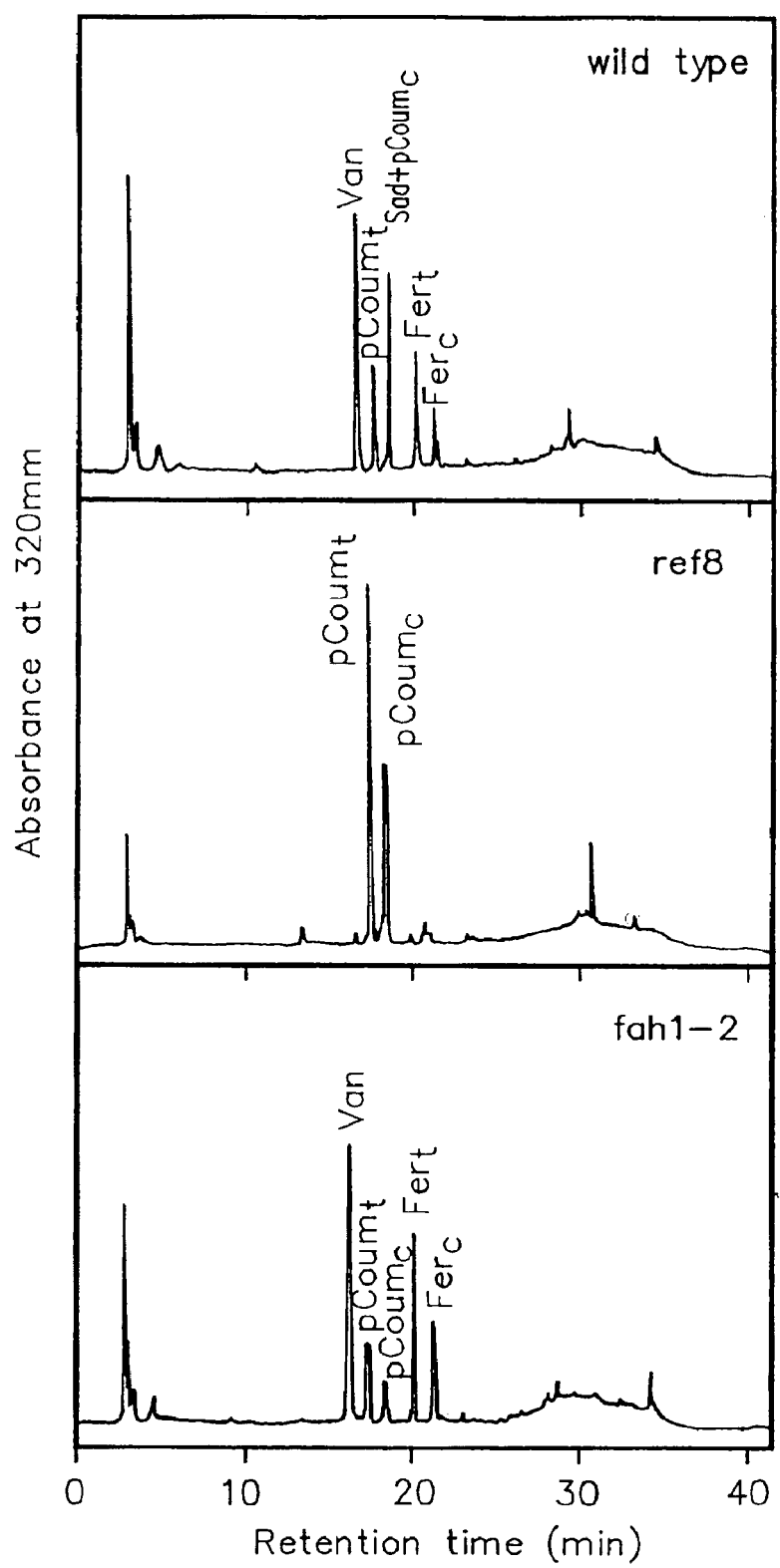
FIGS. 4A–B show HPLC separation of monomeric phenolic products liberated upon alkaline hydrolysis from cell walls of *Arabidopsis* wild-type, ref8 and fah1 plants. Cell walls were prepared from rachis tissue of 6 week old plants by successive extraction with neutral phosphate buffer, ethanol and acetone and subjected to alkaline hydrolysis (1M NaOH, 16 h, room temperature). Released phenolics were extracted in ethyl acetate and separated by reverse phase HPLC using detection at 320 (A) or 275 (B)nm. pCoum$_c$, cis-p-coumaric acid; pCoum$_t$, trans-p-coumaric acid; fer$_c$, cis-ferulic acid; Fer$_t$, trans-ferulic acid; Van, vanillin; Sad, syringealdehyde; pOHB, p-hydroxybenzaldehyde.
Figure 4B:
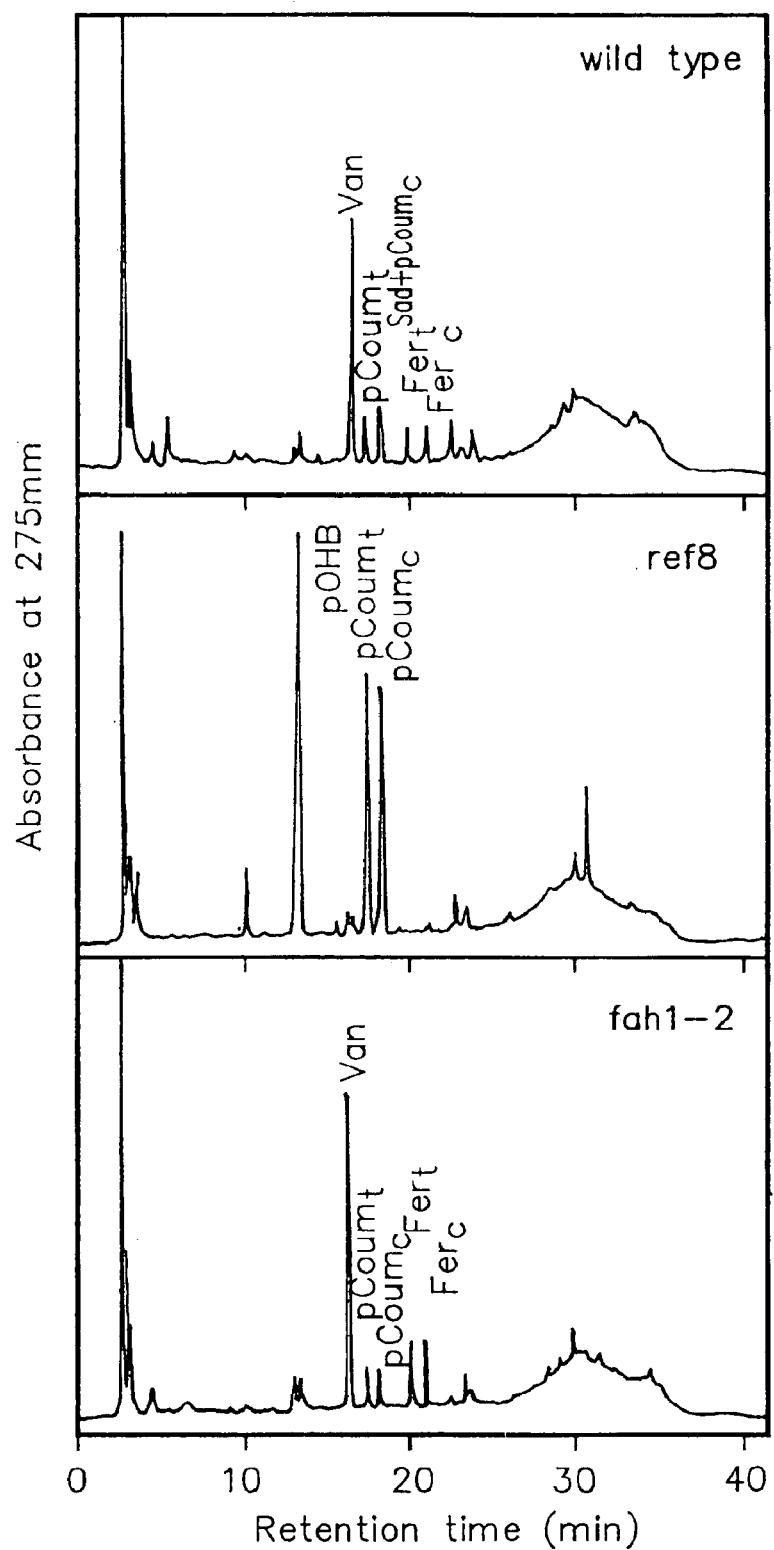

Plant cell walls frequently contain hydroxycinnamic acids that are esterified to cell wall polysaccharides. To evaluate whether the ref8 mutation has an impact on cell wall-bound phenylpropanoids, wild-type and ref8 rachis cell wall preparations were subjected to alkaline hydrolysis to release esterified phenolics. HPLC analysis of cell wall hydrolysates with UV detection at 320 nm revealed that wild-type plants deposit ester-bound forms of p-coumaric and ferulic acid in their cell walls (FIG. 4). These extracts also contained substantial amounts of substances that co-chromatograph with vanillin and syringaldehyde, presumably arising from guaiacyl and syringyl lignin subunits, respectively. Although the cis-isomer of p-coumaric acid co-chromatographs with syringaldehyde in this system, similar experiments conducted on fahl cell walls which lack syringyl lignin and thus do not generate syringaldehyde revealed that only small amounts of p-coumarate are actually ester-linked to *Arabidopsis* cell walls. In contrast, analysis of ref8 extracts at 320 nm indicated that the cis-and trans-isomers of p-coumaric acid dominated the chromatographic profile, and that only small quantities of compounds co-chromatographing with ferulic acid isomers were present. Since the ability to absorb long wave UV light is restricted to compounds in which the double bond system of the phenolic ring extends into the propene side chain, the same samples were re-analyzed using a wavelength of 275 nm to test for the presence of other classes of phenolic compounds (FIG. 4). This detection method revealed the presence of a compound that co-chromatographs with p-hydroxybenzaldehyde in the cell wall hydrolysates of the ref8 mutant. This finding suggests that ref8 cell walls may contain novel esters of p-hydroxybenzaldehyde. Alternatively, it may indicate that the lignin in the ref8 mutant contains subunits derived from p-hydroxycinnamyl alcohol in addition to, or instead of, subunits derived from coniferyl and/or sinapyl alcohols (see below). This novel lignin might release p-hydroxybenzaldehyde under the conditions used in this experiment.

From the ref8 mutant phenotypes described above, it can be expected that down-regulation of C3H polypeptide activity in other plants would lead to similar changes in cell wall biochemical characteristics. Considering that the presence of cell wall esterified phenolics have a dramatic impact on cell wall characteristics such as the digestibility of plant-derived products used as animal feed, it can be anticipated that such changes in C3H polypeptide activity will add value to plants used in agriculture and forestry. It is well known in the art that down-regulation of C3H polypeptide activity could be achieved by many different mechanisms, including, but not limited to stable transformation with antisense suppression constructs, stable transformation with sense suppression constructs, or virus induced gene silencing.

Example 3

The ref8 Mutation Affects Lignin Biosynthesis Qualitatively

We have previously found that some *Arabidopsis* mutants defective in sinapate ester metabolism also exhibit alterations in lignin biosynthesis. To examine the impact of the ref8 mutation on lignin content, we analyzed cell wall material using thioglycolic acid (TGA) derivatization (Campbell and Ellis, 1992), and the Klason method (Kaar et al., 1991) (Table 3). These analyses indicated that the lignin content of ref8 stems was reduced to 20 to 40% of wild-type levels, depending upon the method employed.

From the decrease in lignin content seen in the ref8 mutant, it can be expected that down-regulation of C3H polypeptide activity in other plants would lead to similar decreases in lignin deposition. Considering that lignin content has is an important determinant in the use of lignocellulosic plant materials for purposes such as pulp and paper production, and influences the nutritional quality of forages fed to animals, it can be anticipated that such changes in C3H polypeptide activity will add value to plants used in agriculture and forestry. It is well known in the art that down-regulation of C3H polypeptide activity could be achieved by many different mechanisms, including, but not limited to stable transformation with antisense suppression constructs, stable transformation with sense suppression constructs, or virus induced gene silencing.

Example 4

The ret8 Mutation Affects Lignin Biosynthesis Qualitatively

To examine the type of lignin deposited in the ref8 mutant, rachis cell wall preparations were analyzed by nitrobenzene oxidation (NBO), the DFRC (derivatization followed by reductive cleavage) method (Lu and Ralph, 1997), and by pyrolysis GC-mass spectrometry (Py-GC-MS) (Bocchini et al., 1997) (FIG. 5). NBO releases substituted benzaldehyde and benzoic acid derivatives from lignin and the relative content of these monomers is indicative of the presence of p-hydroxyphenyl (p-hydroxybenzaldehyde and p-hydroxybenzoic acid) guaiacyl (vanillin and vanillic acid) and syringyl (syringaldehyde and syringic acid) units in the polymer. The expected products representing a typical angiosperm guaiacyl-syringyl co-polymer were identified following HPLC analysis of the NBO products from wild-type cell walls (FIG. 5). In contrast, NBO of ref8 cell walls yielded only trace amounts of a compound that co-chromatographed with vanillin, and a substance with the retention time of p-hydroxybenzaldehyde was instead the major NBO product. Lignin analysis by the DFRC method generates acetylated hydroxycinnamyl alcohols from beta-O-4 etherified lignin subunits. When DFRC products from wild-type cell wall preparations were analyzed by GC-MS using selective ion monitoring, coniferyl and sinapyl alcohol diacetates were identified by their retention times and EIMS fragmentation patterns as the major lignin degradation products. Trace amounts of p-coumaryl alcohol diacetate were also observed, although the low abundance of the compound precluded its quantitation. In contrast, p-coumaryl alcohol diacetate was the major DFRC product in ref8 samples. Both coniferyl and sinapyl alcohol diacetates were observed, but were below quantifiable limits. Consistent with the TGA and Klason data (Table 2), comparison of DFRC yields on a per g dry weight basis indicated that ref8 cell walls contain less total lignin. It should be noted, however, that these values are not directly comparable since DFRC yields from ref8 lignin were substantially lower than wild type when compared based upon Klason lignin content (Table 3).

Analysis of the wild-type and mutant lignin by Py-GC-MS confirmed the results of the previous two methods. An array of pyrolysis degradation products expected for a mixed guaiacyl/syringyl copolymer were identified in wild-type samples which also contained small amounts of p-hydroxyphenyl lignin-derived products. In contrast, pyrolysis yielded only p-hydroxy products from ref8 samples and guaiacyl and syringyl substituted products were below detectable limits. These data indicate that, in addition to interfering with the biosynthesis of hydroxycinnamic acids, the ref8 mutation affects the production of the monolignols from which wild-type lignin is polymerized.

The changes in lignin monomer composition in the ref8 mutant makes it clear that it can be expected that down-regulation of REF8 activity in other plants would lead to similar changes in lignin biochemistry. Since lignin monomer composition influences pulping efficiency as well as other agronomic characteristics of plants, it can again be anticipated that similar changes in C3H polypeptide activity will add value to plants used in agriculture and forestry. It is well known in the art that down-regulation of C3H polypeptide activity could be achieved by many different mechanisms, including, but not limited to stable transformation with antisense suppression constructs, stable transformation with sense suppression constructs, or virus induced gene silencing.

Example 5

Evaluation of the Physical and Chemical Resistance of ref8 Cell Walls

The experiments described above in the previous examples demonstrated that ref8 plants deposit less lignin than the wild type, and that the lignin of ref8 plants is synthesized from monomers that are normally at best only very minor components of the wild-type polymer. To determine whether these changes in lignin quality and quantity had a broader impact on cell wall characteristics, we measured the resistance of wild-type and ref8 cell wall preparations to the activity of polysaccharide hydrolases. Over half of the original cell wall mass remained after digestion of wild-type cell walls, reflecting the resistance to enzymatic degradation of crystalline cellulose and lignin. Treatment of wall preparations from the syringyl lignin-deficient fah1 mutant gave similar results, indicating that perturbations in cell wall chemistry do not necessarily result in altered cell wall degradability. In contrast, the ref8 cell walls exhibited increased susceptibility to enzymatic digestion; the residue remaining after digestion was only one fifth of that found with wild-type cell walls.

The changes in cell wall degradability in the ref8 mutant clearly demonstrate the potential value of down-regulation of C3H polypeptide activity in plants important to agriculture and forestry. It is clear that similar changes in cell wall characteristics would lead to improved utilization of lignocellulosic material in terms of pulp and paper production, and in agricultural process including, but not limited to, the use of forages for animal feedstocks, and the production of other downstream products such as ethanol produced through fermentation processes.

TABLE 3

Impact of the ref8 mutation on radius lignin content as measured by the TGA method. The data represent the means of three independent measurements ± standard deviation.

| | TGA lignin content ($A_{280}$ mg cell wall$^{-1}$ ± std. dev.) |
|---|---|
| wild type | 3.12 ± 0.21 |
| ref8 | 0.57 ± 0.23 |

Example 6

Isolation of REF8 Gene

Figure 3:
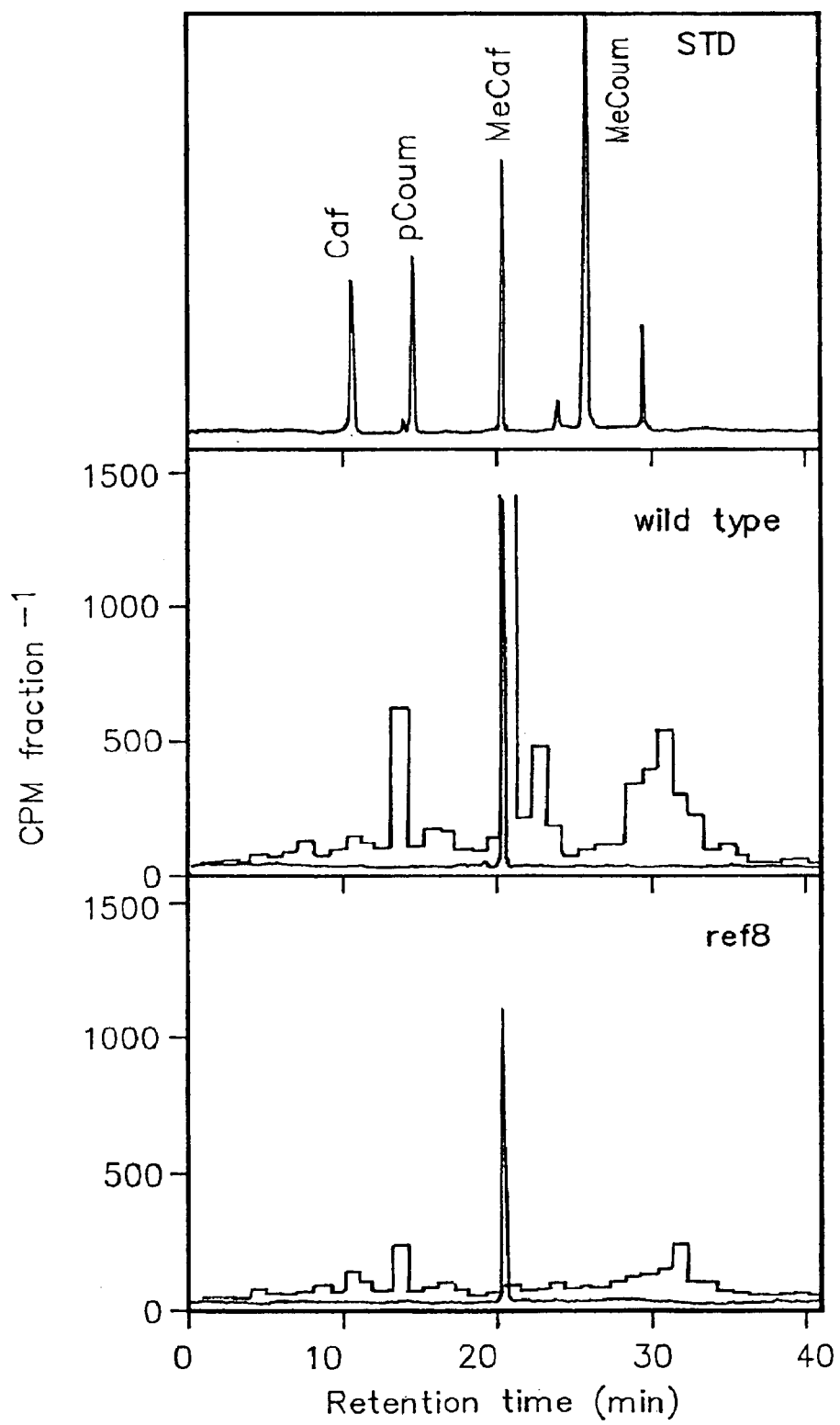
FIG. 3 shows analysis of phenylpropanoid synthesis in a standard, wild-type, and ref8 leaves using radiotracer feeding technology. Radiotracer feeding and metabolite extraction was performed as in FIG. 2 except that extracts were dried and methanolyzed by incubation in methanolic HCL (80° C., 1h). Products were extracted into diethyl ether and methylcaffeate was purified by semi-preparative silica gel TLC (solvent 1, benzene/dioxane/acetic acid 90:10:1; solvent 2, toluene/acetic acid/water 2:1 sat.), followed by reverse phase HPLC. The continuous line represents the UV-absorption of the HPLC column eluate. The histogram represents radioactivity associated with each fraction. Caf, caffeic acid; pCoum, p-coumaric acid; MeCaf, methylcaffeate; MeCoum, methyl p-coumarate.

To isolate the REF8 gene using positional cloning, we took advantage of the advanced state of the *Arabidopsis* genome sequencing effort. Using a mapping population of 535 $F_2$ plants derived from a ref8/ref8 (Columbia background)×REF8/REF8 (Landsberg erecta) cross, the position of the REF8 gene was initially determined to be between markers nga168 and T8M12. Thirty nine plants were found to carry chromosomes that were recombinant within this region, and these individuals were studied further to determine a smaller mapping interval for the REF8 gene. These studies showed REF8 to lie between markers T7D17 and SGCSNP169, a region defined by a contig of approximately 10 BACs. The annotations of these clones were inspected for genes encoding putative oxidases and hydroxylases at http://www.mips.biochem.mpg.de/proj/thal. Two P450s and one peroxidase were identified within this region that we considered to be candidates for REF8 (FIG. 3). Based upon the relative position of these genes within the mapping interval, and the recombination distances determined for the flanking upper and lower markers (2 recombination events between marker T7D 17 and REF8; 10 recombination events between REF8 and marker SGCSNP 169), we identified a gene on BAC T20B5 encoding a putative P450 belonging to the CYP98 class (CYP98A3) as the most likely candidate for REF8. To provide a preliminary indication whether CYP98A3 was likely to correspond to REF8, we evaluated the tissue specificity of its expression using RNA gel blot hybridization.

Example 7

Characterization of C3H Polypeptide

Figure 7:
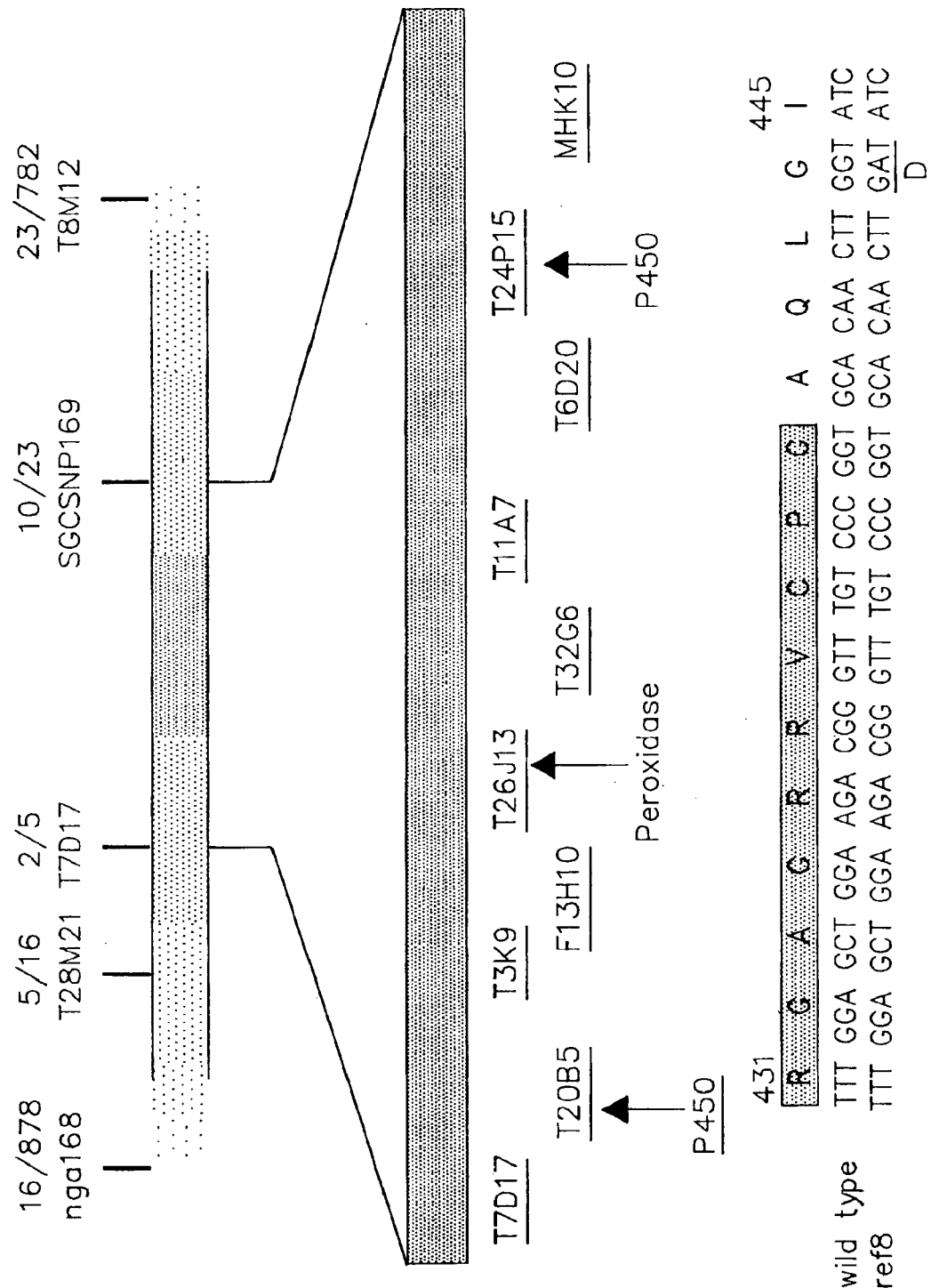
FIG. 7 shows map-based cloning of the REF8 gene. A narrow mapping interval was determined for the REF8 gene containing three genes considered to be candidates for REF8. The P450 (underlined) encoded on BAC T20B5 (T20B5.9) was selected as the most likely candidate for REF8 based upon its position within the mapping interval relative to the frequency of recombinant chromosomes identified within the mapping population at the flanking markers. Near the heme binding motif of T20B5.9, the ref8 genes contains a single G to A transition mutation that results in a G444A substitution in the amino acid sequence.

The experiments described above strongly suggested that the *Arabidopsis* REF8 gene corresponds to T20B5.9, a gene also annotated as CYP98A3, a putative P450. To provide further supporting evidence for this hypothesis, we sequenced the putative ref8 cDNA. The mutant sequence contained a single G to A nucleotide substitution that leads to a non-conservative amino acid substitution near the conserved heme-binding region of the protein (FIG. 7). To evaluate whether the G to A nucleotide substitution found in the mutant gene impairs enzymatic function, we expressed the wild-type and mutant genes in *E. coli* and yeast. For expression of the protein in *E. coli*, we used the pBOV vector, a version of pCWOri+ modified for the high-level expression of eukaryotic P450s (Barnes et al., 1991). In this vector, the coding sequence of a portion of the N-terminal domain of the eukaryotic P450 is replaced by the first eight codons of the bovine P450 CYP17. For the yeast experiments, we expressed the native CYP98A3 protein using the vector YeDP60 (Urban et al., 1990). The CYP98A3 expression constructs were then transformed into WAT11 yeast in which the endogenous yeast P450 reductase gene has been replaced with the ATR1 *Arabidopsis* P450 reductase gene under the control of the yeast GAL10-CYC1 promoter to provide the expressed P450 with high levels of its normal reductase partner (Pompon et al., 1996).

Figure 8A:
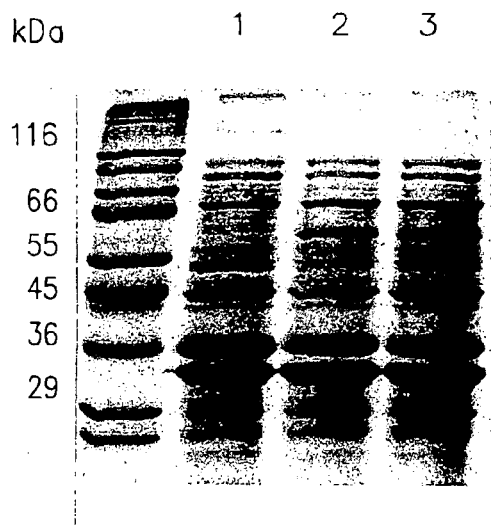
FIGS. 8A–D show heterologous expression of REF8. (A) SDS-PAGE analysis of microsomal proteins from *E. coli* harboring pBOV (lane 1), pBOV-REF2 (lane 2), and pBOV-ref8 (lane 3). (B) Carbon monoxide difference spectra of dithionite-reduced *E. coli* membranes. Dashed line, baseline prior to CO treatment; solid line, CO difference spectrum of REF8-containing membranes; dotted line, CO difference spectrum of membranes from *E. coli* expressing the protein encoded by the ref8 allele. (C) SDS-PAGE analysis of membrane protein-enriched Triton X-114 detergent phase of yeast microsomal proteins harboring pYeDP60 (lane 1), pYeDP60-REF8 (lane 2), and pYeDP60-ref8 (lane 3). (D) Carbon monoxide difference spectrun of dithionite-reduced Triton X-114 detergent phase from microsomes prepared from yeast harboring pYeDP60-REF8. Dashed line, baseline prior to CO treatment; solid line, difference spectrum after CO treatment.
Figure 8B:
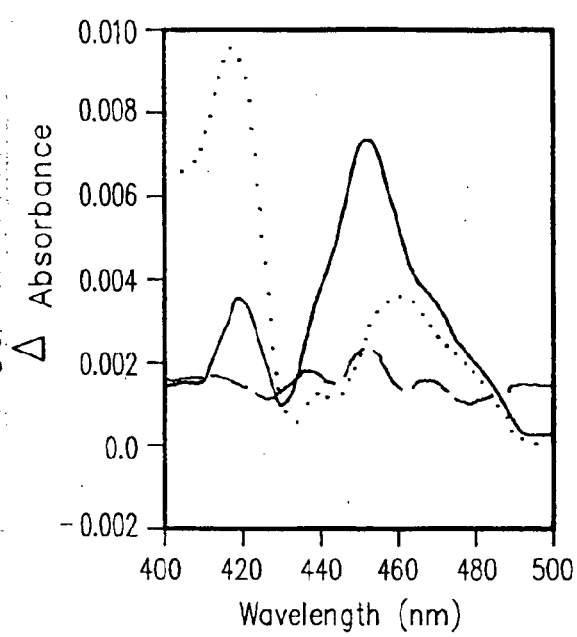

First, membrane preparations were isolated for spectroscopic and SDS-PAGE analysis from *E. coli* carrying either the pBOV control vector, the REF8 expression vector pBOV-REF8, or the pBOV-ref8 construct carrying the mutant gene sequence. SDS-PAGE analysis indicated that membranes from bacteria carrying pBOV-REF8 and pBOV-ref8 contained an abundant protein with a molecular mass of approximately 58 kDa, consistent with the expected mass of 57,926 Da for the inferred translation product of the putative C3H cDNA (FIG. 8a). This protein was absent in samples prepared from bacteria carrying the control pBOV vector. As expected, carbon monoxide difference spectroscopy indicated that samples prepared from control bacteria contained no spectrally active P450. Spectroscopic examination of membranes prepared from bacteria expressing the putative C3H protein revealed a 450 nm absorbance peak characteristic of P450s (FIG. 8b). In contrast, the CO difference spectrum of membranes from bacteria transformed with the pBOV-ref8 construct gave a spectrum dominated by a peak at 420 nm, indicating that the protein is capable of binding the heme prosthetic group found in P450s, but is mis-folded or structurally altered in such a way that it is likely to be inactive.

Figure 8C:
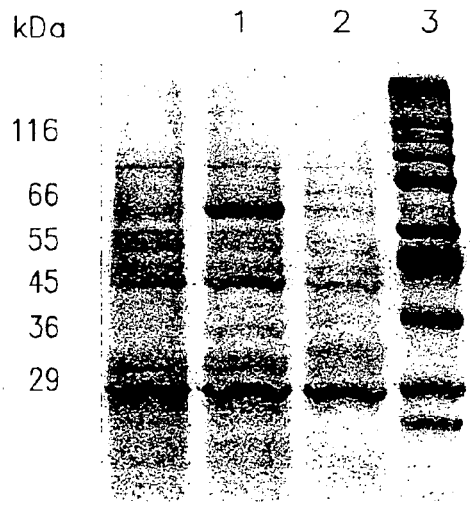
Figure 8D:
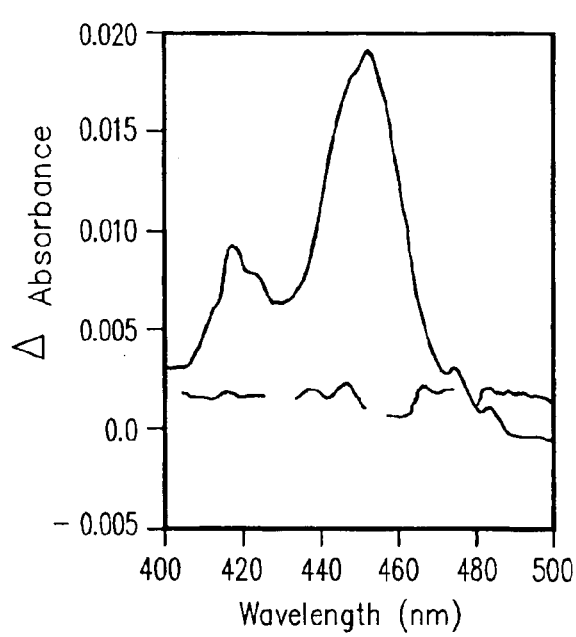

Next, microsomal preparations prepared from yeast transformed with YeDP60, YeDP60-REF8 or YeDP60-ref8 were similarly analyzed by SDS-PAGE and CO difference spectroscopy. Prior to these analysis, membrane preparations were first fractionated using a Triton X-114 phase partition procedure to enrich the sample in integral membrane proteins (Werck-Reichhart et al., 1991). When analyzed by SDS-PAGE (FIG. 8c), the Triton phase prepared from membranes of control yeast contained a number of bands, whereas similar preparations from yeast expressing the putative wild-type C3H protein contained an additional protein with a molecular mass of approximately 58 kDa. In contrast, mutant protein does not accumulate in yeast carrying the YeDP60-ref8 vector (FIG. 8c). As expected, carbon monoxide difference spectroscopy indicated that samples prepared from control cells contained essentially no spectrally active P450; whereas, under the same conditions membranes prepared from yeast expressing the wild type version of the putative C3H protein exhibited a strong 450 nm absorbance peak (FIG. 8d). Taken together, these data suggest that the putative C3H protein is probably targeted to the endoplasmic reticulum in yeast cells, where it should be catalytically active. In contrast, the mutant protein does not accumulate, possibly due to enhanced degradation arising from mis-folding like that previously seen when the mutant protein was expressed in *E. coli*.

Figure 6B:
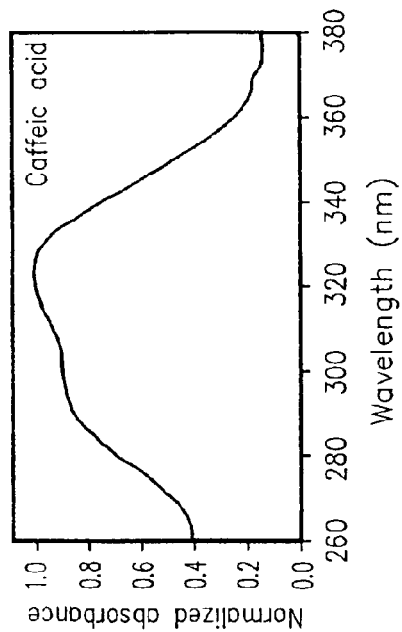
FIGS. 6A–C show expression of active C3H in yeast. Yeast carrying the void YeDP60 vector or the YeDP60-C3H vector were cultured and induced as described previously (Humphreys, et al., 1999) in media supplemented with p-coumaric acid. At the end of the incubation period the medium was extracted with ethylacetate, and analyzed by HPLC (FIG. 6A). Spectra of the caffeic acid standard, and the co-chromatographing novel peak found in the medium of the yeast carrying YeDP60-C3H are shown in FIGS. 6B and C.
Figure 6C:
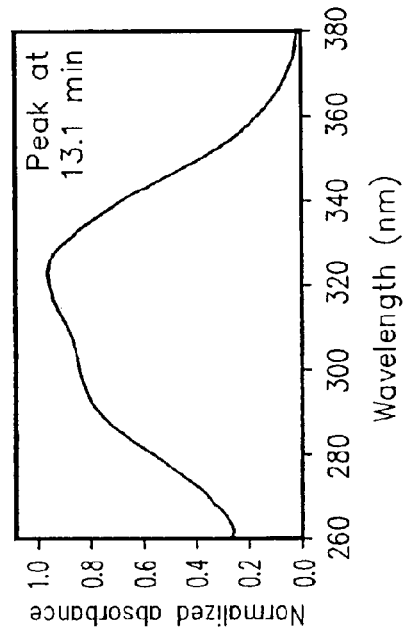
Figure 6A:
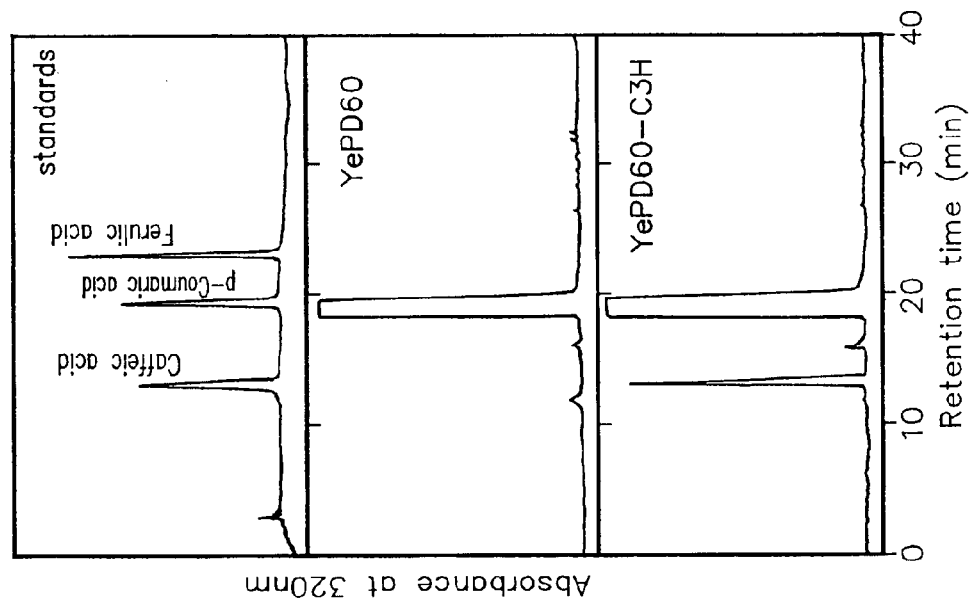
Figure 9E:
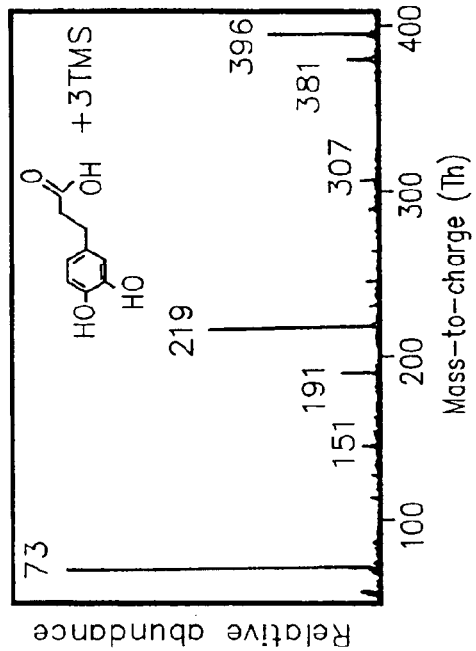
FIGS. 9A–C are duplicative of FIGS. 6A–C and FIGS. 9D–F show results of replicate experiments described in FIG. 6A–C when analyzed by GC-MS.
Figure 9F:
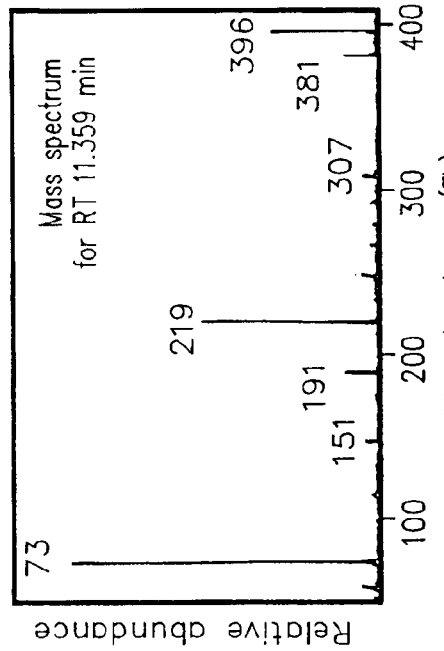
Figure 9D:
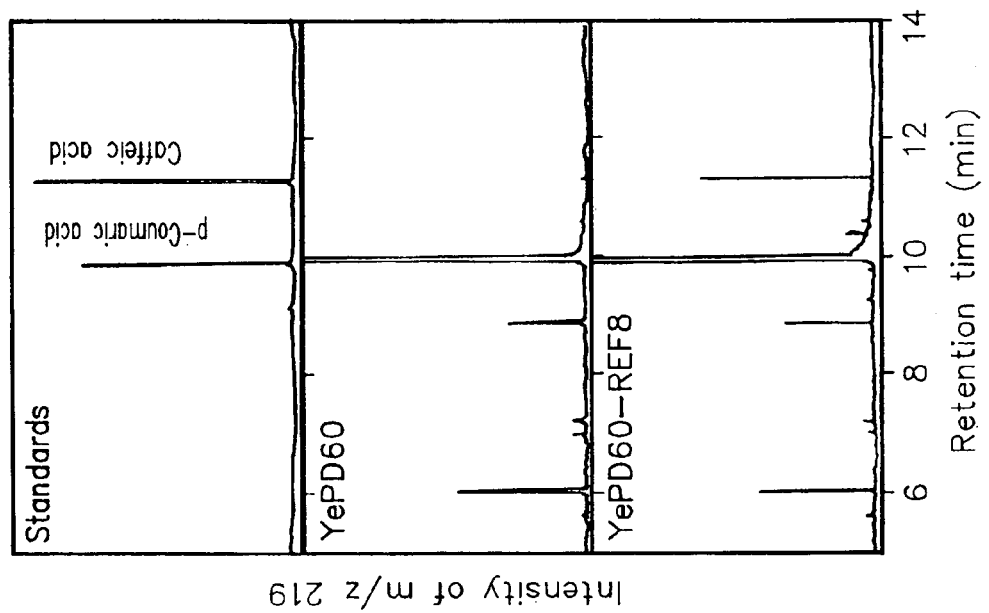

Finally, WAT11 yeast carrying the control vector and the YeDP60-REF8 vector were assayed for C3H polypeptide activity in vivo by adding p-coumarate directly to the medium of galactose-induced yeast cultures. This method has previously been used to demonstrate the activity of C4H and F5H heterologously expressed in yeast (Pierrel et al., 1994; Humphreys et al., 1999), and exploits the ability of simple hydroxycinnamic acids to readily cross yeast membranes. When p-coumarate was added to the medium of control yeast, it was the predominant UV-absorbent substance present in the medium after several hours of incubation. In contrast, when a parallel experiment was performed with yeast harboring the YeDP60-REF8 expression vector, a novel peak was found whose retention time and UV-spectrum matched precisely those of caffeic acid (FIG. 6). Replicate experiments analyzed by GC-MS with selective ion monitoring permitted unequivocal identification of the C3H reaction product. (FIG. 9) In the context of the phenotypic characterization of the ref8 mutant (Franke et al., submitted), these data provide definitive proof that CYP98A3 encodes C3H polypeptide, and that C3H polypeptide is a P450.

Example 8

Other Substrates of C3H Polypeptide

Although the in vivo assays of yeast carrying the YeDP60-REF8 vector demonstrated that C3H polypeptide is capable of hydroxylating p-coumarate, it was not possible to use this approach to determine kinetic constants for the enzyme, nor to use this system to assay the activity of C3H toward substrates that cannot readily cross the yeast plasma membrane. To experimentally address these issues, C3H-containing microsomes were prepared for use in in vitro assays of enzymatic activity. Consistent with the in vivo results, incubation of C3H in the presence of p-coumarate in vitro resulted in the production of caffeic acid, although this activity was so low that it precluded detailed kinetic analysis. In addition to p-coumarate,severa other compounds have been suggested to be substrates for the 3-hydroxylase(s) of phenylpropanoid metabolism (Heller and Kühnl, 1985; K ühnl et al., 1987; Kneusel et al., 1989; Tanaka and Kojima, 1991). Because the assays using p-coumarate suggested that it may not be the optimal substrate for C3H, we assayed the activity of the enzyme against an array of other possible substrates. In these experiments, no activity of C3H polypeptide toward p-coumaroyl CoA, p-hydroxycinnamyl alcohol, and 1-O-p-coumaroyl—D-glucose was detected. Levels of activity comparable to those seen with p-coumarate were seen when p-coumaraldehyde was used as a substrate. In contrast, much higher levels of activity were seen when p-coumaroyl methyl ester was used as a substrate (FIG. 7a), although the apparent $K_m$ for this substrate (2.5±0.1 mM) was still higher than those of other phenylpropanoid pathway P450s. No activity was seen when cinnamate, caffeate or ferulate was used as a substrate for C3H.

Example 9

Increase in Flavonoid Content and Resistance to UV Light

A plant in which C3H polypeptide activity is decreased will, as a result, have increased flavonoid content. Since C3H polypeptide functions in a biochemical pathway that diverts phenylpropanoid pathway intermediates away from flavonoid biosynthesis, it would be apparent to one skilled in the art that a plant in which C3H polypeptide activity was down-regulated using methods including, but not limited to stable transformation with antisense suppression constructs, stable transformation with sense suppression constructs, or virus induced gene silencing, would have increased levels of flavonoids. Such a plant would be of value because it is well known in the art that flavonoids are important in the resistance of plant to UV light (Li, et al., 1993). Thus, it can be expected that plant in which C3H polypeptide activity is downregulated would have, among other desirable characteristics, enhanced resistance to UV light.

Example 10

Increase in Isoflavonoid Content and Nutritional Value

A plant in which C3H polypeptide activity is decreased will, as a result, have increased isoflavonoid content. Since REF8 functions in a biochemical pathway that diverts phenylpropanoid pathway intermediates away from isoflavonoid biosynthesis, it would be apparent to one skilled in the art that a plant in which REF8 activity was down-regulated using methods including, but not limited to stable transformation with antisense suppression constructs, stable transformation with sense suppression constructs, or virus induced gene silencing, would have increased levels of isoflavonoids. Such a plant would be of value because it well known in the art that isoflavonoids are important nutrients in the human diet and have value as phytoestrogens (Humphreys, et al., 2000). Thus, it can be expected that plant in which REF8 activity is downregulated would have desirable characteristics including but not limited to enhanced levels of isoflavonoids and improved nutritional value.

Example 11

Increase in Anthocyanin Content

Since C3H polypeptide functions in a biochemical pathway that diverts phenylpropanoid pathway intermediates away from anthocyanin biosynthesis, it would be apparent to one skilled in the art that a plant in which C3H polypeptide activity was down-regulated using methods including, but not limited to stable transformation with antisense suppression constructs, stable transformation with sense suppression constructs, or virus induced gene silencing, would have increased levels of anthocyanins. Such a plant would be of value because it well known in the art that anthocyanins are important flower pigments, and that metabolic engineering of flower color is of significant value in the cut flower industry, and in the production of horticulturally desirable plants in general. (Holton, et al., 1993). Thus, it can be expected that plant in which REF8 activity is downregulated would have desirable characteristics including but not limited to enhanced levels of anthocyanins.

Example 12

Decrease in Cell Well Bound Conjugates

A plant in which C3H polypeptide activity is decreased will, as a result, have increased anthocyanin content. Since C3H polypeptide functions in a biochemical pathway that is required for the synthesis of phenolic compounds commonly found chemically linked to plant cell walls, it would be apparent to one skilled in the art that a plant in which C3H polypeptide activity was down-regulated using methods including, but not limited to stable transformation with antisense suppression constructs, stable transformation with sense suppression constructs, or virus induced gene silencing, would have decreased levels of cell wall-bound conjugates including but not limited to ferulic and sinapic acids. Such a plant would be of value because, among other things, it well known in the art that cell wall bound phenolics decrease the nutritional value of plants used as animal feedstocks (Jung, H. G. and Deetz, D. A. (1993) Cell wall lignification and degradability in Forage Cell Wall Structure and Digestibility (H G Jung, D R Buxton, R D Hatfield, J Ralph eds.), ASA/CSSA/SSSA Press, Madison, Wis.). Thus, it can be expected that plant in which REF8 activity is downregulated would have desirable characteristics including but not limited to enhanced digestibility.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

BIBLIOGRAPHY

Abe, et al., 1987. *J. Biol. Chem.* 262:16793.
Adang, et al., 1993. *Plant Molec. Biol.* 21:1131.
Alibert, et al., 1972. *Physiol. Plant* 27: 240–243.
Altschul, et al., 1993. *J. Mol. Biol.* 215:403–410.
Altschul, et al., 1997. *Nucl. Acids Res.* 25:3389–3402.
Ammerer, 1983. *Methods in Enzymol.* 101:192–201.
Anand, 1992. Techniques for the Analysis of Complex Genomes, Academic Press.
Apse, et al., 1999. *Science* 285:1256–1258.
Artus, et al., 1996. *Proc. Natl. Acad. Sci USA* 93:13404–13409.
Atanassova, et al., 1995. *Plant J.* 8: 465–477.
Ausubel, et al., 1992. Current Protocols in Molecular Biology, John Wiley & Sons, New York, N.Y.
Ausubel, et al., 1990. Current Protocols in Molecular Biology, Wiley Interscience, pp. 8.2.8–8.2.13.
Ausubel, et al., 1987. Current Protocols in Molecular Biology, published by Greene Publishing Assoc. and Wiley-Interscience.
Baker, et al., 1990. *Bio/Techniques* 9:268–272.
Bambot, et al., 1993. *PCR Methods and Applications* 2:266.
Bartlett, et al., 1972. *FEBS Lett.* 23: 265–267.
Baucher, et al., 1996. *Plant Physiol.* 112: 1479–1490.
Baulcombe, 1999. *Current Opinion in Plant Biology* 2:109–113.
Beachy, et al., 1990. *Ann. Rev. Phytopathol.* 28:451.
Beaucage and Caruthers, 1981. *Tetra. Letts.* 22:1859–1862.
Becker and Guarente, 1991. *Methods in Enzymol.* 194:182–186.
Beetham, 1999. *Proc. Natl. Acad. Sci. USA* 96:8774–8778.
Bell-Lelong, et al., 1997. *Plant Physiol.* 113: 729–738
Benbrook, et al., 1986. *In Proceedings Bio Expo 1986*, Butterworth, Stoneham, Mass., pp. 27–54.
Binding, 1985. *Regeneration of Plants, Plant Protoplasts*, CRC Press, Boca Raton, Fla, pp. 21–73.
Bingham, et al., 1998. *Br. J. Nutr.* 79: 393–406.
Binns, et al., 1987. *Proc. Natl. Acad. Sci. USA* 84: 980–984.
Bishop (Ed.), 1994. *Guide to Huge Computers*, Academic Press, San Diego, Calif.
Bollwell and Butt, 1983. *Phytochemistry* 22: 37–45.
Boniwell and Butt, 1986. *Z Naturforsch* 41c: 56–60.

Botella, et al., 1994. *Plant Molec. Biol.* 24:757.
Brock, 1989. "Biotechnology: A Textbook of Industrial Microbiology," 2d Ed., Sinauer Associates, Inc,. Sunderland, Mass.
Brugliera, et al., 1999. *Plant J.* 19: 441–451.
Brunner, 1998. Structure and expression of two *Populus trichocarpa* homologs of the floral homeotic gene AGAMOUS, Ph.D. Dissertation, Department of Forest Science, Oregon State University, Corvallis.
Buchman and Berg, 1988. *Mol. Cell. Biol.* 8:4395–4405.
Busch, et al., 1999. *Science* 285:585–588.
Campbell and Ellis, 1992. *Planta* 186: 409–417.
Carillo and Lipman, 1988. *SLAM J. Applied Math.* 48:1073.
Chapple, et al., 1992. *Plant Cell* 4:1413–1424.
Chapple, 1998. *Annu. Rev. Plant Biochem. Plant Mol. Biol.* 49: 311–343.
Chaubet, et al., 1987. *Devel. Genet.* 8:461–473.
Chrispeels, 1991. *Ann. Rev. Plant Phys. Plant Mol. Biol.* 42:21–53.
Coe, et al., 1981. *J. Hered.* 72: 318–320.
Compton, 1991. *Nature* 350:91–92.
Coombs, et al., 1998. *Proteins*, pp. 259–311, 1 plate, R. H. Angeletti, Ed., Academic, San Diego, Calif.
Daboussi, et al., 1989. *Curr. Genet.* 15:453–456.
Davey, 1983. Recent Developments in the Culture and Regeneration of Plant Protoplasts, *Protoplasts Lecture Proceedings*, pp. 12–29 (Birkhauer Basil).
DeGreef, et al., 1989. *Bio/Technology* 7:61.
Dempsey, et al., 1999. *Crit Rev Plant Sci* 18: 547–575.
Deutscher, 1990. *Meth. Enzymology* 182:83–89.
Devereaux, et al., 1984. *Nucleic Acids Res.* 12:387–395.
Duke and Vaughn, 1982. *Physiol. Plant.* 54: 381–385.
Elliot, et al., 1993. *Plant Molec. Biol.* 21:515. *Enhancers and Eukaryotic Gene Expression*, 1983, Cold Spring Harbor Laboratory, Cold Spring Harbor, N.Y.
Enoki, et al., 1999. *K Plant J.* 19:605–613.
Evans, et al., 1983. *Protoplasts Isolation and Culture, Handbook of plant Cell Culture*, Macmillan Publishing Company, NY, pp. 124–176.
Fahy, et al., 1991. *PCR Methods. Appl.* 1:25–33.
Fiers, et al., 1978. *Nature* 273:113–120.
Fisher, et al., 1993. *Plant Physiol.* 102:1045.
Fraley, et al., 1993. *Proc. Natl. Acad. Sci. (USA)* 80:4803.
Franke, et al., 2000. *Plant J.* 22: 223–234
Freeling and Walbot (Eds.), 1994. *The Maize Handbook*, Springer, NY.
Freeman, et al., 1984. *Plant Cell Physiol.* 25:1353.
Frohman et al., 1988. *PNAS USA* 85:8998.
Fromm, et al., 1985. *Proc. Natl. Acad. Sci. (USA)* 82:5824.
Gabriac, et al., 1991. *Arch. Biochem. Biophys.* 288: 302–309.
Geiser, et al., 1986. *Gene* 48:109.
Gelvin, et al., 1990. *Plant Molecular Biology: Manual*, Kluwer Academic Press, Dordrecht, Netherlands.
Gerhardt, et al. (Eds.), 1994. "Manual of Methods for General Bacteriology," American Society for Microbiology, Washington, D.C.
Glover, 1985. *DNA Cloning* I and II, Oxford Press.
Gordon-Kamm, 1990. *The Plant Cell* 2:603–618.
Grand, 1984. *FEBS Lett.* 169: 7–11.
Gribskov and Devereux (Eds.), 1991. *Sequence Analysis Primer*, Stockton Press, New York.
Griess, et al., 1994. *Plant Physiol.* 104:1467.
Griffin, et al. (Eds.), 1994. *Computer Analysis of Sequence Data*, Part I, Humana Press, New Jersey.
Grotewold, et al., 1994. *Cell* 76: 543–553.
Guilley, et al., 1982. *Cell* 30:763–773.
Guthrie and Fink, 1991. *Guide to Yeast Genetics and Molecular Biology*, Academic Press.
Hain, et al., 1993. *Nature* 361: 153–156.
Hallborn, et al., 1991. *Bio./Technol.* 9:1090.
Halliwell, 1975. *Eur. J. Biochem.* 55: 355–360.
Hamilton, et al., 1992. *Plant Molecular Biology* 18:211–218.
Hammock, et al., 1990. *Nature* 344:458.
Hanley, et al., 2000. *KJ Plant J.* 23(4):557–566.
Haseloff, et al., 1988. *Nature* 334:585–591.
Hayes, et al., 1992. *Biochem. J.* 285:173.
Hein, et al., 1990. *Methods Enzymol.* 183:626–645.
Heller and Kühnl, 1985. *Arch. Biochem. Biophys.* 241: 453–460.
Henikoff, 1984. *Gene* 28:351–359.
Hernan, et al., 2000. *BioTechniques* 28: 789–793.
Hess, 1987. *Intern Rev. Cytol.* 107:367.
Higuchi, 1981. Biosynthesis of lignin in Plant Carbohydrates II. Extracellular Carbohydrates (W Tanner and F A Loewus, eds.), Springer-Verlag, Berlin.
Hohn, et al., 1982. *Molecular Biology of Plant Tumors*, Academic Press, New York, pp. 549–560.
Holton, et al., 1993. *Nature* 366: 276–279.
Horsch, et al., 1984. *Science* 233:496–498.
Horsch, et al., 1985. *Science* 227:1229–1231.
Hu, et al., 1999. *Nature Biotech* 17: 808–812.
Humphreys, et al., 1999. *Proc. Natl. Acad. Sci. USA* 96: 10045–10050.
Humphreys and Chapple, 2000. *Trends Plant Sci* 5: 271–272.
Huub, et al., 1993. *Plant Molec. Biol.* 21:985.
Innis, et al., 1990. *PCR Protocols: A Guide to Methods and Applications*, Academic Press, San Diego, Calif.
Jackson, et al., 1992. *Plant J* 2: 425–434.
Jakoby and Pastan (Eds.), 1979. *Cell Culture, Methods in Enzymology* Vol. 58, Academic Press, Inc., Harcourt Brace Jovanovich, New York.
Jang, et al., 1997. *Science* 275: 218–220.
Jaynes, et al., 1993. *Plant Sci.* 89:43.
Jefferson, et al., 1987. *EMBO J.* 6:3901–3907.
Jones, et al., 1994. *Science* 266:789.
Kamsteeg, et al., 1981. *Z Pflanzenphysiol* 102: 435–442.
Kamsteeg, et al., 1980. *Phytochemistry* 19: 1459–1462.
Kanehisa, 1984. *Nucl. Acids. Res.* 12:203–213.
Kasuga, et al., 1999. *Nature Biotech.* 17:287–291.
Kawalleck, et al., 1993. *Plant Molec. Biol.* 21:673.
Kaye, et al., 1998. *Plant Physiol.* 116:1367–1377.
Kempin, et al., 1997. *Nature* 389:802–803.
Kindle, 1990. *Proc. Natl. Acad. Sci. (USA)* 87:1228.
Klee, et al., 1987. *Ann. Review of Plant Physiology* 38:467–486.
Klein, et al., 1987. *Nature* 327:70–73.
Kneusel, et al., 1989. *Arch. Biochem. Biophys.* 269: 455–462.
Knultzon, et al., 1992. *Proc. Nat. Acad. Sci. USA* 89:2624.
Köetter, et al., 1990. *Curr. Genet.* 18:493–500.
Kojima and Takeuchi, 1989. *J. Biochem.* 105: 265–270.
Kramer, et al., 1993. *Insect. Molec. Biol.* 23:691.
Kubo, et al., 1988. *FEBS Lett.* 241:119.
Kühnl, et al., 1989. *Plant Science* 60: 21–25.
Kühnl, et al., 1987. *Arch. Biochem. Biophys.* 258: 226–232.
Kyte and Doolittle, 1982. *J. Mol. Biol.* 157:105–132.
Lamb, et al., 1992. *Bio/Technology* 10:1436.
Landry, et al., 1995. *Plant Physiol.* 109:1159–1166.
Larsen, et al., 1998. *Plant Physiol.* 117:9–18.
Lee, et al., 1988. *EMBO J.* 7:1241.
Lerner, 1984. *Adv. Immunol.* 36:1.

Lesk (Ed.), 1988. *Computational Molecular Biology*, Oxford University Press, New York.
Leung, et al., 1990. *Curr. Genet.* 17:409–411.
Leutwiler, et al., 1986. *Nucl. Acids. Res.* 14:4051–4064.
Levy and Dean, 1998. *Plant Cell.* 10:1973–1989.
Lewis and Yamamoto, 1990. *Plant Physiol. Plant Mol. Biol.* 41: 455–496.
Li, et al., 2000. *Plant Cell* 5171–179.
Li, et al., 2000. *J. Biol. Chem.* 275: 6537–6545.
Lichtenstein and Draper, 1985. In: *DNA Cloning*, Vol. II, (D. M. Glover, Ed.), IRI Press, Oxford.
Lichtenstein and Fuller, 1987. In: *Genetic Engineering*, Vol. 6, Academic Press, London.
Livak, et al., 1978. *Proc. Natl. Acad. Sci. USA* 75:5613–5617.
Loh, et al., 1989. *Science* 243:217.
Longemann, et al., 1992. *Bio/Technology* 10:3305.
Lu, et al., 1997. *J. Agric. Food Chem.* 45: 2590–2592.
Luo, et al., 1988. *Plant Mol. Biol. Reporter* 6:165.
Lynn, et al., 1987. *Proc. Natl. Acad. Sci. USA* 84: 615–619.
Maas, et al., 1997. *Mol. Breeding* 3:15–28.
Maniatis, et al., 1982. *Molecular Cloning: A Laboratory Manual,* Cold Spring Harbor Laboratory, Cold Spring Harbor, N.Y.
Marita, et al., 1999. *Proc. Natl. Acad. Sci. USA* 96: 12328–12332.
Marshall, et al., 1992. *Theor. Appl. Genet.* 83:435.
Martin, et al., 1993. *Science* 262:1432.
Mathesius, et al., 1998. *Plant J.* 14: 23–34.
Matteucci and Caruthers, 1981. *J. Am. Chem. Soc.* 103:3185.
Melnikov, et al., 1999. *Nucleic Acids Research* 27(4): 1056–1062.
Meng and Campbell, 1997. *Phytochemistry* 44: 605–608.
Meyer, et al., 1987. *Nature* 330: 677–678.
Meyer, et al., 1996. *Proc. Natl. Acad. Sci. USA* 93: 6869–6874.
Meyer, et al., 1996b. Cloning of plant genes based on genetic map location. In A H Paterson, ed, Genome Mapping in Plants. Academic Press, New York N.Y., Landes Bioscience Publishers, Austin, Tex., pp 137–154
Meyer, et al., 1998. *Proc. Natl. Acad. Sci. USA* 95: 6619–6623.
Metzger, et al., 1988. *Nature* 334:31–36.
Miki, et al., 1990. *Theor. Appl. Genet.* 80:449.
Miki, et al., 1993. "Procedures for Introducing Foreign DNA into Plants," in *Methods in Plant Molecular Biology and Biotechnology,* Glick, et al., (Eds.), CRC Press, pp. 67–88.
Mindrinos, et al., 1994. *Cell.* 78:1089.
Mizukami, et al., 1996. *Plant Cell* 8:831–845.
Mizutani, et al., 1993b. *Biochem. Biophys. Res. Commun.* 190: 875–880.
Mizutani, et al., 1993a. *Plant Cell Physiol.* 34: 481–488.
Mol, et al., 1994. "Post-transcriptional inhibition of gene expression: sense and antisense genes." In: J. Paszkowski (Ed.), *Homologous Recombination and Gene Silencing in Plants*, Kluwer Academic Publishers, Dordrecht, Netherlands, pp. 309–334.
Monsour, et al., 1988. *Nature* 336:348–352.
Moyano, et al., 1996. *Plant Cell* 81: 519–1532.
Napoli, et al., 1990. *The Plant Cell* 2:279–289.
Neuhaus, et al., 1987. *Theor. Appl. Genet.* 75:30.
Nicholson and Hammerschmidt, 1992. *Annu. Rev. Phytopathol.* 30: 369–389.
Norris, et al., 1993. *Plant Mol. Biol.* 21:895–906.
Odell, et al., 1985. *Nature* 313:810–812.
Ohara, et al., 1989. *PNAS USA* 86:5673.
Omura and Sato, 1964. *J. Biol. Chem.* 239: 2370–2378.
Orr and Lynn, 1992. *Plant Physiol.* 98: 343–352.
Osakabe, et al., 1999. *Proc. Natl. Acad. Sci. USA* 96: 8955–8960.
Pakusch, et al., 1989. *Arch. Biochem. Biophys.* 271: 488–494.
Pakusch, et al., 1991. *Plant Physiol.* 95: 137–143.
Pang, et al., 1992. *Gene* 116:165.
Parsons, et al., 1997. *Proc. Natl. Acad. Sci. USA* 84:4161–4165.
Paszkowski, et al., 1984. *Embo. J* 3:2717–2722.
Pearson, et al., 1988. *Proc. Natl. Acad. Sci. U.S.A.* 85:2444–2448.
Pen, et al., 1992. *Bio/Technology* 10:292.
Pena, et al., 1987. *Nature* 325:274.
Pierrel, et al., 1994. *Eur. J. Biochem.* 224: 835–844.
Pilon-Smits, et al., 1998. *J. Plant Physiol.* 152:525–532.
Piquemal, et al., 1998. *Plant J.* 13: 71–83.
Pompon, et al., 1996. *Methods Enzymol.* 272: 51–64.
Przibilla, et al., 1991. *Plant Cell.* 3:169.
Raboy, et al., 1990. *Maydica* 35:383.
Raikhel, 1992. *Plant Phys.* 100:1627–1632.
Regan, 1994. *J. Biol. Chem.* 269:9.
Rethmeier, et al., 1996. *Plant J.* 12:895–899.
Rogers, et al., 1987. *Meth. in Enzymol.* 153:2531–277.
Rychlik, 1993. In White, B. A., Ed., "Methods in Molecular Biology," 15:31–39, PCR Protocols: Current Methods and Applications. Humania Press, Inc., totowa, N.J.
Sambrook, et al., 1989. "Molecular cloning." *A laboratory manual,* 2d Ed., Cold Spring Harbor Laboratory Press, Plainview, N.Y.
Sanders, et al., 1987. *Nucl. Acids. Res.* 15:1543–1558.
Sanger, et al., 1977. *Proc. Nat. Acad. Sci. USA* 74:5463–5467.
Sarthy, et al., 1987. *Appl. Environ. Microb.* 53:1996–2000.
Schafer, et al., 1998. *Plant Mol. Biol.* 37:87–97.
Schaffner, 1996. *Plant Mol. Biol. Rep.* 14:11–16.
Scharf, et al., 1986. *Science* 233:1076–1078.
Schmitt, 1964. *Self-sterility in sweetgum.* Ph.D. Thesis Dissertation, North Carolina State University.
Schmitt, et al., 1991. *Jour. Biol. Chem.* 266: 17416–17423.
Scopes, 1982. *Protein Purification: Principles and Practice*, Springer-Verlag, N.Y. *Sequence Analysis Software Package of the Genetics Computer Group*, Univ. of Wisconsin Biotechnology Center, Madison, Wis.
Sheehy, et al., 1988. *Proc. Nat'l. Acad. Sci.* 85:8805–8809.
Shiroza, et al., 1988. *J. Bacteriol.* 170:810.
Sieburth and Meyerowitz, 1997. *Plant Cell.* 9:355–365.
Silflow, et al., 1987. *Devel. Genet.* 8:435–460.
Silhavy, et al., 1984. Experiments with Gene Fusions, Cold Spring Harbor Laboratory, Cold Press Spring Harbor, N.Y.
Sogaard, et al., 1993. *J. Biol. Chem.* 268:22480.
Smith (Ed.), 1993. *Biocomputing Informatics and Genome Projects*, Academic press, New York.
Spargo, et al., 1996. *Mol. Cel. Probes* 10:247–256.
Sprague and Dudley, Eds., 1988. *Corn and Corn Improvement,* $3^{rd}$ Ed., American Society of Agronomy, Madison, Wis.
Springer, et al., 1995. *Science* 268:877–880.
Stachel, et al., 1985. *Nature* 318: 624–629.
Stafford and Dresler, 1972. *Plant Physiol,* 49: 590–595.
Steinmetz, et al., 1985. *Mol. Gen. Genet.* 200:220.
Strack and Mock, 1993. Hydroxycinnamic acids and lignins in Methods in Plant Biochemistry, Academic Press, New York N.Y., pp 45–97
Strack, 1980. *Z Naturforsch* 35c: 204–208.

Strauss and Meilan, 1998. *Tree Genetic Engineering Research Cooperative 1998 Annual Report.*
Sumitani, et al., 1993. *Biosci. Biotech. Biochem.* 57:1243.
Tabor, et al., 1985. *Proc. Acad. Sci. USA* 82:1074.
Takahashi, et al., 1989. *Mol. Gen. Genet.* 219:365–372.
Tamagnone, et al., 1998. *Plant Cell* 10: 1801–1816.
Tanaka and Kojima, 1991. *Arch. Biochem. Biophys.* 284: 151–157.
Taylor and Jorgensen, 1992. *J. Hered.* 83:11–17.
Taylor, et al., 1994. Abstract #497, Seventh International Symposium on Molecular Plant-Microbe Interactions.
Tavladoraki, et al., 1993. *Nature* 266:469.
Teutonico, et al., 1991. *Plant Physiol.* 97: 288–297.
Teutsch, et al., 1993. *Proc. Natl. Acad. Sci. USA* 90: 4102–4106.
Thein and Wallace, 1986. "The use of oligonucleotide as specific hybridization probes in the Diagnosis of Genetic Disorders," in *Human Genetic Diseases: A Practical Approach*, K. E. David, Ed., pp. 33–50, IRL Press, Herndon, Va.
Toubart, et al., 1992. *Plant J.* 2:367.
Turner and Somerville, 1997. *Plant Cell* 9: 689–701.
Urban, et al., 1994. *Eur. J. Biochem.* 222: 843–850.
Vain, et al., 1993. *Plant Cell, Tissue and Organ Culture* 33:237–246.
Van Damme, et al., 1994. *Plant Molec. Biol.* 24:825.
van der Meer, et al., 1992. *Plant Cell* 4: 253–262.
Van Doorsselaere, et al., 1995. *Plant J.* 8: 855–864.
Van Hartingsveldt, et al., 1993. *Gene* 127:87.
Van Ness and Chen, 199. *Nuc. Acids Res.* 19:5143–5151.
Vaughan and Butt, 1970. *Biochem. J.* 119: 89–94.
Vaughan and Butt, 1969. *Biochem. J.* 113: 109–115.
von Heinje, 1987. *Sequence Analysis in Molecular Biology*, Academic Press, New York.
Von Wachenfeldtand Johnson, 1995. Structures of eukaryotic cytochrome P450 enzymes in Cytochrome P450: Structure, Mechanism, and Biochemistry (Second Edition) (PR Ortiz de Montellano ed.), Plenum Press, New York.
Vorst, et al., 1990. *Plant Mol. Biol.* 14:491–499.
Wagner, et al., 1987. *Proc. Natl. Acad. Sci. USA* 84:2097–2100.
Walker, et al., 1992. *Proc. Natl. Acad. Sci. USA* 89:392.
Walker, et al., 1992. *Nucl. Acids. Res.* 20:1691–1696.
Wang, et al., 1997. *Arch. Biochem. Biophys.* 347: 249–255.
Weising, et al., 1988. *Ann. Rev. Genet.* 22:421–477.
Weissbach and Weissbach, Eds., 1988. *Methods for Plant Molecular Biology*, Academic Press, Inc., San Diego, Calif.
Weissbach and Weissbach, Eds., 1986. *Methods for Enzymology*, Volume 118, Academic Press, Inc., Orlando, Fla.
Wetmur and Davidson, 1968. *J. Mol. Biol.* 31:349–370.
Winkler, et al., 1998. *KA PLant Physiology* 118:743–749.
Wosnick, et al., 1987. *Gene* 60:115.
Wu and Wallace, 1989. *Genomics* 4:560–569.
Wu and Grossman, 1987. *Methods and Enzymology*, Vol. 153, "Recombinant DNA Part D", Academic Press, New York.
Ye, et al., 1994. *Plant Cell* 6: 1427–1439.
Ye and Varner, 1995. *Plant Physiol.* 108: 459–467.
Zaitlin, et al. (Eds.), 1985. *Biotechnology in Plant Science*, Academic Press, Inc., Orlando, Fla.
Zhijian Li, et al., 1992. *Plant Physiol.* 100:662–668.
Zhong, et al., 1998. *Plant Cell* 10: 2033–2045.
Zhou, et al., 1983. *Methods in Enzymology* 101:433.
Patents and Patent Applications:
Hitzeman, et al., EP 73,675A.
PCT International Publication Number WO 92/05257.
PCT published application No. WO 93/02197.
PCT International Publication No. WO 98/09521.
PCT International Publication No. WO 90/08829.
PCT International Publication No. WO 89/10396.
European published application No. 0 242 246.
European published application No. 0 333 033.
U.S. Pat. No. 4,554,101.
U.S. Pat. No. 4,683,195.
U.S. Pat. No. 4,683,202.
U.S. Pat. No. 4,769,061.
U.S. Pat. No. 4,810,648.
U.S. Pat. No. 4,940,835.
U.S. Pat. No. 4,975,374.
U.S. Pat. No. 5,106,739.
U.S. Pat. No. 5,266,361
U.S. Pat. No. 5,268,526.
U.S. Pat. No. 5,270,184.
U.S. Pat. No. 5,290,294.
U.S. Pat. No. 5,322,938.
U.S. Pat. No. 5,409,818.
U.S. Pat. No. 5,436,146.
U.S. Pat. No. 5,455,166.
U.S. Pat. No. 5,477,002.
U.S. Pat. No. 5,607,914.
U.S. Pat. No. 5,633,441.
U.S. Pat. No. 5,659,026.
U.S. Pat. No. 5,691,198.
U.S. Pat. No. 5,710,267.
U.S. Pat. No. 5,723,763.
U.S. Pat. No. 5,723,765.
U.S. Pat. No. 5,735,500.
U.S. Pat. No. 5,744,693.
U.S. Pat. No. 5,747,469.
U.S. Pat. No. 5,808,034.
U.S. Pat. No. 5,850,020.

What is claimed is:

1. A method of altering the content or composition of lignin in a plant, comprising:
   (a) transforming plant cells with an isolated DNA comprising a nucleic acid sequence operably linked in either sense or antisense orientation to at least one regulatory sequence, wherein said nucleic acid comprises a nucleotide sequence coding for
      (i) an *Arabidopsis* P-coumarate 3-hydroxylase (C3H) comprising an amino acid sequence set forth in SEQ ID NO: 4 or SEQ ID NO: 6, or
      (ii) a protein comprising an amino acid sequence that has at least 90% identity with an amino acid set forth in SEQ ID NO: 4 or SEQ ID NO: 6, and has P-coumarate 3-hydroxylase activity, and
   (b) regenerating said plant from said transformed plant cells, wherein expression of said DNA alters the content and composition of lignin in said plant.

2. A plant transformed by the method of claim 1.

3. The method of claim 1 wherein the protein comprising an amino acid sequence has at least 95–98% identity with an amino acid sequence set forth in SEQ ID NO: 4 or SEQ ID NO: 6.

* * * * *